US008617816B2

(12) United States Patent
Simen et al.

(10) Patent No.: US 8,617,816 B2
(45) Date of Patent: Dec. 31, 2013

(54) SYSTEM AND METHOD FOR DETECTION OF HIV DRUG RESISTANT VARIANTS

(75) Inventors: Birgitte Binderup Simen, Orange, CT (US); Christine Lubeski, Niantic, CT (US); Jan Fredrik Simons, Burlingame, CA (US)

(73) Assignee: 454 Life Sciences, A Roche Company, Branford, CT (US)

( * ) Notice: Subject to any disclaimer, the term of this patent is extended or adjusted under 35 U.S.C. 154(b) by 471 days.

(21) Appl. No.: 12/449,813

(22) PCT Filed: Mar. 14, 2008

(86) PCT No.: PCT/US2008/003424
§ 371 (c)(1),
(2), (4) Date: Aug. 26, 2009

(87) PCT Pub. No.: WO2008/115427
PCT Pub. Date: Sep. 25, 2008

(65) Prior Publication Data
US 2010/0203497 A1    Aug. 12, 2010

Related U.S. Application Data

(63) Continuation-in-part of application No. 11/107,781, filed on Apr. 12, 2005.

(60) Provisional application No. 60/918,440, filed on Mar. 16, 2007, provisional application No. 60/972,387, filed on Sep. 14, 2007.

(51) Int. Cl.
*C12Q 1/68* (2006.01)
*C12P 19/34* (2006.01)
*C07H 21/04* (2006.01)

(52) U.S. Cl.
USPC .............. 435/6.12; 435/91.2; 536/24.33

(58) Field of Classification Search
None
See application file for complete search history.

(56) References Cited

U.S. PATENT DOCUMENTS

| | | |
|---|---|---|
| 4,683,194 A | 7/1987 | Saiki et al. .................. 435/6 |
| 4,683,195 A | 7/1987 | Mullis et al. ................. 435/6 |
| 4,683,202 A | 7/1987 | Mullis ...................... 435/91.2 |
| 5,420,030 A | 5/1995 | Reitz, Jr. et al. |
| 5,599,662 A | 2/1997 | Respess |
| 5,614,413 A | 3/1997 | Morrow |
| 5,712,385 A | 1/1998 | McDonough et al. |
| 5,733,781 A | 3/1998 | Ryder et al. |
| 5,814,444 A | 9/1998 | Rabinovitch ................ 435/6 |
| 5,847,096 A | 12/1998 | Schubert et al. |
| 5,856,088 A | 1/1999 | McDonough et al. |
| 5,908,978 A | 6/1999 | Amerson et al. ........... 800/319 |
| 5,942,392 A | 8/1999 | Amouyel et al. ............. 435/6 |
| 5,962,665 A | 10/1999 | Kroeger et al. |
| 5,989,892 A | 11/1999 | Nishimaki et al. ........ 435/252.1 |
| 6,194,142 B1 | 2/2001 | Moncany et al. |
| 6,210,891 B1 | 4/2001 | Nyren et al. ................... 435/6 |
| 6,235,881 B1 | 5/2001 | Kraus et al. |
| 6,251,661 B1 | 6/2001 | Urabe et al. ............. 435/287.2 |
| 6,258,568 B1 | 7/2001 | Nyren ........................ 435/91.1 |
| 6,274,320 B1 | 8/2001 | Rothberg et al. .............. 435/6 |
| 6,300,056 B1 | 10/2001 | Irvine et al. |
| 6,379,957 B1 | 4/2002 | Johnston-Dow et al. |
| 6,489,103 B1 | 12/2002 | Griffiths et al. ............... 435/6 |
| 6,492,110 B1 | 12/2002 | Hahn et al. |
| 6,566,513 B1 | 5/2003 | Guertler et al. |
| 6,602,705 B1 | 8/2003 | Barnett et al. |
| 6,610,476 B1 | 8/2003 | Chang et al. |
| 6,649,749 B2 | 11/2003 | McDonough et al. |
| 6,712,612 B1 | 3/2004 | Tung |
| 6,776,986 B1 | 8/2004 | Boehnlein et al. |
| 6,803,187 B1 | 10/2004 | Stuyver |
| 6,806,046 B2 | 10/2004 | Johnston-Dow et al. |
| 6,858,712 B1 | 2/2005 | Chang et al. |

(Continued)

FOREIGN PATENT DOCUMENTS

JP    2001506864 A    5/2001
WO   WO 98/13523    4/1998

(Continued)

OTHER PUBLICATIONS da Mota et al. (2002), European Journal of Immunogenetics, 29:223-227.
Office Action issued in Chinese Application No. 200880008644.8 mailed Dec. 21, 2011. (English Translation).
Dressman et al. (2003), Proceedings of the National Academy of Sciences, USA, 15:8817-8822.
Thomas et al. (2006), Nature Medicine, 12:852-856.

(Continued)

*Primary Examiner* — Suryaprabha Chunduru
(74) *Attorney, Agent, or Firm* — Mintz Levin Cohn Ferris Glovsky and Popeo, P.C.; Ivor R. Elrifi; Christina K. Stock, Esq.

(57) ABSTRACT

In one embodiment of the invention a method for detecting low frequency occurrence of one or more HIV sequence variants associated with drug resistance is describe that comprises generating cDNA species from RNA molecules in an HIV sample population; amplifying first amplicons from the cDNA species, wherein each amplicon comprises amplified copies and is amplified with a pair of nucleic acid primers that define a locus; clonally amplifying the amplified copies of the first amplicons to produce second amplicons that comprise an immobilized population of substantially identical copies from one of the amplified copies of first amplicons; determining a nucleic acid sequence composition from at least 100 of the immobilized populations in parallel on a single instrument; detecting one or more sequence variants that occur at a frequency of 5% or less in the nucleic acid sequence composition of the at least 100 immobilized populations; and correlating the detected sequence variants with variation associated with HIV drug resistance.

19 Claims, 19 Drawing Sheets

(56) References Cited

U.S. PATENT DOCUMENTS

| | | | |
|---|---|---|---|
| 6,897,301 B2 | 5/2005 | Hahn et al. | |
| 6,946,254 B2 | 9/2005 | Yang et al. | |
| 7,030,234 B2 | 4/2006 | Mauclere et al. | |
| 7,078,516 B1 | 7/2006 | Moncany et al. | |
| 7,105,318 B2 | 9/2006 | Kessler et al. | |
| 7,122,180 B2 | 10/2006 | Aldovini | |
| 7,169,396 B2 | 1/2007 | Hahn et al. | |
| 7,183,047 B2 | 2/2007 | Brack-Werner et al. | |
| 7,196,186 B2 | 3/2007 | Lisziewicz et al. | |
| 7,206,699 B2 * | 4/2007 | Larder et al. | 702/19 |
| 7,323,305 B2 | 1/2008 | Leamon et al. | 435/6 |
| 7,888,034 B2 * | 2/2011 | Simen et al. | 435/5 |
| 2001/0024790 A1 | 9/2001 | Kambara et al. | 435/6 |
| 2003/0022207 A1 | 1/2003 | Balasubramanian et al. | |
| 2003/0148344 A1 | 8/2003 | Rothberg et al. | 435/6 |
| 2003/0215821 A1 | 11/2003 | Gunderson et al. | 435/6 |
| 2004/0072200 A1 | 4/2004 | Rigler et al. | 435/6 |
| 2005/0079510 A1 | 4/2005 | Berka et al. | 506/16 |
| 2005/0137387 A1 | 6/2005 | Mullins et al. | |
| 2006/0008824 A1 | 1/2006 | Ronaghi et al. | 435/6 |
| 2006/0228721 A1 | 10/2006 | Leamon et al. | 435/6 |
| 2006/0269934 A1 | 11/2006 | Woudenberg et al. | 435/6 |

FOREIGN PATENT DOCUMENTS

| | | |
|---|---|---|
| WO | WO 98/18967 | 5/1998 |
| WO | WO-9844151 A1 | 10/1998 |
| WO | WO 01/68897 | 9/2001 |
| WO | WO 02/20852 | 3/2002 |
| WO | WO 02/38806 | 5/2002 |
| WO | WO-0246456 A1 | 6/2002 |
| WO | WO 03/078659 | 9/2003 |
| WO | WO 2004/069849 | 8/2004 |
| WO | WO 2004/070007 | 8/2004 |
| WO | WO 2005/003375 | 1/2005 |
| WO | WO 2005/121379 | 12/2005 |
| WO | WO 2006/110855 | 10/2006 |
| WO | WO 2007088201 A1 * | 8/2007 |
| WO | WO 2008/115427 | 9/2008 |

OTHER PUBLICATIONS

Office Action issued in Japanese Application No. 2009-553642 mailed May 18, 2012. (English Translation).
Examination Report issued in European Application No. 08726885.3 mailed Jun. 8, 2012.
Ahmadian et al. (2000), Analytical Biochemistry, 280:103-110.
Bains et al. (1998), J.Theor. Biol.,135, 303-307.
Benomar et al. (1995), Nature Genetics, 10:84-88.
Blanton et al. (1991), Genomics, 11:857-869.
Botstein et al. (1980), American Journal of Human Genetics, 32:314-331.
Cargill et al. (1999), Nature Genetics, 22:231-238.
Cavenee et al. (1983), Nature, 305:779-784.
Collins et al. (1996), Proc. Natl. Acad Sci. USA, 93:14771-14775.
Davies et al. (1994), Nature, 371:130-136.
Dinauer et al. (2000), Tissue Antigens, 55:364-368.
Drnanac et al. (1989), Genomics, 4:114-128.
Fakhrai-Rad et al., Human Mutation, 19:479-485 (2002).
Garcia-Martinez et al. (2001), Nucleic Acids Research, 29:178-180.
GenBank Accession No. AF307851 (2001), Accessed May 25, 2006, (2 pages).
Grahn et al. (2003), FEMS Microbiology Letters, 219: 87-91.
Hamilton et al. (2001), BioTechniques, 31:370-383.
Invitrogen (2005), Product Information for Dynal Dynabeads M-280 Streptavidin, 2 pages.
Johnson et al., Topics in HIV Medicine, International AIDS Society, US 13:125-131 (2005).
Jonasson et al. (2002), APMIS,110:263-272.
Khrapko et al. (1989), FEBS Letters, 256:118-122.
Koufos et al. (1984), Nature, 309:170-172.
Kruglyak et al. (2001), Nature Genetics, 27:234-236.
Lathrop (1984), Proc. Natl. Acad. Sci. USA, 81:3443-3446.
Leamon et al. (2003), Electrophoresis, 24:3769-3777.
Legius et al. (1993), Nature Genetics, 3:122-126.
Lysov et al. (1988), Dokl Akad Nauk SSSR, 303:1508-1511.
Mattila et al. (1991) Nucleic Acids Research, 19: 4967-4973.
Maxam et al. (1977), Proc. Natl. Acad. Sci. USA, 74:560-564.
Mei et al. (2000), Genome Research, 10:1126-1137.
Monstein et al. (2001), FEMS Microbiology Letters, 199:103-107.
Nakamura et al. (1987), Science, 235:1616-1622.
Nakano et al. (2003), Journal of Biotechnology, 102:117-124.
Norgaard et al. (1997), Tissue Antigens, 49:455-465.
Pevzner (1989), Journal of Biomolecular Structure & Dynamics, 7:063-073.
Rickert et al., (2002), BioTechniques 32:592-603.
Ronaghi et al. (1998), Science, 281:363-365.
Ronaghi, et al. (1996), Analytical Biochemistry, 242:84-89.
Saiki et al. (1985), Science, 230:1350-1354.
Saiki et al., (1986) Nature, 324:163-166.
Sanger et al. (1977), Proc. Natl. Acad. Sci. USA, 74:5463-5467.
Scharf et al. (1986), Science, 233:1076-1078.
Shifman et al., Molecular and Cellular Probes, 16:429-434 (2002).
Shimizu et al. (2002), DNA Research, 9:173-178.
Smith (1968), Ann. Hum. Genet., 32:127-150.
Smith et al. (1991), Breast Cancer Research and Treatment 18:S51-S54.
Southern et al. (1992), Genomics, 13:1008-1017.
Steffens et al. (1997), J. Forensic Sci., 42:452-460.
Todd et al. (1995), Proc. Natl. Acad. Sci. USA, 92:8560-8565.
Tsang et al. (2004), BioTechniques, 36:682-688.
Wang et al. (1998) Science, 280:1077-1082.
Zengmin et al., Proceedings of the National Academy of Sciences, 100:414-419 (2003).
International Search Report for PCT/US2006/013753 dated Dec. 13, 2006.
International Search Report for PCT/US2008/003424 dated Sep. 18, 2008.
Office Action issued in Canadian Application No. 2,604,095 mailed Aug. 30, 2012.
International Preliminary Report on Patentability issued in International Application No. PCT/US2006/013753 mailed Oct. 16, 2007.
Office Action issued in Japanese Application No. 2008-506657 dated Nov. 21, 2012. (English Translation Attached).
Office Action issued in Chinese Application No. 200880008644.8 mailed May 7, 2012. (Chinese Original and English Translation).
Office Action issued in Chinese Application No. 200880008644.8 mailed Sep. 29, 2012. (Chinese Original and English Translation).
Office Action issued in Japanese Application No. 2009-553642 mailed Apr. 15, 2013. (Japanese Original and English Translation).
Office Action Issued in Chinese Application No. 200880008644.8 dated May 9, 2013. (English Translation and Chinese Original).

* cited by examiner

A

B

A

B

C

Amplicon A = 195 bp
Amplicon B = 282 bp
Amplicon C = 354 bp

Amplicon 1 = 258 bp
Amplicon 2 = 251 bp
Amplicon 3 = 270 bp
Amplicon 4 = 418 bp
Amplicon 5 = 402 bp

FIGURE 18

```
              ....|....| ....|....| ....|....|
                  155       165       175
cladeBcons                CCTC AGATCACTCT TTGGCAACGA
cladeCcons                CCTC ACTCAAATCT TTGGCAGCGA ....|....| ....|....| ....|....| ....|....| ....|....| ....|....|
             185       195       205       215       225       235
cladeBcons  CCCCTCGTCA AAGTAAAGAT AGGGGGGCAA CTAAAGGAAG CTCTATTAGA TACAGGAGCA
cladeCcons  CCCCTTGTCT CAATAAAAGT AGGGGGCCAG ATAAAGGAGG CTCTCTTAGA CACAGGAGCA ....|....| ....|....| ....|....| ....|....| ....|....| ....|....|
             245       255       265       275       285       295
cladeBcons  GATGATACAG TATTAGAAGA AATGAATTTG CCAGGAAGAT GGAAACCAAA AATGATAGGG
cladeCcons  GATGATACAG TATTAGAAGA AATAAATTTG CCAGGAAAAT GGAAACCAAA AATGATAGGA ....|....| ....|....| ....|....| ....|....| ....|....| ....|....|
             305       315       325       335       345       355
cladeBcons  GGAATTGGAG GTTTTATCAA AGTAAGACAG TATGATCAGA TACCCATAGA AATCTGTGGA
cladeCcons  GGAATTGGAG GTTTTATCAA AGTAAGACAG TATGATCAAA TACTTATAGA AATTTGTGGA ....|....| ....|....| ....|....| ....|....| ....|....| ....|....|
             365       375       385       395       405       415
cladeBcons  CATAAAGCTA TAGGTACAGT ATTAGTAGGA CCTACACCTG TCAACATAAT TGGAAGAAAT
cladeCcons  AAAAAGGCTA TAGGTACAGT ATTAGTAGGA CCTACACCTG TCAACATAAT TGGAAGAAAT ....|....| ....|....| ....|....| ....|....| ....|....| ....|....|
             425       435       445       455       465       475
cladeBcons  CTGTTGACTC AGATTGGTTG CACTTTAAAT TTTCCCATTA GTCCTATTGA AACTGTACCA
cladeCcons  ATGTTGACTC AGCTTGGATG CACACTAAAT TTTCCAATTA GTCCCATTGA AACTGTACCA ....|....| ....|....| ....|....| ....|....| ....|....| ....|....|
             485       495       505       515       525       535
cladeBcons  GTAAAATTAA AGCCAGGAAT GGATGGCCCA AAAGTTAAAC AATGGCCATT GACAGAAGAA
cladeCcons  GTAAAATTAA AGCCAGGAAT GGATGGCCCA AAGGTTAAAC AATGGCCATT GACAGAAGAG ....|....| ....|....| ....|....| ....|....| ....|....| ....|....|
             545       555       565       575       585       595
cladeBcons  AAAATAAAAG CATTAGTAGA AATTTGTACA GAAATGGAAA AGGAAGGGAA AATTTCAAAA
cladeCcons  AAAATAAAAG CATTAACAGC AATTTGTGAA GAAATGGACA AGGAAGGAAA AATTACAAAA ....|....| ....|....| ....|....| ....|....| ....|....| ....|....|
             605       615       625       635       645       655
cladeBcons  ATTGGGCCTG AAAATCCATA CAATACTCCA GTATTTGCCA TAAAGAAAAA AGACAGTACT
cladeCcons  ATTGGGCCTG AAAATCCATA TAACACTCCA GTATTTGCCA TAAAAAAGAA GGACAGTACT ....|....| ....|....| ....|....| ....|....| ....|....| ....|....|
             665       675       685       695       705       715
cladeBcons  AAATGGAGAA AATTAGTAGA TTTCAGAGAA CTTAATAAGA GAACTCAAGA CTTCTGGGAA
cladeCcons  AAGTGGAGAA AATTAGTAGA TTTCAGGGAA CTCAATAAAA GAACTCAAGA CTTTTGGGAA ....|....| ....|....| ....|....| ....|....| ....|....| ....|....|
             725       735       745       755       765       775
cladeBcons  GTTCAATTAG GAATACCACA TCCCGCAGGG TTAAAAAAGA AAAAATCAGT AACAGTACTG
cladeCcons  GTTCAATTAG GAATACCACA CCCAGCAGGG TTAAAAAAGA AAAAATCAGT GACAGTACTG
```

FIGURE 18 (Continued)

```
              ....|....| ....|....| ....|....| ....|....| ....|....| ....|....|
                  785        795        805        815        825        835
cladeBcons    GATGTGGGTG ATGCATATTT TTCAGTTCCC TTAGATAAAG ACTTCAGGAA GTATACTGCA
cladeCcons    GATGTGGGGG ATGCATATTT TTCAGTTCCT TTAGATGAAG GCTTCAGGAA ATATACTGCA ....|....| ....|....| ....|....| ....|....| ....|....| ....|....|
                  845        855        865        875        885        895
cladeBcons    TTTACCATAC CTAGTATAAA CAATGAGACA CCAGGGATTA GATATCAGTA CAATGTGCTT
cladeCcons    TTCACCATAC CTAGTATAAA CAATGAAACA CCAGGGATTA GATATCAATA TAATGTGCTT ....|....| ....|....| ....|....| ....|....| ....|....| ....|....|
                  905        915        925        935        945        955
cladeBcons    CCACAGGGAT GGAAAGGATC ACCAGCAATA TTCCAAAGTA GCATGACAAA AATCTTAGAG
cladeCcons    CCACAGGGAT GGAAAGGATC ACCAGCAATA TTCCAGAGTA GCATGACAAA AATCTTAGAG ....|....| ....|....| ....|....| ....|....| ....|....| ....|....|
                  965        975        985        995       1005       1015
cladeBcons    CCTTTTAGAA AACAAAATCC AGACATAGTT ATCTATCAAT ACATGGATGA TTTGTATGTA
cladeCcons    CCCTTTAGGG CACAAAATCC AGAAATAGTC ATCTATCAAT ATATGGATGA CTTGTATGTA ....|....| ....|....| ....|....| ....|....| ....|....| ....|....|
                 1025       1035       1045       1055       1065       1075
cladeBcons    GGATCTGACT TAGAAATAGG GCAGCATAGA ACAAAAATAG AGGAACTGAG ACAACATCTG
cladeCcons    GGATCTGACT TAGAAATAGG GCAACATAGA GCAAAAATAG AGGAGTTAAG AGAACATCTA ....|....| ....|....| ....|....| ....|....| ....|....| ....|....|
                 1085       1095       1105       1115       1125       1135
cladeBcons    TTGAGGTGGG GATTTACCAC ACCAGACAAA AAACATCAGA AAGAACCTCC ATTCCTTTGG
cladeCcons    TTAAAGTGGG GATTTACCAC ACCAGACAAG AAACATCAGA AAGAACCCCC ATTTCTTTGG ....|....| ....|....| ....|....| ....|....| ....|....| ....|....|
                 1145       1155       1165       1175       1185       1195
cladeBcons    ATGGGTTATG AACTCCATCC TGATAAATGG ACAGTACAGC CTATAGTGCT GCCAGAAAAA
cladeCcons    ATGGGGTATG AACTCCATCC TGACAAATGG ACAGTACAGC CTATACAGCT GCCAGAAAAG ....|....| ....|....| ....|....| ....|....| ....|....| ....|....|
                 1205       1215       1225       1235       1245       1255
cladeBcons    GACAGCTGGA CTGTCAATGA CATACAGAAG TTAGTGGGAA AATTGAATTG GGCAAGTCAG
cladeCcons    GATAGCTGGA CTGTCAATGA TATACAGAAG TTAGTGGGAA AATTAAACTG GGCAAGTCAG ....|....| ....|....| ....|....| ....|....| ....|....| ....|....|
                 1265       1275       1285       1295       1305       1315
cladeBcons    ATTTACGCAG GGATTAAAGT AAAGCAATTA TGTAAACTCC TTAGGGGAAC CAAAGCACTA
cladeCcons    ATTTACCCAG GGATTAAAGT AAGGCAACTT TGTAAACTCC TTAGGGGGGC CAAAGCACTA ....|....| ....|....| ....|....| ....|....| ....|....| ....|....|
                 1325       1335       1345       1355       1365       1375
cladeBcons    ACAGAAGTAA TACCACTAAC AGAAGAAGCA GAGCTAGAAC TGGCAGAAAA CAGGGAAATT
cladeCcons    ACAGACATAG TACCACTAAC TGAAGAAGCA GAATTAGAAT TGGCAGAGAA CAGGGAAATT ....|....| ....|....| ....|....|  ....|.
                 1385       1395       1405        1415
cladeBcons    CTAAAAGAAC CAGTACATGG AGTGTATTAT GACCCA
cladeCcons    CTAAAAGAAC CAGTACATGG AGTATATTAT GACCCA
```

SYSTEM AND METHOD FOR DETECTION OF HIV DRUG RESISTANT VARIANTS

RELATED APPLICATIONS

The present application is a National Stage of International Application No. PCT/US2008/003424, filed on Mar. 14, 2008, and claiming priority from U.S. Provisional Patent Application Ser. No. 60/918,440, titled "System and Method For Design and Use of HIV Primer Species", filed Mar. 16, 2007; and U.S. Provisional Patent Application Ser. No. 60/972,387, titled "System and Method For Design and Use of HIV Primer Species", filed Sep. 14, 2007; the present application is also a continuation in part of U.S. patent application Ser. No. 11/104,781, titled "Methods for determining sequence variants using ultra-deep sequencing", filed Apr. 12, 2005; each of which is incorporated by reference herein in its entirety for all purposes.

FIELD OF THE INVENTION

The invention provides methods, reagents and systems for detecting and analyzing sequence variants associated with drug resistance in HIV-1 Glade B and Glade C where the variants may include single nucleotide polymorphisms (SNPs), insertion/deletion variant (referred to as "indels") and allelic frequencies, in a population of target polynucleotides in parallel. The invention also relates to a method of investigating by parallel pyrophosphate sequencing nucleic acids replicated by polymerase chain reaction (PCR), for the identification of mutations and polymorphisms of both known and unknown sequences. The invention involves using nucleic acid primers specifically designed to the protease and reverse transcriptase regions of HIV RNA or its complementary DNA that have a low rate of mutation in order to amplify nucleic acids in a target HIV nucleic acid population which are suspected of containing drug resistant sequence variants (also referred to as quasispecies) to generate individual amplicons. Thousands of individual HIV amplicons are sequenced in a massively parallel, efficient, and cost effective manner to generate a distribution of the sequence variants found in the populations of amplicons that enables greater sensitivity of detection over previously employed methods.

BACKGROUND OF THE INVENTION

Genomic DNA varies significantly from individual to individual, except in identical siblings. Many human diseases arise from genomic variations. The genetic diversity amongst humans and other life forms explains the heritable variations observed in disease susceptibility. Diseases arising from such genetic variations include Huntington's disease, cystic fibrosis, Duchenne muscular dystrophy, and certain forms of breast cancer. Each of these diseases is associated with a single gene mutation. Diseases such as multiple sclerosis, diabetes, Parkinson's, Alzheimer's disease, and hypertension are much more complex. These diseases may be due to polygenic (multiple gene influences) or multi factorial (multiple gene and environmental influences) causes. Many of the variations in the genome do not result in a disease trait. However, as described above, a single mutation can result in a disease trait. Further, many viral genomes are well known to be very diverse and highly mutagenic where variation may confer certain traits to a virus that alters disease progression or treatment regimens. The ability to scan the human or viral genomes to identify the location of genes or specific mutations which underlie or are associated with the pathology of such diseases is an enormously powerful tool in medicine and human biology.

Several types of sequence variations, including insertions and deletions (indels), differences in the number of repeated sequences, and single base pair differences (SNPs) result in genomic diversity. Single base pair differences, referred to as single nucleotide polymorphisms (SNPs) are the most frequent type of variation in the human genome (occurring at approximately 1 in $10^3$ bases). A SNP is a genomic position at which at least two or more alternative nucleotide alleles occur at a relatively high frequency (greater than 1%) in a population. A SNP may also be a single base (or a few bases) insertion/deletion variant (referred to as "indels"). SNPs are well-suited for studying sequence variation because they are relatively stable (i.e., exhibit low mutation rates) and because single nucleotide variations (including insertions and deletions) can be responsible for inherited traits. It is understood that in the discussion above, the term SNP is also meant to be applicable to "indel" (defined below).

Polymorphisms identified using microsatellite-based analysis, for example, have been used for a variety of purposes. Use of genetic linkage strategies to identify the locations of single Mendelian factors has been successful in many cases (Benomar et al. (1995), Nat. Genet., 10:84-8; Blanton et al. (1991), Genomics, 11:857-69). Identification of chromosomal locations of tumor suppressor genes has generally been accomplished by studying loss of heterozygosity in human tumors (Cavenee et al. (1983), Nature, 305:779-784; Collins et al. (1996), Proc. Natl. Acad. Sci. USA, 93:14771-14775; Koufos et al. (1984), Nature, 309:170-172; and Legius et al. (1993), Nat. Genet., 3:122-126). Additionally, use of genetic markers to infer the chromosomal locations of genes contributing to complex traits, such as type I diabetes (Davis et al. (1994), Nature, 371:130-136; Todd et al. (1995), Proc. Natl. Acad. Sci. USA, 92:8560-8565) has become a focus of research in human genetics.

Although substantial progress has been made in identifying the genetic basis of many human diseases, current methodologies used to develop this information are limited by prohibitive costs and the extensive amount of work required to obtain genotype information from large sample populations. These limitations make identification of complex gene mutations contributing to disorders such as diabetes extremely difficult. Techniques for scanning the human genome to identify the locations of genes involved in disease processes began in the early 1980s with the use of restriction fragment length polymorphism (RFLP) analysis (Botstein et al. (1980), Am. J. Hum. Genet., 32:314-31; Nakamura et al. (1987), Science, 235:1616-22). RFLP analysis involves Southern blotting and other techniques. Southern blotting is both expensive and time-consuming when performed on large numbers of samples, such as those required to identify a complex genotype associated with a particular phenotype. Some of these problems were avoided with the development of polymerase chain reaction (PCR) based microsatellite marker analysis. Microsatellite markers are simple sequence length polymorphisms (SSLPs) consisting of di-, tri-, and tetra-nucleotide repeats.

Other types of genomic analysis are based on use of markers which hybridize with hypervariable regions of DNA having multiallelic variation and high heterozygosity. The variable regions which are useful for fingerprinting genomic DNA are tandem repeats of a short sequence referred to as a mini satellite. Polymorphism is due to allelic differences in the number of repeats, which can arise as a result of mitotic or meiotic unequal exchanges or by DNA slippage during replication.

Each of these current methods has significant drawbacks because they are time consuming and limited in resolution. While DNA sequencing provides the highest resolution, it is also the most expensive method for determining variants. For example, the determination of SNP frequency among a population of 1000 different samples is very expensive using the methods described above and the determination of SNP frequency among a population of 100,000 samples is prohibitive.

The Human Immunodeficiency Virus (generally referred to as HIV) is a disease where the sensitivity provided by DNA sequencing can have a great impact. This is particularly evident where DNA sequencing can provide highly sensitive detection of drug resistant HIV strains early in treatment when the frequency of each drug resistant strain is relatively low in the population.

HIV continues to be a major problem worldwide, even though a plethora of compounds have been approved for treatment. There are currently six classes of drugs, encompassing nucleoside/nucleotide reverse transcriptase inhibitors, non-nucleoside reverse transcriptase inhibitors, protease inhibitors, one fusion inhibitor, one chemokine receptor inhibitor, and one integrase inhibitor. These target four steps in the life cycle of HIV: the reverse transcription of the virion RNA to DNA, the integration of proviral DNA into the host genome, the cleavage of polypeptide viral gene products into functional proteins, and viral entry at the cell surface.

A major problem in the fight against HIV and AIDS is the development of drug resistance mutations. The International AIDS Society currently recognizes 73 amino acid residues where mutations have been associated with drug-resistance, 37 in the protease, 27 in the reverse transcriptase, 7 in the envelope, and 2 in the integrase (Johnson et al., Topics in HIV medicine (2007), 15:119, which is incorporated by reference herein in its entirety for all purposes). The list is updated at least once per year. Some of these mutations are specific to certain drugs, while others, either alone or in combination, lead to drug class resistance.

Due to the error-prone nature of viral reverse transcriptase and the high viral turnover (t½=1-3 days), the HIV genome mutates very rapidly. Reverse transcriptase is estimated to generate, on average, one mutation per replication of the 9.7 Kb genome that does not dramatically affect the ability of the virus to propagate. This leads to the formation of 'quasispecies', where many different mutants exist in a dynamic relationship.

HIV patients are benefiting from antiviral treatment in terms of an increased life span, but many experience several episodes of so-called virological failure when they develop resistance to a certain drug or drug combination. Virological failure dramatically decreases the chance of survival (Hennessey et al., AIDS Res Hum Retroviruses (2000), 16:103, which is incorporated by reference herein in its entirety for all purposes).

It has been hypothesized that the presence of resistance-conferring mutations in a subset of the quasispecies found in a single patient before the initiation of treatment will lead to outgrowth of resistant virus and subsequent virological failure (Coffin, Science (1995), which is incorporated by reference herein in its entirety for all purposes). If this is correct, it would be of enormous benefit to detect mutations present at low frequencies before a treatment decision is made. Many laboratories have developed specialized techniques such as oligonucleotide arrays or real time PCR assays, but these are limited to determining the viral genotype at pre-selected nucleotide positions and need adjustment every time new resistance mutations are recognized. Direct sequencing is superior in that it is not biased towards certain nucleotide species/residues and also can identify new drug resistance-linked mutations. Currently, kits based on traditional Sanger sequencing are available to detect drug-resistance mutations, but unless the viral species are first sub-cloned, these systems are unable to reliably detect mutations with a frequency below 25%. Sequencing of sub-cloned species has clearly demonstrated that low-frequency resistance mutations do exist within a single patient-derived viral population and that many of these are missed by standard bulk sequencing (Palmer et al., J. Clin. Microbiol. (2005), 43:406, which is incorporated by reference herein in its entirety for all purposes). Additional work has also shown that approximately 10% of chronically HIV-infected, drug-naïve patients harbor resistance mutations (Novak et al., Clin. Infect. Dis. (2005), 40:468, which is incorporated by reference herein in its entirety for all purposes). It is quite reasonable to assume that these low-frequency, persistent resistance-linked mutations are present before treatment initiation and affect treatment outcome.

Therefore, efficient detection of these mutations through sequencing enables substantial advancement in knowledge of the disease and treatment possibilities from early detection. Further, embodiments of high throughput sequencing techniques enabled for what may be referred to as "Massively Parallel" processing have substantially more powerful analysis, sensitivity, and throughput characteristics than previous sequencing techniques. For example, the high throughput sequencing technologies employing HIV specific primers of the presently described invention are capable of achieving a sensitivity of detection of low abundance alleles that include a frequency of 1% or less of the allelic variants in a population. As described above, this is important in the context of detecting HIV variants, particularly for drug resistant variants where high sensitivity provides an important early detection mechanism that results in a substantial therapeutic benefit.

BRIEF SUMMARY OF THE INVENTION

The invention relates to methods of diagnosing a number of low frequency sequence variants in HIV drug resistance (e.g., allelic variants, single nucleotide polymorphism variants, indel variants) by the identification of specific DNA. Current technology allows detection of SNPs, for example, by polymerase chain reaction (PCR). However, SNPs detection by PCR requires the design of special PCR primers which hybridize to one type of SNP and not another type of SNP. Furthermore, although PCR is a powerful technique, the specific PCR of alleles require prior knowledge of the nature (sequence) of the SNP, as well as multiple PCR runs and analysis on gel electrophoresis to determine an allelic frequency. For example, an allelic frequency of 5% (i.e., 1 in 20) would require at a minimum 20 PCR reactions for its detection. The amount of PCR and gel electrophoresis needed to detect an allelic frequency goes up dramatically as the allelic frequency is reduced, for example to 4%, 3%, 2% or 1% or less.

None of the current methods has provided a simple and rapid method of detecting SNPs, including SNPs of low abundance, by identification of specific DNA sequence.

We have found that a two stage PCR technique targeted to regions of HIV known to be associated with drug resistance coupled with a novel pyrophosphate sequencing technique would allow the detection of low frequency HIV sequence variants (SNPs, indels and other DNA polymorphisms) in a rapid, reliable, and cost effective manner. Furthermore, the method of the invention can detect sequence variants which are present in a HIV sample in nonstoichmetric allele amounts, such as, for example, HIV variants present in less than 50%, less than 25%, less than 10%, less than 5% or less than 1%. The techniques may conveniently be termed "ultradeep sequencing."

According to the present invention there is provided a method for diagnosing a sequence variant (such as an allelic frequency, SNP frequency, indel frequency) by specific amplification and sequencing of multiple alleles in a nucleic acid sample. The nucleic acid is first subjected to amplification by a pair of PCR primers designed to amplify a region surrounding the region of interest that includes regions known to be associated with HIV drug resistance. Each of the products of the PCR reaction (amplicons) is subsequently further amplified individually in separate reaction vessels using EBCA (Emulsion Based Clonal Amplification). EBCA amplicons (referred to herein as second amplicons) are sequenced and the collection of sequences, from different emulsion PCR amplicons, is used to determine an allelic frequency.

In one embodiment of the invention a method for detecting low frequency occurrence of one or more HIV sequence variants associated with drug resistance is describe that comprises the steps of generating a plurality of cDNA species from each RNA molecule in an HIV sample population; amplifying a plurality of first amplicons from the cDNA species, wherein each first amplicon comprises a plurality of amplified copies and is amplified with a pair of nucleic acid primers that define a locus of the first amplicon; clonally amplifying the amplified copies of the first amplicons to produce a plurality of second amplicons wherein a plurality of the second amplicons comprise an immobilized population of substantially identical copies from one of the amplified copies of first amplicons; determining a nucleic acid sequence composition of the substantially identical copies from at least 100 of the immobilized populations in parallel on a single instrument; detecting one or more sequence variants that occur at a frequency of 5% or less in the nucleic acid sequence composition of the at least 100 immobilized populations; and correlating the detected sequence variants with variation associated with HIV drug resistance.

BRIEF DESCRIPTION OF THE FIGURES

FIG. 4 discloses SEQ ID NOS 135-137, respectively, in order of appearance.

FIGS. 5A and 5B disclose SEQ ID NO: 138.

FIG. 15 discloses SEQ ID NOS 132 and 139-156, respectively, in order of appearance.

FIG. 16 discloses SEQ ID NOS 157-177, respectively, in order of appearance.

FIG. 17 discloses SEQ ID NOS 178-202, respectively, in order of appearance.

FIG. 18 depicts a nucleotide sequence alignment between HIV Glade B (SEQ ID NO: 133) and Glade C (SEQ ID NO: 134) sequences.

DETAILED DESCRIPTION OF THE INVENTION

Figure 1A:
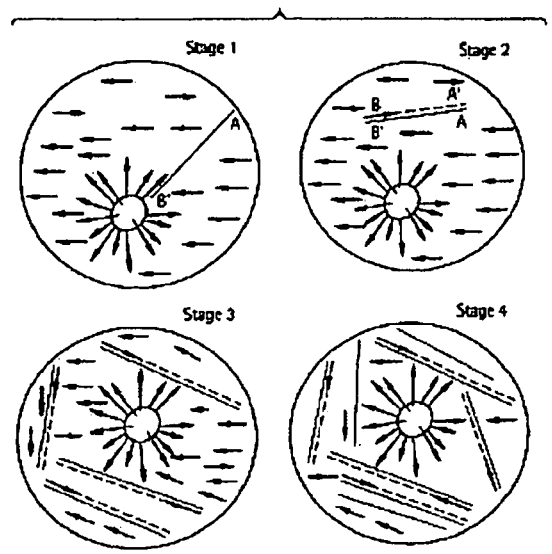
FIG. 1 depicts a schematic of one embodiment of a bead emulsion amplification process.

The invention relates to methods of highly sensitive detection of one or more sequence variants specific to HIV drug resistant strains by the identification of sequence composition of thousands of specific nucleic acids in a sample population. Sequence variants encompass any sequence differences between two nucleic acid molecules. As such, sequence variants is understood to also refer to, at least, single nucleotide polymorphisms, insertion/deletions (indels), allelic frequencies and nucleotide frequencies—that is, these terms are interchangeable. While different detection techniques are discussed throughout this specification using specific examples, it is understood that the process of the invention is equally applicable to the detection of any sequence variants. For example, a discussion of a process for detecting SNPs in this disclosure is also applicable to a process for detecting indels or nucleotide frequencies.

This process of the invention may be used to amplify and sequence specific targeted templates such as those found within genomes, tissue samples, heterogeneous cell populations or environmental samples. These can include, for example, PCR products, candidate genes, mutational hot spots, evolutionary or medically important variable regions. It could also be used for applications such as whole genome amplification with subsequent whole genome sequencing by using variable or degenerate amplification primers.

To date, sequencing targeted templates have required preparation and sequencing entire genomes of interest or prior PCR amplification of a region of interest and the sequencing of that region. The methods of the invention allow SNP sequencing to be performed at substantially greater depth than currently provided by existing technology.

In this disclosure, "single nucleotide polymorphism" ("SNP") may be defined as a SNP that exists in at least two variants where the least common variant is present in at least 1% of the population (Wang et al., 1998 Science 280:1077-1082). Variation that occurs at less than 1% in a population is typically referred to as a "mutation". It is understood that the methods of the disclosure may be applied to "indels." Therefore, while the instant disclosure makes references to SNP, it is understood that this disclosure is equally applicable if the term "SNP" is substituted with the term "indel" at any location.

As used herein, the term "indel" is intended to mean the presence of an insertion or a deletion of one or more nucleotides within a nucleic acid sequence compared to a related nucleic acid sequence. An insertion or a deletion therefore includes the presence or absence of a unique nucleotide or nucleotides in one nucleic acid sequence compared to an otherwise identical nucleic acid sequence at adjacent nucleotide positions. Insertions and deletions can include, for example, a single nucleotide, a few nucleotides or many nucleotides, including 5, 10, 20, 50, 100 or more nucleotides at any particular position compared to the related reference sequence. It is understood that the term also includes more than one insertion or deletion within a nucleic acid sequence compared to a related sequence.

Recent developments in nucleic acid sequencing technologies have dramatically increased throughput by sequencing many target nucleic acid molecules in parallel at a greatly reduced cost over previous technologies. These developments have enabled highly sensitive detection of the presently described invention and may be performed using instrumentation that automates one or more steps or operations associated with the preparation and/or sequencing methods. For instance, some instruments employ reaction substrate elements such as plates with wells or other type of multi-chambered configuration that provide the ability to perform reactions in each of the wells or chambers simultaneously. In some embodiments, the reaction substrate for sequencing may include what is referred to as a PicoTiterPlate® array (also referred to as a PTP® plate) formed from a fiber optics faceplate that is acid-etched to yield hundreds of thousands of very small wells each enabled to hold a population of substantially identical template molecules. Examples of high throughput sequencing techniques as well as systems and methods for massively parallel sequencing are described in U.S. Pat. Nos. 6,274,320; 6,258,568; 6,210,891; 7,211,390; 7,244,559; and 7,323,305, each of which is incorporated by reference herein in its entirety for all purposes; and U.S. patent application Ser. Nos. 10/299,180; 10/222,298; 10/222,592; and 11/195,254, each of which is incorporated by reference herein in its entirety for all purposes.

As described above, sequencing many nucleic acid templates in parallel provides the sensitivity necessary for the presently described invention. For example, Poisson statistics indicates that the lower limit of detection (i.e., less than one event) for a fully loaded 60 mm×60 mm PTP plate ($2 \times 10^6$ high quality bases, comprised of 200,000×100 base reads) is three events with a 95% confidence of detection and five events with a 99% confidence of detection (see Table 1). This scales directly with the number of reads, so the same limits of detection hold for three or five events in 10,000 reads, 1000 reads, or 100 reads. The term "read" as used herein generally refers to the data comprising the sequence composition obtained from a single nucleic acid template molecule or a population of a plurality of substantially identical copies of the template nucleic acid molecule. Since the actual amount of DNA read is higher than the 200,000 number provided in the example above, the actual lower limit of detection is expected to be at an even lower point due to the increased sensitivity of the assay. For comparison, SNP detection via pyrophosphate based sequencing has reported detection of separate allelic states on a tetraploid genome, so long as the ratio least frequent allele is present in 10% or more of the population (Rickert et al., 2002 BioTechniques. 32:592-603). Conventional fluorescent DNA sequencing is even less sensitive, experiencing trouble resolving 50/50 (i.e., 50%) heterozygote alleles (Ahmadian et al., 2000 Anal. BioChem. 280:103-110).

TABLE 1

Probability of detecting zero or one or more events, based on number of events in total population.

| Copies of Sequence | Percent chance of detecting zero copies | Percent chance of detecting one or more copies |
|---|---|---|
| 1 | 36.8 | 63.2 |
| 2 | 13.5 | 86.5 |
| 3 | 5.0* | 95.0* |
| 4 | 1.8 | 98.2 |
| 5 | 0.7** | 99.3** |
| 6 | 0.2 | 99.8 |
| 7 | 0.1 | 99.9 |
| 8 | 0.0 | 100.0 |
| 9 | 0.0 | 100.0 |
| 10 | 0.0 | 100.0 |

"*" indicates that probability of failing to detect three events is 5.0%, thus the probability of detecting said event is 95%; similarly,
"**" reveals that that probability of detecting one or more events that occur 5 times is 99.3%.

As a result, utilizing an entire 60×60 mm PTP plate to detect a single variant permits detection of a variant present in only 0.002% of the population with a 95% confidence or in 0.003% of the population with 99% confidence. Naturally, multiplex analysis is of greater applicability than this depth of detection and Table 2 displays the number of variants that can be screened simultaneously on a single PTP plate, with the minimum allelic frequencies detectable at 95% and 99% confidence.

TABLE 2

| Variant Classes | Number of Reads | Frequency of variant in population with 95% confidence | Frequency of variant in population with 99% confidence |
|---|---|---|---|
| 1 | 200000 | 0.002% | 0.003% |
| 2 | 10000 | 0.030% | 0.050% |
| 5 | 4000 | 0.075% | 0.125% |
| 10 | 2000 | 0.15% | 0.25% |
| 50 | 400 | 0.75% | 1.25% |
| 100 | 200 | 1.50% | 2.5% |
| 150 | 133 | 2.25% | 3.75% |
| 200 | 100 | 3.0% | 5.0% |
| 500 | 40 | 7.5% | 12.5% |
| 1000 | 20 | 15.0% | 25.0% |

One advantage of the invention, is that a number of steps, usually associated with sample preparation (e.g., extracting and isolating DNA from tissue for sequencing) may be eliminated or simplified. For example, because of the sensitivity of the method, it is no longer necessary to extract DNA from tissue using traditional technique of grinding tissue and chemical purification. Instead, a small tissue sample of less than one microliter in volume may be boiled and used for the first PCR amplification. The product of this solution amplification is added directly to the emPCR reaction. The methods of the invention therefore reduce the time and effort and product loss (including loss due to human error).

Another advantage of the methods of the invention is that the method is highly amenable to multiplexing. As discussed below, the bipartite primers of the invention allows combining primer sets for multiple genes with identical pyrophosphate sequencing primer sets in a single solution amplification. Alternatively, the product of multiple preparations may be placed in a single emulsion PCR reaction. As a result, the methods of the invention exhibit considerable potential for high throughput applications.

One embodiment of the invention is directed to a method for determining an allelic frequency (including SNP and indel frequency) of HIV drug resistant variants. In the first step, cDNA molecules are generated using HIV RNA from a patient (also referred to as a "subject") as a template. Next, a first population of amplicons is produced by PCR using one or more sets of target specific primers to amplify one or more populations of nucleic acids comprising the loci to be analyzed. Each locus may comprise a plurality of alleles such as, for example, 2, 4, 10, 15 or 20 or more alleles. The first amplicons may be of any size, such as, for example, between 50 and 100 bp, between 100 by and 200 bp, or between 200 by to 1 kb. One advantage of the method is that knowledge of the nucleic acid sequence between the two primers is not required.

In the subsequent step, the population of first amplicons is delivered into aqueous microreactors in a water-in-oil emulsion such that a plurality of aqueous microreactors comprises (1) sufficient DNA to initiate an amplification reaction dominated by a single template or amplicon (2) a single bead, and (3) amplification reaction solution containing reagents necessary to perform nucleic acid amplification (See discussion regarding EBCA (Emulsion Based Clonal Amplification) below). We have found that an amplification reaction dominated by a single template or amplicon may be achieved even if two or more templates are present in the microreactor. Therefore, aqueous microreactors comprising more than one template are also envisioned by the invention. In a preferred embodiment, each aqueous microreactor has a single copy of DNA template for amplification.

After the delivery step, the first population of amplicons is amplified in the microreactors to form second amplicons. Amplification may be performed, for example, using EBCA (which involves PCR) in a thermocycler to produce second amplicons. After EBCA, the second amplicons are bound to the beads in the microreactors. The beads, with bound second amplicons are delivered to an array of reaction chambers (e.g., an array of at least 10,000 reaction chambers) on a planar surface. The delivery is adjusted such that a plurality of the reaction chambers comprise no more than a single bead. This may be accomplished, for example, by using an array where the reaction chambers are sufficiently small to accommodate only a single bead.

A sequencing reaction is performed simultaneously on the plurality of reaction chambers to determine a plurality of nucleic acid sequences corresponding to said plurality of alleles. Methods of parallel sequencing in parallel using reaction chambers are disclosed in another section above and in the Examples. Following sequencing, the allelic frequency, for at least two alleles, may be determined by analyzing the sequences from the target population of nucleic acids. As an example, if 10000 sequences are determined and 9900 sequences read "aaa" while 100 sequences read "aag," the "aaa" allele may be said to have a frequency of 90% while the "aag" allele would have a frequency of 10%. This is described in more detail in the description below and in the Examples.

One advantage of the invention's methods is that it allows a higher level of sensitivity for HIV sequence variation than previously achieved. If a PTP plate is used, the methods of the invention can sequence over 100,000 or over 300,000 different copies of an allele per picotiter plate. The sensitivity of detection allows detection of low abundance alleles which may represent 1% or less of the allelic variants in a subject sample. Another advantage of the invention's methods is that the sequencing reaction also provides the sequence composition of the analyzed region. That is, it is not necessary to have prior knowledge of the sequence of the locus being analyzed.

In a preferred embodiment, the methods of the invention may detect an allelic frequency which is less than 10%, less than 5%, or less than 2%. In a more preferred embodiment, the method may detect allelic frequencies of less than 1%, such as less than 0.5% or less than 0.2%. Typical ranges of detection sensitive may be between 0.1% and 100%, between 0.1% and 50%, between 0.1% and 10% such as between 0.2% and 5%.

In various embodiments, the target population of nucleic acids may be from a number of sources. For example, the source of HIV sample may be a tissue or body fluid from a patient/subject, or other organism susceptible to HIV infection. Also, sources of other sample types may include any organism including mammals. The mammals may be a human or commercially valuable livestock such as cows, sheep, pigs, goats, rabbits, and the like. The described methods also allow analysis tissue and fluid samples of plants. While all plants may be analyzed by the described methods, preferred plants include commercially valuable crop species including monocots and dicots. In one particular embodiment, the target population of nucleic acids may be derived from a grain or food product to determine the original and distribution of genotypes, alleles, or species that make up the grain or food product. Such crops include, for example, maize, sweet corn, squash, melon, cucumber, sugarbeet, sunflower, rice, cotton, canola, sweet potato, bean, cowpea, tobacco, soybean, alfalfa, wheat, or the like.

Also in some embodiments, nucleic acid samples may be collected from multiple organisms. For example, allelic frequency of a population of 1000 individuals may be performed in one experiment analyzing a mixed DNA sample from 1000 individuals. Naturally, for a mixed DNA sample to be representative of the allelic frequency of a population, each member of the population (each individual) must contribute the same (or approximately the same) amount of nucleic acid (same number of copies of an allele) to the pooled sample. For example, in an analysis of genomic allelic frequency, each individual may contribute the DNA from approximately $1.0 \times 10^6$ cells to a pooled DNA sample.

In another embodiment, the polymorphism in a single individual may be determined. That is the target nucleic acid may be isolated from a single individual. For example, pooled nucleic acids from multiple tissue sample of an individual may be examined for polymorphisms and nucleotide frequencies. This may be useful, for example, for determining polymorphism in a tumor, or a tissue suspected to contain a tumor, of an individual. The method of the invention may be used, for example, to determine the frequency of an activated oncogene in a tissue sample (or pooled DNA from multiple tissue sample) of an individual. In this example, an allelic frequency of 50% or more of activated oncogenes may indicate that the tumor is monoclonal. The presence of less than 50% of an activated oncogene may indicate that the tumor is polyclonal, or that the tissue sample contains a combination of tumor tissue and normal (non-tumor) tissue. Furthermore, in a biopsy of a suspect tissue, the presence of, for example, 1% of an activated oncogene may indicate the presence of an emerging tumor, or the presence of a malignant tumor infiltration.

The target population of nucleic acids may be any nucleic acid including DNA, RNA and various forms of such DNA and RNAs such as plasmids, cosmids, DNA viral genomes, RNA viral genome, bacterial genomes, mitochondrial DNA, mammalian genomes, plant genomes. The nucleic acid may be isolated from a tissue sample or from an in vitro culture. Genomic DNA can be isolated from a tissue sample, a whole organism, or a sample of cells. If desired, the target population of nucleic acid may be normalized such that it contains an equal amount of alleles from each individual that contributed to the population.

One advantage of the invention is that the genomic DNA may be used directly without further processing. However, in a preferred embodiment, the genomic DNA may be substantially free of proteins that interfere with PCR or hybridization processes, and are also substantially free of proteins that damage DNA, such as nucleases. Preferably, the isolated genomes are also free of non-protein inhibitors of polymerase function (e.g. heavy metals) and non-protein inhibitors of hybridization which would interfere with a PCR. Proteins may be removed from the isolated genomes by many methods known in the art. For instance, proteins may be removed using a protease, such as proteinase K or pronase, by using a strong detergent such as sodium dodecyl sulfate (SDS) or sodium lauryl sarcosinate (SLS) to lyse the cells from which the isolated genomes are obtained, or both. Lysed cells may be extracted with phenol and chloroform to produce an aqueous phase containing nucleic acid, including the isolated genomes, which can be precipitated with ethanol.

The target population of nucleic acid may be derived from sources with unknown origins of DNA such as soil samples, food samples and the like. For example, the sequencing of an allele found in a pathogen in a nucleic acid sample from a food sample would allow the determination the presence of pathogen contamination in the food. Furthermore, the methods of the invention would allow determination of the distribution of pathogenic allele in the food. For example, the methods of the invention can determine the strain (species) or distribution of strains (species) of a particular organism (e.g., bacteria, virus, pathogens) in an environmental sample such as a soil sample (See, Example 5) or a seawater sample.

One advantage of the method is that no a priori knowledge of variation is required for the method. Because the method is based on nucleic acid sequencing, all variation in one location would be detected. Furthermore, no cloning is required for the sequencing. A DNA sample is amplified in sequenced in a series of steps without the need for cloning, subcloning, and culturing of the cloned DNA.

The aspects described above for detection of low frequency variation are particularly useful in this context of the presently described invention. For example as described in greater detail below, the invention provides for detection and quantification of all HIV variants associated with drug resistance, and particularly variants that occur at a low frequency in viral samples. These viral samples may, in the present example, include an HIV viral isolate. In some preferred embodiments of the presently described invention the "target population", "sample population", or "subject population" may be derived from an HIV RNA source comprising a detectable titer of virus. In typical embodiments, the source may include a sample from a human subject that includes collected tissue or fluid samples from an HIV infected patient that may or may not have been exposed to a drug treatment regimen (i.e. the patient may or may not be "drug naïve"). Also, the methods of the invention as described herein can determine if variation is present in the reverse transcriptase and/or protease regions at a low frequency in the sample, where the variations may be correlated with known drug resistance or newly identified resistant strains. The methods also provide a measure of frequency of each of the variants in a sample population that can be employed to determine or alter a therapeutic regimen that may include avoidance of one or more drugs, drug classes, or drug combinations that will have little therapeutic benefit due to resistance conffered by the identified HIV variant strain(s).

Other applications of the described methods include population studies of sequence variants. DNA samples may be collected from a population of organisms and combined and analyzed in one experiment to determine allelic frequencies. The populations of organisms may include, for example, a population of humans, a population of livestock, a population of grain from a harvest and the like. Other uses include detection and quantification of somatic mutations in tumor biopsies (e.g. lung and colorectal cancer) from biopsy comprising a mixed population of tumor and normal cells. The methods of the invention may also be used for high confidence re-sequencing of clinically relevant susceptibility genes (e.g. breast, ovarian, colorectal and pancreatic cancer, melanoma).

Another use for the described methods involves identification of polymorphisms associated with a plurality of distinct genomes. The distinct genomes may be isolated from populations which are related by some phenotypic characteristic, familial origin, physical proximity, race, class, etc. In other cases, the genomes are selected at random from populations such that they have no relation to one another other than being selected from the same population. In one preferred embodiment, the method is performed to determine the genotype (e.g. SNP content) of subjects having a specific phenotypic characteristic, such as a genetic disease or other trait.

The described methods may also be used to characterize the genetic makeup of a tumor by testing for loss of heterozygosity or to determine the allelic frequency of a particular SNP. Additionally, the methods may be used to generate a genomic classification code for a genome by identifying the presence or absence of each of a panel of SNPs in the genome and to determine the allelic frequency of the SNPs. Each of these uses is discussed in more detail herein.

A preferred use of the invention is in a high throughput method of genotyping. "Genotyping" is the process of identifying the presence or absence of specific genomic sequences within genomic DNA. Distinct genomes may be isolated from individuals of populations which are related by some phenotypic characteristic, by familial origin, by physical proximity, by race, by class, etc. in order to identify polymorphisms (e.g. ones associated with a plurality of distinct genomes) which are correlated with the phenotype family, location, race, class, etc. Alternatively, distinct genomes may be isolated at random from populations such that they have no relation to one another other than their origin in the population. Identification of polymorphisms in such genomes indicates the presence or absence of the polymorphisms in the population as a whole, but not necessarily correlated with a particular phenotype. Since a genome may span a long region of DNA and may involve multiple chromosomes, a method of the invention for detecting a genotype would need to analyze a plurality of sequence variants at multiple locations to detect a genotype at a reliability of 99.99%.

Although genotyping is often used to identify a polymorphism associated with a particular phenotypic trait, this correlation is not necessary. Genotyping only requires that a polymorphism, which may or may not reside in a coding region, is present. When genotyping is used to identify a phenotypic characteristic, it is presumed that the polymorphism affects the phenotypic trait being characterized. A phenotype may be desirable, detrimental, or, in some cases, neutral. Polymorphisms identified according to the methods of the invention can contribute to a phenotype. Some polymorphisms occur within a protein coding sequence and thus can affect the protein structure, thereby causing or contributing to an observed phenotype. Other polymorphisms occur outside of the protein coding sequence but affect the expression of the gene. Still other polymorphisms merely occur near genes of interest and are useful as markers of that gene. A single polymorphism can cause or contribute to more than one phenotypic characteristic and, likewise, a single phenotypic characteristic may be due to more than one polymorphism. In general multiple polymorphisms occurring within a gene correlate with the same phenotype. Additionally, whether an individual is heterozygous or homozygous for a particular polymorphism can affect the presence or absence of a particular phenotypic trait.

Phenotypic correlation is performed by identifying an experimental population of subjects exhibiting a phenotypic characteristic and a control population which do not exhibit that phenotypic characteristic. Polymorphisms which occur within the experimental population of subjects sharing a phenotypic characteristic and which do not occur in the control population are said to be polymorphisms which are correlated with a phenotypic trait. Once a polymorphism has been identified as being correlated with a phenotypic trait, genomes of subjects which have potential to develop a phenotypic trait or characteristic can be screened to determine occurrence or non-occurrence of the polymorphism in the subjects' genomes in order to establish whether those subjects are likely to eventually develop the phenotypic characteristic. These types of analyses are may be performed on subjects at risk of developing a particular disorder such as Huntington's disease or breast cancer.

One embodiment of the described methods is directed to a method for associating a phenotypic trait with an SNP. A phenotypic trait encompasses any type of genetic disease, condition, or characteristic, the presence or absence of which can be positively determined in a subject. Phenotypic traits that are genetic diseases or conditions include multifactorial diseases of which a component may be genetic (e.g. owing to occurrence in the subject of a SNP), and predisposition to such diseases. These diseases include such as, but not limited to, asthma, cancer, autoimmune diseases, inflammation, blindness, ulcers, heart or cardiovascular diseases, nervous system disorders, and susceptibility to infection by pathogenic microorganisms or viruses. Autoimmune diseases include, but are not limited to, rheumatoid arthritis, multiple sclerosis, diabetes, systemic lupus, erythematosus and Graves' disease. Cancers include, but are not limited to, cancers of the bladder, brain, breast, colon, esophagus, kidney, hematopoietic system e.g. leukemia, liver, lung, oral cavity, ovary, pancreas, prostate, skin, stomach, and uterus. A phenotypic trait may also include susceptibility to drug or other therapeutic treatments, appearance, height, color (e.g. of flowering plants), strength, speed (e.g. of race horses), hair color, etc. Many examples of phenotypic traits associated with genetic variation have been described, see e.g., U.S. Pat. No. 5,908,978 (which identifies association of disease resistance in certain species of plants associated with genetic variations) and U.S. Pat. No. 5,942,392 (which describes genetic markers associated with development of Alzheimer's disease).

Identification of associations between genetic variations (e.g. occurrence of SNPs) and phenotypic traits is useful for many purposes. For example, identification of a correlation between the presence of a SNP allele in a subject and the ultimate development by the subject of a disease is particularly useful for administering early treatments, or instituting lifestyle changes (e.g., reducing cholesterol or fatty foods in order to avoid cardiovascular disease in subjects having a greater-than-normal predisposition to such disease), or closely monitoring a patient for development of cancer or other disease. It may also be useful in prenatal screening to identify whether a fetus is afflicted with or is predisposed to develop a serious disease. Additionally, this type of information is useful for screening animals or plants bred for the purpose of enhancing or exhibiting of desired characteristics.

One method for determining a SNP or a plurality of SNPs associated with a plurality of genomes is screening for the presence or absence of a SNP in a plurality of genomic samples derived from organisms with the trait. In order to determine which SNPs are related to a particular phenotypic trait, genomic samples are isolated from a group of individuals which exhibit the particular phenotypic trait, and the samples are analyzed for the presence of common SNPs. The genomic sample obtained from each individual may be combined to form a pooled genomic sample. Then the methods of the invention are used to determine an allelic frequency for each SNP. The pooled genomic sample is screened using panels of SNPs in a high throughput method of the invention to determine whether the presence or absence of a particular SNP (allele) is associated with the phenotype. In some cases, it may be possible to predict the likelihood that a particular subject will exhibit the related phenotype. If a particular polymorphic allele is present in 30% of individuals who develop Alzheimer's disease but only in 1% of the population, then an individual having that allele has a higher likelihood of developing Alzheimer's disease. The likelihood can also depend on several factors such as whether individuals not afflicted with Alzheimer's disease have this allele and whether other factors are associated with the development of Alzheimer's disease. This type of analysis can be useful for determining a probability that a particular phenotype will be exhibited. In order to increase the predictive ability of this type of analysis, multiple SNPs associated with a particular phenotype can be analyzed and the correlation values identified.

It is also possible to identify SNPs which segregate with a particular disease. Multiple polymorphic sites may be detected and examined to identify a physical linkage between them or between a marker (SNP) and a phenotype. This may be used to map a genetic locus linked to or associated with a phenotypic trait to a chromosomal position and thereby revealing one or more genes associated with the phenotypic trait. If two polymorphic sites segregate randomly, then they are either on separate chromosomes or are distant enough, with respect to one another on the same chromosome that they do not co-segregate. If two sites co-segregate with significant frequency, then they are linked to one another on the same chromosome. These types of linkage analyses are useful for developing genetic maps which may define regions of the genome important for a phenotype—including a disease genotype.

Linkage analysis may be performed on family members who exhibit high rates of a particular phenotype or a particular disease. Biological samples are isolated from family members exhibiting a phenotypic trait, as well as from subjects which do not exhibit the phenotypic trait. These samples are each used to generate individual SNPs allelic frequencies. The data can be analyzed to determine whether the various SNPs are associated with the phenotypic trait and whether or not any SNPs segregate with the phenotypic trait.

Methods for analyzing linkage data have been described in many references, including Thompson & Thompson, Genetics in Medicine (5th edition), W.B. Saunders Co., Philadelphia, 1991; and Strachan, "Mapping the Human Genome" in the Human Genome (Bios Scientific Publishers Ltd., Oxford) chapter 4, and summarized in PCT published patent application WO98/18967 by Affymetrix, Inc. Linkage analysis involving by calculating log of the odds values (LOD values) reveals the likelihood of linkage between a marker and a genetic locus at a recombination fraction, compared to the value when the marker and genetic locus are not linked. The recombination fraction indicates the likelihood that markers are linked. Computer programs and mathematical tables have been developed for calculating LOD scores of different recombination fraction values and determining the recombination fraction based on a particular LOD score, respectively. See e.g., Lathrop, PNAS, USA 81, 3443-3446 (1984); Smith et al., Mathematical Tables for Research Workers in Human Genetics (Churchill, London, 1961); Smith, Ann. Hum. Genet. 32, 127-1500 (1968). Use of LOD values for genetic mapping of phenotypic traits is described in PCT published patent application WO98/18967 by Affymetrix, Inc. In general, a positive LOD score value indicates that two genetic loci are linked and a LOD score of +3 or greater is strong evidence that two loci are linked. A negative value suggests that the linkage is less likely.

The methods of the invention are also useful for assessing loss of heterozygosity in a tumor. Loss of heterozygosity in a tumor is useful for determining the status of the tumor, such as whether the tumor is an aggressive, metastatic tumor. The method is can be performed by isolating genomic DNA from tumor sample obtained from a plurality of subjects having tumors of the same type, as well as from normal (i.e., non-cancerous) tissue obtained from the same subjects. These genomic DNA samples are used to for the SNP detection method of the invention. The absence of a SNP allele from the tumor compared to the SNP alleles generated from normal tissue indicates whether loss of heterozygosity has occurred. If a SNP allele is associated with a metastatic state of a cancer, the absence of the SNP allele can be compared to its presence or absence in a non-metastatic tumor sample or a normal tissue sample. A database of SNPs which occur in normal and tumor tissues can be generated and an occurrence of SNPs in a patient's sample can be compared with the database for diagnostic or prognostic purposes.

It is useful to be able to differentiate non-metastatic primary tumors from metastatic tumors, because metastasis is a major cause of treatment failure in cancer patients. If metastasis can be detected early, it can be treated aggressively in order to slow the progression of the disease. Metastasis is a complex process involving detachment of cells from a primary tumor, movement of the cells through the circulation, and eventual colonization of tumor cells at local or distant tissue sites. Additionally, it is desirable to be able to detect a predisposition for development of a particular cancer such that monitoring and early treatment may be initiated. Many cancers and tumors are associated with genetic alterations.

Solid tumors progress from tumorigenesis through a metastatic stage and into a stage at which several genetic aberrations can occur. e.g., Smith et al., Breast Cancer Res. Terat., 18 Suppl. 1, S5-14, 1991. Genetic aberrations are believed to alter the tumor such that it can, progress to the next stage, i.e., by conferring proliferative advantages, the ability to develop drug resistance or enhanced angiogenesis, proteolysis, or metastatic capacity. These genetic aberrations are referred to as "loss of heterozygosity." Loss of heterozygosity can be caused by a deletion or recombination resulting in a genetic mutation which plays a role in tumor progression. Loss of heterozygosity for tumor suppressor genes is believed to play a role in tumor progression. For instance, it is believed that mutations in the retinoblastoma tumor suppressor gene located in chromosome 13q14 causes progression of retinoblastomas, osteosarcomas, small cell lung cancer, and breast cancer. Likewise, the short arm of chromosome 3 has been shown to be associated with cancer such as small cell lung cancer, renal cancer and ovarian cancers. For instance, ulcerative colitis is a disease which is associated with increased risk of cancer presumably involving a multistep progression involving accumulated genetic changes (U.S. Pat. No. 5,814, 444). It has been shown that patients afflicted with long duration ulcerative colitis exhibit an increased risk of cancer, and that one early marker is loss of heterozygosity of a region of the distal short arm of chromosome 8. This region is the site of a putative tumor suppressor gene that may also be implicated in prostate and breast cancer. Loss of heterozygosity can easily be detected by performing the methods of the invention routinely on patients afflicted with ulcerative colitis. Similar analyses can be performed using samples obtained from other tumors known or believed to be associated with loss of heterozygosity. The methods of the invention are particularly advantageous for studying loss of heterozygosity because thousands of tumor samples can be screened at one time.

Embodiments of the described methods involve processing nucleic acids to determine an allelic frequency. The method may be broadly defined in the following three steps: (1) Sample preparation—preparation of the first amplicons; (2) bead emulsion PCR—preparation of the second amplicons. (3) sequencing by synthesis—determining multiple sequences from the second amplicons to determine an allelic frequency. Each of these steps is described in more detail below and in the Example section.

Preferred embodiments of the presently described invention include employing the method steps described immediately above using specifically designed primer sets that enable detection of both high- and low frequency mutations in samples containing multiple viral species of HIV. For example, detection of minor variants in HIV-1 Glade B and Glade C samples have hitherto been undetectable by conventional (dideoxynucleotide terminator) sequencing. These minor variants are important in cases where such mutations confer resistance to antiretroviral drugs. Using one or more of the primer sets and subsequent sequencing oversampling, both known and previously unidentified resistance mutations can be detected in a low-bias manner (i.e., the method is not focused entirely on known mutations and is not dependent on primers binding immediately next to positions of interest as most sensitive detection assays already developed). The term "sequencing oversampling" as used herein generally refers to a sequencing the same region (i.e. as in an amplicon region) from different sources (i.e. different viral particles) at a frequency that provides a highly sensitive level of detection of sequence variants in a sample population for that region.

In some embodiments; the presently described primer sets may be employed in highly sensitive sequencing methods, such the target specific amplicon (also referred to as "ultradeep") methods described above capable of achieving sensitivity to detect sequence variants that occur with a frequency of less than 1% of a population. In some cases the sensitivity is capable of detecting 0.01% frequency in a population.

In the presently described invention, the primer sets were designed using an alignment of many known HIV sequences by methods known to those of ordinary skill in the related art. For example, numerous sequence alignment methods, algorithms, and applications are available in the art including but not limited to the Smith-Waterman algorithm (Smith T F, Waterman M S (1981). "Identification of Common Molecular Subsequences". *Journal of Molecular Biology* 147: 195-197, which is incorporated by reference herein in its entirety for all purposes), BLAST algorithm (Altschul, S. F., Gish, W., Miller, W., Myers, E. W. & Lipman, D. J. (1990) "Basic local alignment search tool." J. Mol. Biol. 215:403-410, which is incorporated by reference herein in its entirety for all purposes), and Clustal (Thompson J D, Gibson T J, Plewniak F, Jeanmougin F, Higgins D G (1997). The ClustalX windows interface: flexible strategies for multiple sequence alignment aided by quality analysis tools. *Nucleic Acids Research*, 25:4876-4882, which is incorporated by reference herein in its entirety for all purposes). In the present example, any one of the alignment algorithms described above may be used to perform a multiple alignment of sequences from the same general sequence region. Such sequences are generally available in various public resources such as the well known GenBank database, or in the present case of HIV the sequences may be obtained from the HIV sequence database maintained at the Los Alamos National Laboratory. Also in the present example, sequences in the HIV POL region associated with any Glade may be specifically selected for alignments. As those of ordinary skill in the related art will appreciate HIV has tremendous genetic diversity where infections may be associated with a particular Glade of virus (also referred to as a subtype). Currently there are 9 identified clades designated by letters A-K, where certain Glade types are associated with specific geographical areas. For instance, HIV Glade B is generally found in North America and Europe while Glade C is generally found in South Africa and India.

Figure 9:
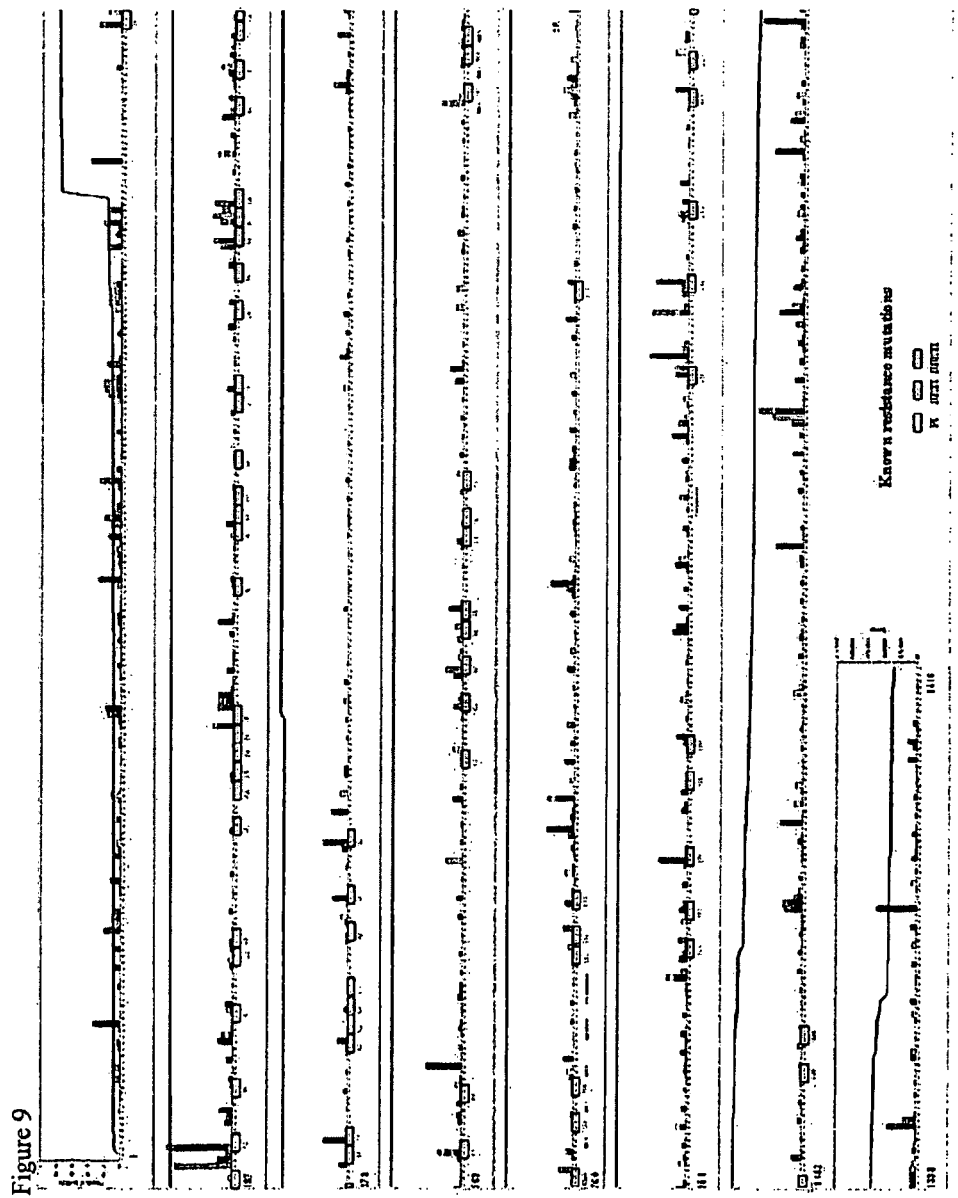
FIG. 9 depicts one embodiment of HIV-1 Clade B consensus sequence (SEQ ID No: 133) and regions known to be susceptible to mutation.

FIG. 9 provides an illustration of one example of results from the alignment of over 6000 HIV Glade B sequences in the POL region. As illustrated in FIG. 9, the alignment of a population of thousands of different HIV sequences into a single "consensus" sequence provides a representation of the identity of the most frequent nucleic acid species at each sequence position of the population of HIV sequences as well as a measure of the degree of variability or mutation frequency at each position. Such measures of mutation frequency are represented in the example of FIG. 9 as bars rising above the sequence representation and are associated with a specific sequence position(s). Also, the bars may also include other graphical identifiers for certain characteristics such as color (or other graphical representation such as hash marks, etc.) to represent other characteristics such as mutation frequency by clade and also the height of the bar represents degree of the measure of frequency. FIG. 9 also illustrates regions of interest that are known to be susceptible to mutation associated with drug resistance using small boxes positioned underneath the consensus sequence to represent the region of the sequence where, again, the color of the box may represent additional information such as drug classes or specific drugs of interest. Such drug classes and therapies may include, but are not limited to, highly active anti-retroviral therapy (also referred to as HAART); protease inhibitor (also referred to as PI); nucleotide/nucleoside reverse transcriptase inhibitor (also referred to as NRTI); and non-nucleoside reverse transcriptase inhibitor (NNRTI).

Figure 10:
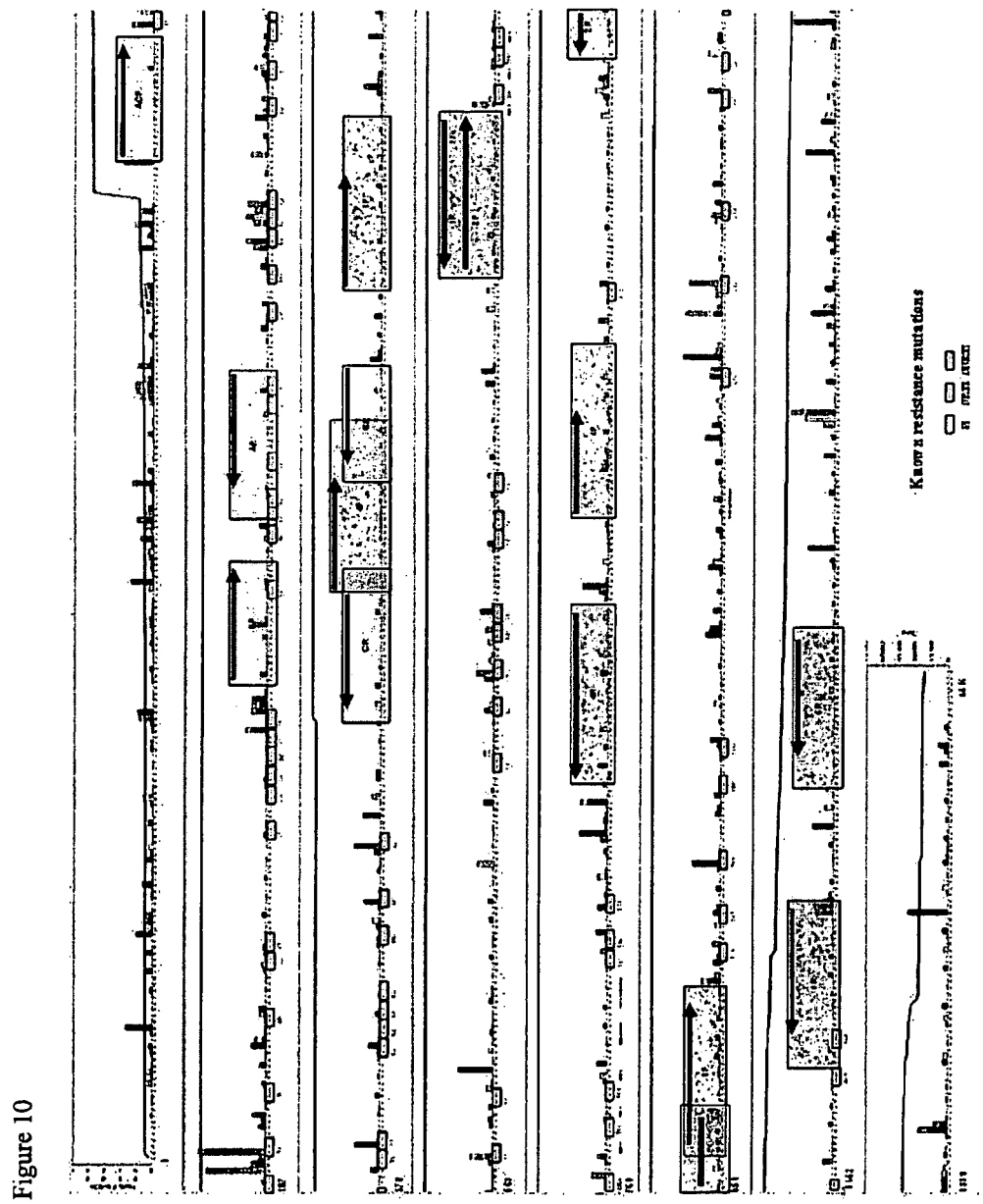
FIG. 10 depicts one embodiment of the Clade B sequence of FIG. 9 (SEQ ID NO: 133) and areas of the sequence targeted for design of sets of Clade B primers.

Primer sets were then designed to regions of the consensus sequence of FIG. 9 that are more conserved (i.e. less likely to mutate) than the regions of known mutation susceptibility. The advantage of targeting sequence regions with a low mutation rate for primer design includes the ability to reliably use the designed primers without substantial risk of failure due to mutation at the target region that would render the primer unable to bind, as well as the possibility of using the same primer sets for multiple clades. FIG. 10 provides an illustrative example of regions selected for primer design that interrogate Glade B sequences illustrated as the shaded boxes with directional arrows (indicating relative directionality of primer designed).

Examples of the designed Glade B primers illustrated in FIG. 10 include:

| Name | Sequence | SEQ ID No: | Length |
|---|---|---|---|
| B-BF | GCCTCCCTCGCGCCATCAGTGCCAGGAAGATGGAAACCA | 35 | 39 |
| B-AR | GCCTTGCCAGCCCGCTCAGTGATAAAACCTCCAATTCCCCCTA | 36 | 43 |
| B-CR | GCCTTGCCAGCCCGCTCAGGTACAGTTTCAATAGGACTAATGGG | 37 | 44 |
| B-BR | GCCTTGCCAGCCCGCTCAGTTGGGCCATCCATTCCTGG | 38 | 38 |
| B-ACF-1 | GCCTCCCTCGCGCCATCAGATCACTCTTTGGCAACGACC | 39 | 39 |
| B-ACF-2 | GCCTCCCTCGCGCCATCAGATCACTCTTTGGCAGCGACC | 40 | 39 |
| B-4F | GCCTCCCTCGCGCCATCAGGTACCAGTAAAATTAAAGCCAGGAATGG | 41 | 47 |
| B-1F | GCCTCCCTCGCGCCATCAGGGCCATTGACAGAAGAAAAAATAAAAGC | 42 | 47 |
| B-2F | GCCTCCCTCGCGCCATCAGGGAAGTTCAATTAGGAATACCACATCC | 43 | 46 |
| B-1R-1 | GCCTTGCCAGCCCGCTCAGGGATGTGGTATTCCTAATTGAACTTCC | 44 | 46 |

| Name | Sequence | SEQ ID No | Length |
|---|---|---|---|
| B-1R-2 | GCCTTGCCAGCCCGCTCAGGGATGTGGTATTCCTAATTGGACTTCC | 45 | 46 |
| B-4R-1 | GCCTTGCCAGCCCGCTCAGCTAGGTATGGTAAATGCAGTATACTTCCT | 46 | 48 |
| B-4R-2 | GCCTTGCCAGCCCGCTCAGCTAGGTATGGTAAATGCAGTATACTTTCT | 47 | 48 |
| B-5F | GCCTCCCTCGCGCCATCAGCACCAGGGATTAGATATCAGTACAATGT | 48 | 47 |
| B-2R | GCCTTGCCAGCCCGCTCAGAAGGCTCTAAGATTTTTGTCAT | 49 | 41 |
| B-3F | GCCTCCCTCGCGCCATCAGAGAGCCTTTTAGAAAACAAAATCCAGA | 50 | 46 |
| B-3R | GCCTTGCCAGCCCGCTCAGCACTATAGGCTGTACTGTCCATTTATC | 51 | 46 |
| B-5R-1 | GCCTTGCCAGCCCGCTCAGAACTTCTGTATGTCATTGACAGTCCA | 52 | 45 |
| B-5R-2 | GCCTTGCCAGCCCGCTCAGAACTTCTGTATATCATTGACAGTCCA | 53 | 45 |

All primers listed in 5'-3' orientation. Also, it will be appreciated that a certain primer in a set may have more than one species, due to sequence degeneracy at one or more sequence positons. For example, B-ACF-1 and B-ACF-2 represent to species of the ACF primer represented in FIG. 10 that differ from each other by a A to G nucleotide species difference at the same base position in the primer sequence.

Figure 11:
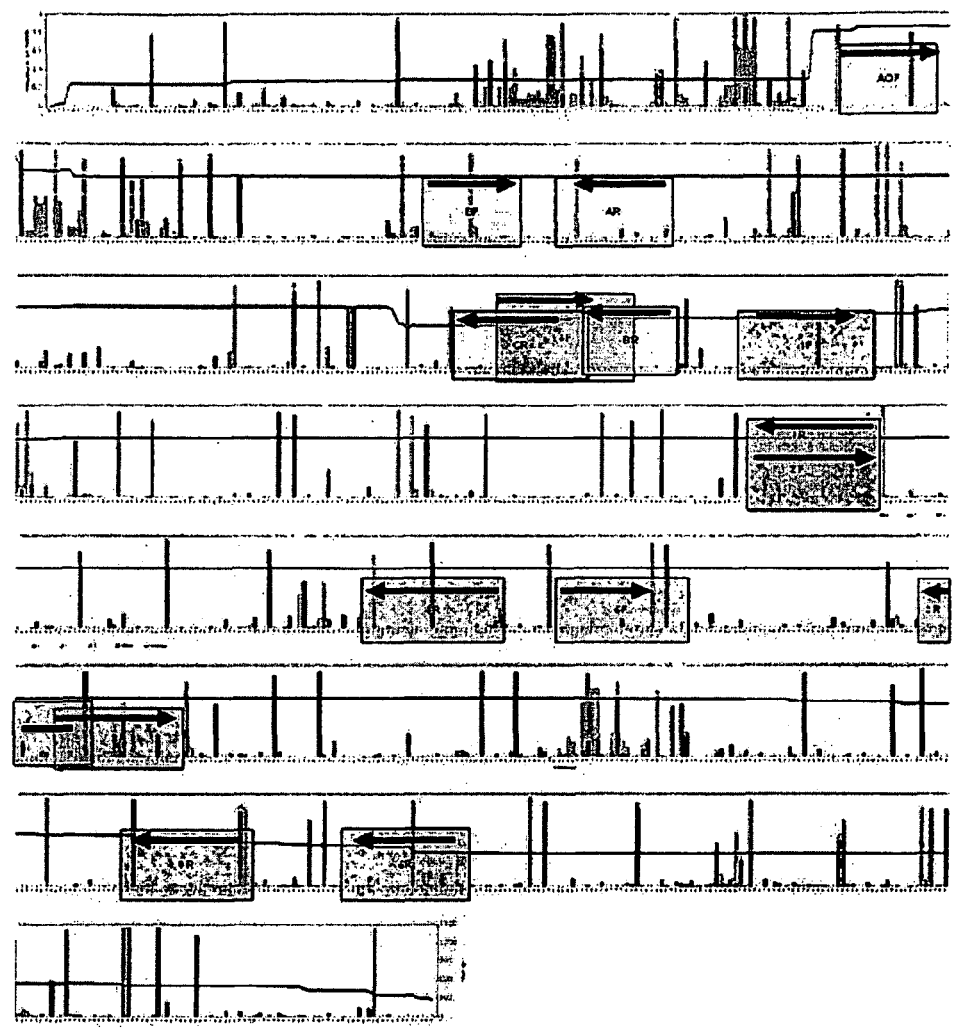
FIG. 11 depicts one embodiment of HIV-1 Clade B consensus sequence (SEQ ID NO: 133) comprising regions known to be susceptible to mutation and regions of the sequence targeted for design of sets of Clade C primers.

Further, FIG. 11 provides an illustrative example of the difference between Glade B and Glade C primers and demonstrates modified regions of Glade B primer design selected to interrogate Glade C sequences illustrated as the shaded boxes with directional arrows (indicating relative directionality of primer designed). Also, as described above some primer sets have a primer with more than one species. For example, similar to the Glade B primer seqeucnes the C-ACF-1 and C-ACF-2 primer sequences differ by the same A to G nucleotide species difference at the same base position.

Examples of the designed Glade C primers illustrate in FIG. 11 include:

| Name | Sequence | SEQ ID No | Length |
|---|---|---|---|
| C-ACF-1 | GCCTCCCTCGCGCCATCAGATCACTCTTTGGCAACGACC | 54 | 39 |
| C-ACF-2 | GCCTCCCTCGCGCCATCAGATCACTCTTTGGCAGCGACC | 55 | 39 |
| C-BF-1 | GCCTCCCTCGCGCCATCAGTGCCAGGAAAATGGAAACCA | 56 | 39 |
| C-BF-2 | GCCTCCCTCGCGCCATCAGTGCCAGGAAATTGGAAACCA | 57 | 39 |
| C-AR-1 | GCCTTGCCAGCCCGCTCAGTGATAAAACCTCCAATTCCCCCTA | 58 | 43 |
| C-AR-2 | GCCTTGCCAGCCCGCTCAGTGATAAAACCTCCAATTCCTCCTA | 59 | 43 |
| C-CR | GCCTTGCCAGCCCGCTCAGGCTTTAATTTTACTGGTACAGTTTCAAT | 60 | 47 |
| C-BR | GCCTTGCCAGCCCGCTCAGTTGGGCCATCCATTCCTGG | 61 | 38 |
| C-4F | GCCTCCCTCGCGCCATCAGGTACCAGTAAAATTAAAGCCAGGAATGG | 62 | 47 |
| C-1F-1 | GCCTCCCTCGCGCCATCAGGGCCATTGACAGAAGAGAAAATAAAAGC | 63 | 47 |
| C-1F-2 | GCCTCCCTCGCGCCATCAGGGCCATTGACAGAAGAAAAATAAAAGC | 64 | 47 |
| C-1R-1 | GCCTTGCCAGCCCGCTCAGGGGTGTGGTATTCCTAATTGAACCTCC | 65 | 46 |
| C-1R-2 | GCCTTGCCAGCCCGCTCAGGGGTGTGGTATTCCTAATTGAACTTCC | 66 | 46 |
| C-2F-1 | GCCTCCCTCGCGCCATCAGGGAAGTTCAATTAGGAATACCACACCC | 67 | 46 |
| C-2F-2 | GCCTCCCTCGCGCCATCAGGGAAGTTCAATTAGGGATACCACACCC | 68 | 46 |
| C-4R-1 | GCCTTGCCAGCCCGCTCAGATACTAGGTATGGTGAATGCAGTATATTT | 69 | 48 |
| C-4R-2 | GCCTTGCCAGCCCGCTCAGATACTAGGTATGGTGAATGCAGTATACTT | 70 | 48 |
| C-5F-1 | GCCTCCCTCGCGCCATCAGCACCAGGGATTAGATATCAATATAATGT | 71 | 47 |
| C-5F-2 | GCCTCCCTCGCGCCATCAGCACCAGGGATTAGATATCAGTACAATGT | 72 | 47 |
| C-2R | GCCTTGCCAGCCCGCTCAGAGGGCTCTAAGATTTTTGTCAT | 73 | 42 |
| C-3F-1 | GCCTCCCTCGCGCCATCAGAGAGCCCTTTAGAGCAAAAAATCCAGA | 74 | 46 |
| C-3F-2 | GCCTCCCTCGCGCCATCAGAGAGCCCTTTAGAGCACAAAATCCAGA | 75 | 46 |
| C-3F-3 | GCCTCCCTCGCGCCATCAGAGAGCCCTTTAGAGCAAAAACCCAGA | 76 | 46 |
| C-3F-4 | GCCTCCCTCGCGCCATCAGAGAGCCCTTTAGAGCACAAAACCCAGA | 77 | 46 |
| C-3R | GCCTTGCCAGCCCGCTCAGCTGTATAGGCTGTACTGTCCATTTGTC | 78 | 46 |
| C-5R | GCCTTGCCAGCCCGCTCAGAACTTCTGTATATCATTGACAGTCCA | 79 | 45 |
| C-ACF-1 | GCCTCCCTCGCGCCATCAGATCACTCTTTGGCAACGACC | 80 | 39 |
| C-ACF-2 | GCCTCCCTCGCGCCATCAGATCACTCTTTGGCAGCGACC | 81 | 39 |
| C-BF-1 | GCCTCCCTCGCGCCATCAGTGCCAGGAAAATGGAAACCA | 82 | 39 |
| C-BF-2 | GCCTCCCTCGCGCCATCAGTGCCAGGAAATTGGAAACCA | 83 | 39 |
| C-AR-1 | GCCTTGCCAGCCCGCTCAGTGATAAAACCTCCAATTCCCCCTA | 84 | 43 |

-continued

| Name | Sequence | SEQ ID No: | Length |
|---|---|---|---|
| C-AR-2 | GCCTTGCCAGCCCGCTCAGTGATAAAACCTCCAATTCCTCCTA | 85 | 43 |
| C-CR | GCCTTGCCAGCCCGCTCAGGCTTTAATTTTACTGGTACAGTTTCAAT | 86 | 47 |
| C-BR | GCCTTGCCAGCCCGCTCAGTTGGGCCATCCATTCCTGG | 87 | 38 |
| C-4F | GCCTCCCTCGCGCCATCAGGTACCAGTAAAATTAAAGCCAGGAATGG | 88 | 47 |
| C-1F-1 | GCCTCCCTCGCGCCATCAGGGCCATTGACAGAAGAGAAAATAAAAGC | 89 | 47 |
| C-1F-2 | GCCTCCCTCGCGCCATCAGGGCCATTGACAGAAGAAAAATAAAAGC | 90 | 47 |
| C-1R-1 | GCCTTGCCAGCCCGCTCAGGGGTGTGGTATTCCTAATTGAACCTCC | 91 | 46 |
| C-1R-2 | GCCTTGCCAGCCCGCTCAGGGGTGTGGTATTCCTAATTGAACTTCC | 92 | 46 |
| C-2F-1 | GCCTCCCTCGCGCCATCAGGGAAGTTCAATTAGGAATACCACACCC | 93 | 46 |
| C-2F-2 | GCCTCCCTCGCGCCATCAGGGAAGTTCAATTAGGGATACCACACCC | 94 | 46 |
| C-4R-1 | GCCTTGCCAGCCCGCTCAGATACTAGGTATGGTGAATGCAGTATATTT | 95 | 48 |
| C-4R-2 | GCCTTGCCAGCCCGCTCAGATACTAGGTATGGTGAATGCAGTATACTT | 96 | 48 |
| C-5F-1 | GCCTCCCTCGCGCCATCAGCACCAGGGATTAGATATCAATATAATGT | 97 | 47 |
| C-5F-2 | GCCTCCCTCGCGCCATCAGCACCAGGGATTAGATATCAGTACAATGT | 98 | 47 |
| C-2R | GCCTTGCCAGCCCGCTCAGAGGGCTCTAAGATTTTGTCAT | 99 | 42 |
| C-3F-1 | GCCTCCCTCGCGCCATCAGAGAGCCCTTTAGAGCAAAAAATCCAGA | 100 | 46 |
| C-3F-2 | GCCTCCCTCGCGCCATCAGAGAGCCCTTTAGAGCACAAAATCCAGA | 101 | 46 |
| C-3F-3 | GCCTCCCTCGCGCCATCAGAGAGCCCTTTAGAGCAAAAAACCCAGA | 102 | 46 |
| C-3F-4 | GCCTCCCTCGCGCCATCAGAGAGCCCTTTAGAGCACAAAACCCAGA | 103 | 46 |
| C-3R | GCCTTGCCAGCCCGCTCAGCTGTATAGGCTGTACTGTCCATTTGTC | 104 | 46 |
| C-5R | GCCTTGCCAGCCCGCTCAGAACTTCTGTATATCATTGACAGTCCA | 105 | 45 |
| C-ACF-1 | GCCTCCCTCGCGCCATCAGATCACTCTTTGGCAACGACC | 106 | 39 |
| C-ACF-2 | GCCTCCCTCGCGCCATCAGATCACTCTTTGGCAGCGACC | 107 | 39 |
| C-BF-1 | GCCTCCCTCGCGCCATCAGTGCCAGGAAAATGGAAACCA | 108 | 39 |
| C-BF-2 | GCCTCCCTCGCGCCATCAGTGCCAGGAAATTGGAAACCA | 109 | 39 |
| C-AR-1 | GCCTTGCCAGCCCGCTCAGTGATAAAACCTCCAATTCCCCCTA | 110 | 43 |
| C-AR-2 | GCCTTGCCAGCCCGCTCAGTGATAAAACCTCCAATTCCTCCTA | 111 | 43 |
| C-CR | GCCTTGCCAGCCCGCTCAGGCTTTAATTTTACTGGTACAGTTTCAAT | 112 | 47 |
| C-BR | GCCTTGCCAGCCCGCTCAGTTGGGCCATCCATTCCTGG | 113 | 38 |
| C-4F | GCCTCCCTCGCGCCATCAGGTACCAGTAAAATTAAAGCCAGGAATGG | 114 | 47 |
| C-1F-1 | GCCTCCCTCGCGCCATCAGGGCCATTGACAGAAGAGAAAATAAAAGC | 115 | 47 |
| C-1F-2 | GCCTCCCTCGCGCCATCAGGGCCATTGACAGAAGAAAAATAAAAGC | 116 | 47 |
| C-1R-1 | GCCTTGCCAGCCCGCTCAGGGGTGTGGTATTCCTAATTGAACCTCC | 117 | 46 |
| C-1R-2 | GCCTTGCCAGCCCGCTCAGGGGTGTGGTATTCCTAATTGAACTTCC | 118 | 46 |
| C-2F-1 | GCCTCCCTCGCGCCATCAGGGAAGTTCAATTAGGAATACCACACCC | 119 | 46 |
| C-2F-2 | GCCTCCCTCGCGCCATCAGGGAAGTTCAATTAGGGATACCACACCC | 120 | 46 |
| C-4R-1 | GCCTTGCCAGCCCGCTCAGATACTAGGTATGGTGAATGCAGTATATTT | 121 | 48 |
| C-4R-2 | GCCTTGCCAGCCCGCTCAGATACTAGGTATGGTGAATGCAGTATACTT | 122 | 48 |
| C-5F-1 | GCCTCCCTCGCGCCATCAGCACCAGGGATTAGATATCAATATAATGT | 123 | 47 |
| C-5F-2 | GCCTCCCTCGCGCCATCAGCACCAGGGATTAGATATCAGTACAATGT | 124 | 47 |
| C-2R | GCCTTGCCAGCCCGCTCAGAGGGCTCTAAGATTTTGTCAT | 125 | 42 |
| C-3F-1 | GCCTCCCTCGCGCCATCAGAGAGCCCTTTAGAGCAAAAAATCCAGA | 126 | 46 |
| C-3F-2 | GCCTCCCTCGCGCCATCAGAGAGCCCTTTAGAGCACAAAATCCAGA | 127 | 46 |
| C-3F-3 | GCCTCCCTCGCGCCATCAGAGAGCCCTTTAGAGCAAAAAACCCAGA | 128 | 46 |
| C-3F-4 | GCCTCCCTCGCGCCATCAGAGAGCCCTTTAGAGCACAAAACCCAGA | 129 | 46 |
| C-3R | GCCTTGCCAGCCCGCTCAGCTGTATAGGCTGTACTGTCCATTTGTC | 130 | 46 |
| C-5R | GCCTTGCCAGCCCGCTCAGAACTTCTGTATATCATTGACAGTCCA | 131 | 45 |

Those of ordinary skill in the art will appreciate that some variability of sequence composition for primer sets exist. This is primarily due to "sequence degeneracy" at certain sequence positions that enable wider utility for the designed primer pairs, such as for use with a wider variety of Glade subclasses. The term "sequence degeneracy" as used herein generally refers to a nucleic acid species substitution at one or more sequence positions to accommodate for minor differences in overall sequence composition. Also, the target regions for the sets of primers may be slightly shifted and thus some difference in primer sequence composition is expected. Also, refinements to the consensus sequence may be made indicating a slight difference of sequence composition in the target region, and similarly some difference in primer sequence composition is expected.

Figure 12:
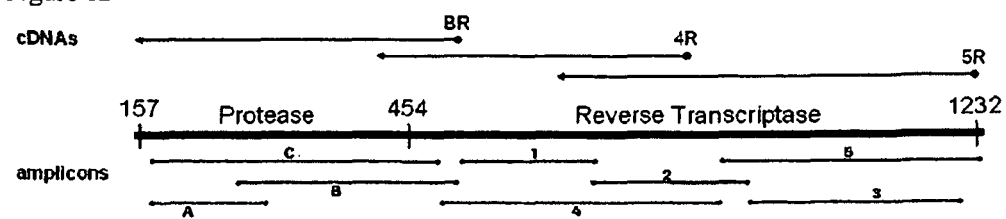
FIG. 12 depicts one embodiment of cDNA molecules generated from HIV RNA spanning the Protease and Reverse Transcriptase regions and overlapping sequence of resulting amplicons.

As described above with respect to the description of generating target specific amplicons for sequencing, the sets of primer species may be employed to generate overlapping amplicons directed to regions of HIV that include the reverse transcriptase, protease, and integrase regions. FIG. 12 provides an illustrative example of an implementation using the sets of primer species. In the example of FIG. 12, three separate cDNA species are generated from HIV RNA using primers BR, 4R-1/4R-2 mix and 5R and the relative positional relationship of each are shown as having overlapping regions with one another. From these 3 cDNAs, eight amplicons are generated by the following primer sets:

Clade B:
cDNA BR: Amplicon A (PR): B-ACF-1/B-ACF-2 mix+B-AR
cDNA BR: Amplicon B (PR): B-BF+B-BR
cDNA BR: Amplicon C (PR): B-ACF-1/B-ACF-2 mix+B-CR
cDNA 4R: Amplicon 1 (RT): B-1F+B-1R-1/B-1R-2 mix
cDNA 5R: Amplicon 2 (RT): B-2F+B-2R
cDNA 5R: Amplicon 3 (RT): B-3F+B-3R
cDNA 4R: Amplicon 4 (RT): B-4F+B-4R-1/B-4R-2 mix
cDNA 5R: Amplicon 5 (RT): B-5F+B-5R-1/B-5R-2 mix
Clade C:
cDNA BR: Amplicon A (PR): C-ACF-1/C-ACF-2 mix+C-AR-1/C-AR-2 mix
cDNA BR: Amplicon B (PR): C-BF-1/C-BF-2 mix+C-BR
cDNA BR: Amplicon C (PR): C-ACF-1/C-ACF-2 mix+C-CR
cDNA 4R: Amplicon 1 (RT): C-1F-1/C-1F-2 mix+C-1R-1/C-1R-2 mix
cDNA 5R: Amplicon 2 (RT): C-2F-1/C-2F-2 mix+C-2R
cDNA 5R: Amplicon 3 (RT): C-3F-1/C-3F-2/C-3F-3/C-3F-4 mix+C-3R
cDNA 4R: Amplicon 4 (RT): C-4F+C-4R-1/C-4R-2 mix
cDNA 5R: Amplicon 5 (RT): C-5F-1/C-5F-2 mix+C-5R Similar to the representation of cDNA, FIG. 12 illustrates the positional relationship of the amplicons as having overlapping regions. In the present example, the amplicons are mixed into a multiplexed sample for each sample of origin and sequenced using the sequencing methods and instrumentation described above.

Figure 13:
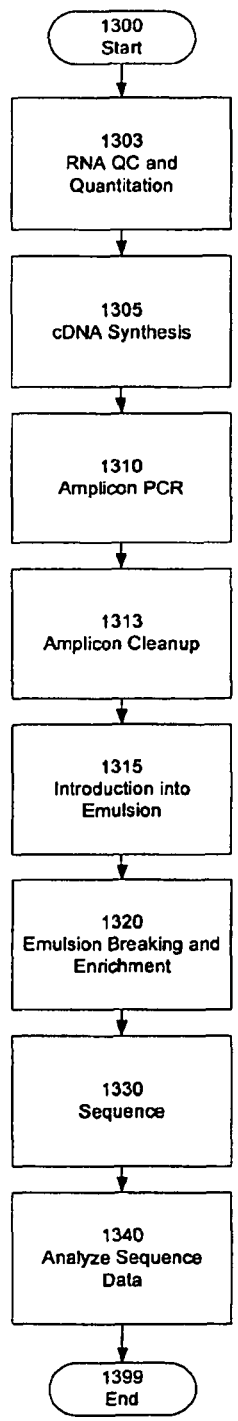
FIG. 13 depicts one embodiment of a method for processing RNA and identification of low frequency sequence variants.

FIG. 13 provides an illustrative example of one embodiment of a method for identification of low frequency variation in HIV subspecies (also referred to as "quasispecies") that includes step 1303 for initial RNA quality control assessments. In some embodiments RNA Qc is performed using BioAnalyzer RNA Pico chips available from Agilent Technologies, followed by aliquoting at 35 ng (enough for one sequencing run) per tube. It is also generally preferable that each aliquot is also barcoded, and performed separately for every HIV RNA sample. Any sample with less than 35 ng RNA (carrier+viral) or with obviously degraded RNA is excluded. Next, the Qc'ed RNA is processed as illustrated in step 1305 for generating one or more cDNA templates from an HIV sample population. In preferred embodiments, each sample is used for cDNA synthesis using three gene-specific primers in three separate reactions in a barcoded 96-well plate format. The cDNA may subsequently be treated with RNAse H to improve subsequent PCR performance.

Subsequently, as illustrated in step 1310, pairs of region specific primers are employed to amplify target region from the cDNA templates generated in step 1305. Three µl of the relevant cDNA is used for each amplicon PCR reaction. Eight amplicons are generated per sample by 40 cycles of PCR in a barcoded 96-well plate format. The amplicons generated in step 1310 may then, in some embodiments, be cleaned up using either Solid Phase Reversible Immobilization (also referred to as SPRI) or gel cutting methods for size selection known in the related art. For example, the amplicons are individually purified with SPRI beads and quantitated using a dsDNA binding fluorescent dye such as Picogreen from the Invitrogen Corporation. Subsequently, the 8 amplicons generated from each sample may be mixed in equimolar ratios. Next, as illustrated in step 1315 nucleic acid strands from the amplicons are introduced into emulsion droplets and amplified as described elsewhere in this specification. In some embodiments, two emulsions may be set up per patient sample, one using an Amplicon A kit and one using an Amplicon B kit both available from 454 Life Sciences. It will be appreciated that in different embodiments, different numbers of emulsions and/or different kits can be employed.

After the amplification the emulsions are broken and beads with amplified populations of immobilized nucleic acids are enriched as illustrated in step 1320. For example, DNA-containing beads may be enriched as described elsewhere in this specification.

The enriched beads are then sequenced as illustrated in step 1330. In some embodiments, each sample is sequenced as described elsewhere in this specification. Subsequently, the output sequence data is analyzed as illustrated in step 1340. In some embodiments, SFF files containing flow gram data filtered for high quality are processed using specific amplicon software and the data analyzed for differences in relation to the consensus sequence derived from an alignment of 6000+ HIV-1 Glade B POL region sequences. The terms "flowgram" or "pyrogram" may be used interchangeably herein and generally refer to a graphical representation of sequence data generated by the sequencing methods described herein. Also, the data analysis includes the association of identified variation in the sequence data with previously identified variants known to be associated with drug resistance, or the variation may be identified as a "new" variant that correlated with drug resistance.

It will be understood that the steps described above are for the purposes of illustration only and are not intended to be limiting, and further that some or all of the steps may be employed in different embodiments in various combinations.

1. Nucleic acid Template Preparation

Nucleic Acid Templates

The template nucleic acid can be constructed from any source of nucleic acid, e.g., any cell, tissue, or organism, and can be generated by any art-recognized method. Alternatively, template libraries can be made by generating a complementary DNA (cDNA) library from RNA, e.g., messenger RNA (mRNA). Methods of sample preparation may be found in U.S. Pat. No. 7,323,305 and co-pending PCT application US04/02570 and is also published in WO/04070007—all incorporated herein by reference in their entirety.

One preferred method of nucleic acid template preparation is to perform PCR on a sample to amplify a region containing the allele or alleles of interest. The PCR technique can be applied to any nucleic acid sample (DNA, RNA, cDNA) using oligonucleotide primers spaced apart from each other. The primers are complementary to opposite strands of a double stranded DNA molecule and are typically separated by from about 50 to 450 nucleotides or more (usually not more than 2000 nucleotides). The PCR method is described in a number of publications, including Saiki et al., Science (1985) 230: 1350-1354; Saiki et al., Nature (1986) 324:163-166; and Scharf et al., Science (1986) 233:1076-1078. Also see U.S. Pat. Nos. 4,683,194; 4,683,195; and 4,683,202, the text of each patent is herein incorporated by reference. Additional methods for PCR amplification are described in: PCR Technology: Principles and Applications for DNA Amplification ed. HA Erlich, Freeman Press, New York, N.Y. (1992); PCR Protocols: A Guide to Methods and Applications, eds. Innis, Gelfland, Snisky, and White, Academic Press, San Diego, Calif. (1990); Manila et al. (1991) Nucleic Acids Res. 19: 4967; Eckert, K. A. and Kunkel, T. A. (1991) PCR Methods and Applications 1: 17, and; PCR, eds. McPherson, Quirkes, and Taylor, IRL Press, Oxford, which are incorporated herein by reference.

2. Nucleic Acid Template Amplification

In order for the nucleic acid template (i.e., the amplicons generated by the PCR method of the first step) to be sequenced according to the methods of this invention the copy number must be amplified a second time to generate a sufficient number of copies of each template to produce a detectable signal by the light detection means. Any suitable nucleic acid amplification means may be used. In a preferred embodiment, a novel amplification system, herein termed EBCA (Emulsion Based Clonal Amplification or bead emulsion amplification) is used to perform this second amplification.

EBCA is performed by attaching a template nucleic acid (e.g., DNA) to be amplified to a solid support, preferably in the form of a generally spherical bead. A library of single stranded template DNA prepared according to the sample preparation methods of this invention is an example of one suitable source of the starting nucleic acid template library to be attached to a bead for use in this amplification method.

Figure 1B:
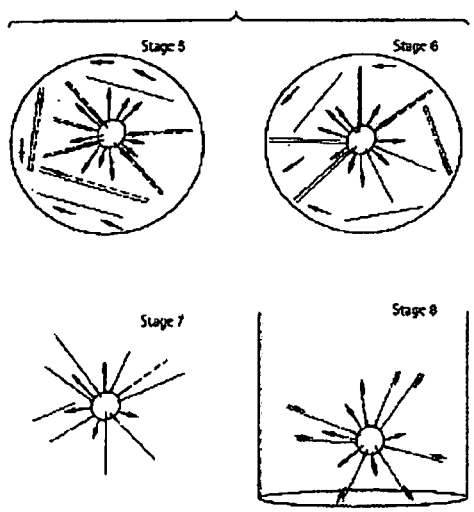

The bead is linked to a large number of a single primer species (i.e., primer B in FIG. 1) that is complementary to a region of the template DNA. Template DNA annealed to the bead bound primer. The beads are suspended in aqueous reaction mixture and then encapsulated in a water-in-oil emulsion. The emulsion is composed of discrete aqueous phase microdroplets, approximately 60 to 200 um in diameter, enclosed by a thermostable oil phase. Each microdroplet contains, preferably, amplification reaction solution (i.e., the reagents necessary for nucleic acid amplification). An example of an amplification would be a PCR reaction mix (polymerase, salts, dNTPs) and a pair of PCR primers (primer A and primer B). See, FIG. 1A. A subset of the microdroplet population also contains the DNA bead comprising the DNA template. This subset of microdroplet is the basis for the amplification. The microcapsules that are not within this subset have no template DNA and will not participate in amplification. In one embodiment, the amplification technique is PCR and the PCR primers are present in a 8:1 or 16:1 ratio (i.e., 8 or 16 of one primer to 1 of the second primer) to perform asymmetric PCR.

In this overview, the DNA is annealed, to an oligonucleotide (primer B) which is immobilized to a bead. During thermocycling (FIG. 1B), the bond between the single stranded DNA template and the immobilized B primer on the bead is broken, releasing the template into the surrounding microencapsulated solution. The amplification solution, in this case, the PCR solution, contains addition solution phase primer A and primer B. Solution phase B primers readily bind to the complementary b' region of the template as binding kinetics are more rapid for solution phase primers than for immobilized primers. In early phase PCR, both A and B strands amplify equally well (FIG. 1C).

By midphase PCR (i.e., between cycles 10 and 30) the B primers are depleted, halting exponential amplification. The reaction then enters asymmetric amplification and the amplicon population becomes dominated by A strands (FIG. 1D). In late phase PCR (FIG. 1E), after 30 to 40 cycles, asymmetric amplification increases the concentration of A strands in solution. Excess A strands begin to anneal to bead immobilized B primers. Thermostable polymerases then utilize the A strand as a template to synthesize an immobilized, bead bound B strand of the amplicon.

In final phase PCR (FIG. 1F), continued thermal cycling forces additional annealing to bead bound primers. Solution phase amplification may be minimal at this stage but concentration of immobilized B strands increase. Then, the emulsion is broken and the immobilized product is rendered single stranded by denaturing (by heat, pH etc.) which removes the complimentary A strand. The A primers are annealed to the A' region of immobilized strand, and immobilized strand is loaded with sequencing enzymes, and any necessary accessory proteins. The beads are then sequenced using recognized pyrophosphate techniques (described, e.g., in U.S. Pat. Nos. 6,274,320, 6258,568 and 6,210,891, incorporated in toto herein by reference).

In a preferred embodiment, the primers used for amplification are bipartite—comprising a 5' section and a 3' section. The 3' section of the primer contains target specific sequence (see FIG. 2) and performed the function of PCR primers. The 5' section of the primer comprises sequences which are useful for the sequencing method or the immobilization method. For example, in FIG. 2, the 5' section of the two primers used for amplification contains sequences (labeled 454 forward and 454 reverse) which are complementary to primers on a bead or a sequencing primer. That is, the 5' section, containing the forward or reverse sequence, allows the amplicons to attach to beads that contain immobilized oligos which are complementary to the forward or reverse sequence. Furthermore, sequencing reaction may be initiated using sequencing primers which are complementary to the forward and reverse primer sequences. Thus one set of beads comprising sequences complementary to the 5' section of the bipartite primer may be used on all reactions. Similarly, one set of sequencing primers comprising sequences complementary to the 5' section of the bipartite primer may be used to sequence any amplicons made using the bipartite primer. In the most preferred embodiment, all bipartite primer sets used for amplification would have the same set of 5' sections such as the 454 forward primer and 454 reverse primer shown in FIG. 2. In this case, all amplicons may be analyzed using standard beads coated with oligos complementary to the 5' section. The same oligos (immobilized on beads or not immobilized) may be used as sequencing oligos.

Breaking the Emulsion and Bead Recovery

Following amplification of the template, the emulsion is "broken" (also referred to as "demulsification" in the art). There are many methods of breaking an emulsion (see, e.g., U.S. Pat. No. 5,989,892 and references cited therein) and one of skill in the art would be able to select the proper method. One preferred method of breaking the emulsion is described in detail in the Examples section.

After the emulsion is broken, the amplified template-containing beads may then be resuspended in aqueous solution for use, for example, in a sequencing reaction according to known technologies. (See, Sanger, F. et al., Proc. Natl. Acad. Sci. U.S.A. 75, 5463-5467 (1977); Maxam, A. M. & Gilbert, W. Proc Natl Acad Sci USA 74, 560-564 (1977); Ronaghi, M. et al., Science 281, 363, 365 (1998); Lysov, I. et al., Dokl Akad Nauk SSSR 303, 1508-1511 (1988); Bains W. & Smith G. C. J. TheorBiol 135, 303-307 (1988); Drnanac, R. et al., Genomics 4, 114-128 (1989); IChrapko, K. R. et al., FEBS Lett 256. 118-122 (1989); Pevzner P. A. J Biomol Struct Dyn 7, 63-73 (1989); Southern, E. M. et al., Genomics 13, 1008-1017 (1992).) If the beads are to be used in a pyrophosphate-based sequencing reaction (described, e.g., in U.S. Pat. Nos. 6,274,320, 6,258,568 and 6,210,891, and incorporated in tow herein by reference), then it is necessary to remove the second strand of the PCR product and anneal a sequencing primer to the single stranded template that is bound to the bead.

At this point, the amplified DNA on the bead may be sequenced either directly on the bead or in a different reaction vessel. In an embodiment of the present invention, the DNA is sequenced directly on the bead by transferring the bead to a reaction vessel and subjecting the DNA to a sequencing reaction (e.g., pyrophosphate or Sanger sequencing). Alternatively, the beads may be isolated and the DNA may be removed from each bead and sequenced. In either case, the sequencing steps may be performed on each individual bead.

3. Methods of Sequencing Nucleic Acids

One method of sequencing is pyrophosphate-based sequencing. In pyrophosphate based sequencing sample DNA sequence and the extension primer subjected to a polymerase reaction in the presence of a nucleotide triphosphate whereby the nucleotide triphosphate will only become incorporated and release pyrophosphate (PPi) if it is complementary to the base in the target position, the nucleotide triphosphate being added either to separate aliquots of sample-primer mixture or successively to the same sample-primer mixture. The release of PPi is then detected to indicate which nucleotide is incorporated.

In an embodiment, a region of the sequence product is determined by annealing a sequencing primer to a region of the template nucleic acid, and then contacting the sequencing primer with a DNA polymerase and a known nucleotide triphosphate, i.e., dATP, dCTP, dGTP, dTTP, or an analog of one of these nucleotides. The sequence can be determined by detecting a sequence reaction byproduct, as is described below.

The sequence primer can be any length or base composition, as long as it is capable of specifically annealing to a region of the amplified nucleic acid template. No particular structure for the sequencing primer is required so long as it is able to specifically prime a region on the amplified template nucleic acid. Preferably, the sequencing primer is complementary to a region of the template that is between the sequence to be characterized and the sequence hybridizable to the anchor primer. The sequencing primer is extended with the DNA polymerase to form a sequence product. The extension is performed in the presence of one or more types of nucleotide triphosphates, and if desired, auxiliary binding proteins.

Incorporation of the dNTP is preferably determined by assaying for the presence of a sequencing byproduct. In a preferred embodiment, the nucleotide sequence of the sequencing product is determined by measuring inorganic pyrophosphate (PPi) liberated from a nucleotide triphosphate (dNTP) as the dNMP is incorporated into an extended sequence primer. This method of sequencing, termed Pyrosequencing™ technology (PyroSequencing AB, Stockholm, Sweden) can be performed in solution (liquid phase) or as a solid phase technique. PPi-based sequencing methods are described generally in, e.g., WO9813523A1, Ronaghi, et al., 1996. *Anal. Biochem.* 242: 84-89, Ronaghi, et al., 1998. *Science* 281: 363-365 (1998) and USSN 2001/0024790. These disclosures of PPi sequencing are incorporated herein in their entirety, by reference. See also, e.g., U.S. Pat. Nos. 6,210,891 and 6,258,568, each fully incorporated herein by reference.

In a preferred embodiment, DNA sequencing is performed using 454 Corporation's (454 Life Sciences) sequencing apparatus and methods which are disclosed in U.S. Pat. No. 7,323,305 and copending patent applications U.S. Ser. No. 10/768,729, U.S. Ser. No. 10/767,899, and U.S. Ser. No. 10/767,894—all of which are filed Jan. 28, 2004.

Unless otherwise defined, all technical and scientific terms used herein have the same meaning as commonly understood by one of ordinary skill in the art to which this invention belongs. Conunonly understood definition would include those defined in U.S. Ser. No. 60/476,602, filed Jun. 6, 2003; U.S. Ser. No. 60/476,504, filed Jun. 6, 2003; U.S. Ser. No. 60/443,471, filed Jan. 29, 2003; U.S. Ser. No. 60/476,313, filed Jun. 6, 2003; U.S. Ser. No. 60/476,592, filed Jun. 6, 2003; U.S. Ser. No. 60/465,071, filed Apr. 23, 2003; U.S. Ser. No. 60/497,985, filed Aug. 25, 2003; U.S. Pat. No. 7,323,305, filed Jan. 28, 2004; Ser. No. 10/767,899 filed Jan. 28, 2004; U.S. Ser. No. 10/767,894 filed Jan. 28, 2004. All patents, patent applications, and references cited in this application are fully incorporated by reference.

EXAMPLES

Example 1

Sequencing of the HLA Locus

Five PCR primer pairs were designed to span known, publicly disclosed SNPs in the MHC class II locus. Primers were design using the Primer3 software (Whitehead Institute for Biomedical Research), using approx. 200 base-pair long genomic sequences encompassing the target regions as input. Each primer consisted of a locus specific 3' portion ranging in length from 20 to 24 bases and a constant 19 base 5' portion (shown in lowercase) that includes a 4 base key (high-lighted in bold). Primers were purchased from Integrated DNA Technologies (Coralville, Iowa):

```
SAD1F-DC1
                                        (SEQ ID NO: 1)
gcctccctcgcgcca tcag ACCTCCCTCTGTGTCCTTACAA
SAD1R-DC1
                                        (SEQ ID NO: 2)
gccttgccagcccgc tcag GGAGGGAATCATACTAGCACCA SAD1F-DD14
                                        (SEQ ID NO: 3)
gcctccctcgcgcca tcag TCTGACGATCTCTGTCTTCTAACC
SAD1R-DD14
                                        (SEQ ID NO: 4)
gccttgccagcccgc tcag GCCTTGAACTACACGTGGCT SAD1F-DE15
                                        (SEQ ID NO: 5)
gcctccctcgcgcca tcag ATTTCTCTACCACCCCTGGC
SAD1R-DE15
                                        (SEQ ID NO: 6)
gccttgccagcccgc tcag AGCTCATGTCTCCCGAAGAA SAD1F-GA9
                                        (SEQ ID NO: 7)
gcctccctcgcgcca tcag AAAGCCAGAAGAGGAAAGGC
SAD1R-GA9
                                        (SEQ ID NO: 8)
gccttgccagcccgc tcag CTTGCAGATTGGTCATAAGG SAD1F-F5
                                        (SEQ ID NO: 9)
gcctccctcgcgcca tcag ACAGTGCAAACACCACCAAA
SAD1R-F5
                                        (SEQ ID NO: 10)
gccttgccagcccgc tcag CCAGTATTCATGGCAGGGTT
```

Human genomic DNA (Cornell Medical Institute for Research, Camden, N.J.) from 4 individuals was quantitated based on optical density at 260 nm and 100 ng (approx. 15,000 haploid genome equivalents) was used as template for each PCR amplification reaction. PCR reactions were performed under standard reaction conditions (60 mM Tris-$SO_4$, pH 8.9, 18 mM $(NH_4)_2SO_4$, 2.5 mM $MgSO_4$, 1 mM dNTPs, 0.625 uM of each primer, 4.5 units Platinum Taq High Fidelity polymerase (Invitrogen, Carlsbad, Calif.)) with the following temperature profile: 3 min 94° C.; 30 cycles of 30 s 94° C., 45 s 57° C., 1 min 72° C.; 3 min 72° C. Amplification products were purified using a QiaQuick PCR Purification kit (Qiagen, Valencia, Calif.), and their anticipated sizes (156 to 181 base pairs) were verified on a 2100 BioAnalyzer microfluidics instrument using a 500 DNA LabChip® (Agilent Technologies, Inc, Palo Alto, Calif.). The purified amplicons were quantitated with a PicoGreen® dsDNA quantitation kit (Molecular Probes, Eugene, Oreg.) and diluted to $10^7$ copies per microliter.

EBCA (Emulsion Based Clonal Amplification) was performed as described above with 0.5 amplicons per bead, using amplification primers SAD1F (GCC TCC CTC GCG CCA (SEQ ID NO:11)) and SAD1R and Sepharose capture beads with SADR1 (GCC TTG CCA GCC CGC (SEQ ID NO:12)) capture primer (Amersham BioSciences, Piscataway, N.J.). All further manipulations, including breaking of the emulsions and sequencing on the PicoTiter plate were performed as described above.

Example 2

Sensitive Mutation Detection

To demonstrate the capability of the current system (i.e., the 454 platform) to detect low abundance sequence variants, specifically single base substitutions, experiments were designed to sequence known alleles mixed at various ratios.

Figure 3:
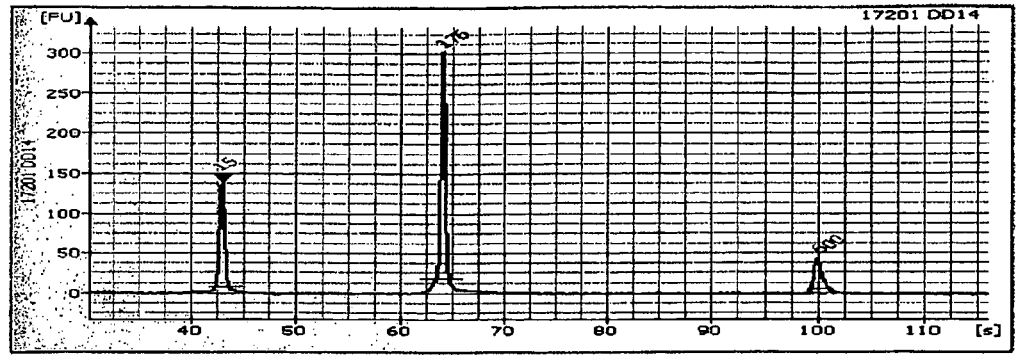
FIG. 3 depicts quality assessment of amplicons produced with primer pairs SAD1F/R-DD14 (panel A), SAD1F/R-DE15 (panel B) and SAD1F/R-F5 (panel C). Analysis was performed on a BioAnalyzer DNA 1000 BioChip with the center peaks representing the PCR products and the flanking peaks reference size markers. Each peak was measured to be within 5 by of the theoretical size which ranged from 156-181 base pairs.
Figure 3:
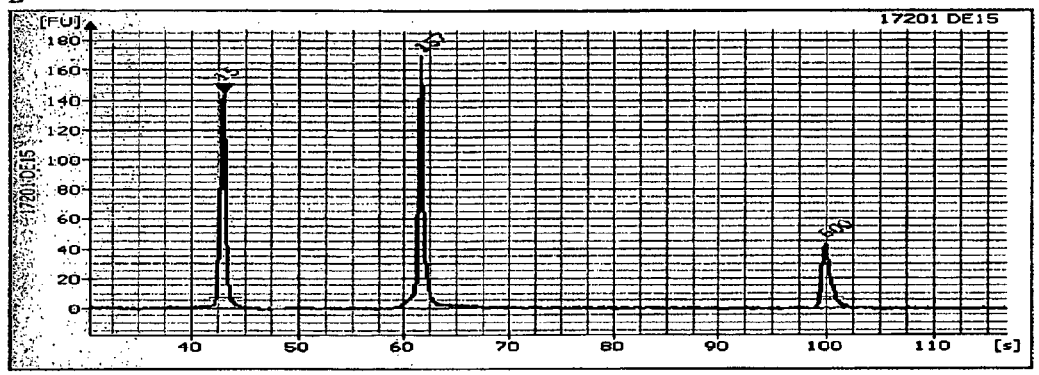
Figure 3:
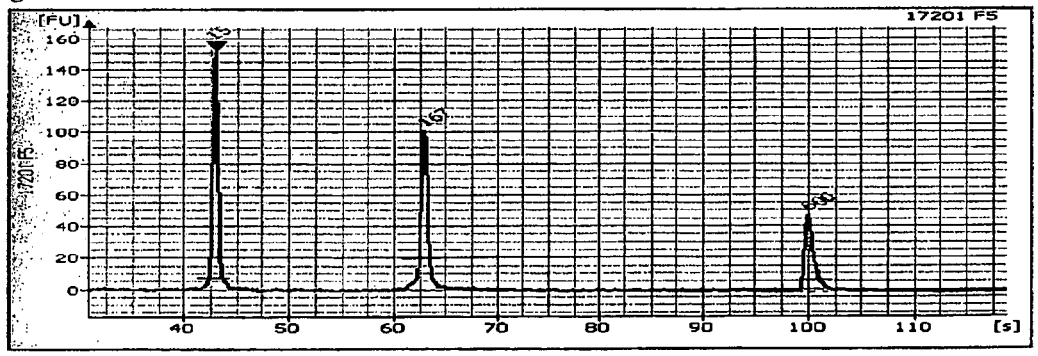

The 6 primer pairs listed above were tested for amplification efficiency and further analysis was performed using pairs SAD1F/R-DD14, SAD1F/R-DE15 and SAD1F/R-F5 which all produced distinct amplification products (FIG. 3). A total of 8 human genomic DNA samples were amplified and sequenced on the 454 platform to determine the genotypes for each locus. To simplify the experimental setup all further analysis was done using primer pair SAD1F/R-DD14 (FIG. 3A) and two samples shown to be homozygous for either the C or T allele at the particular locus.

Figure 2:
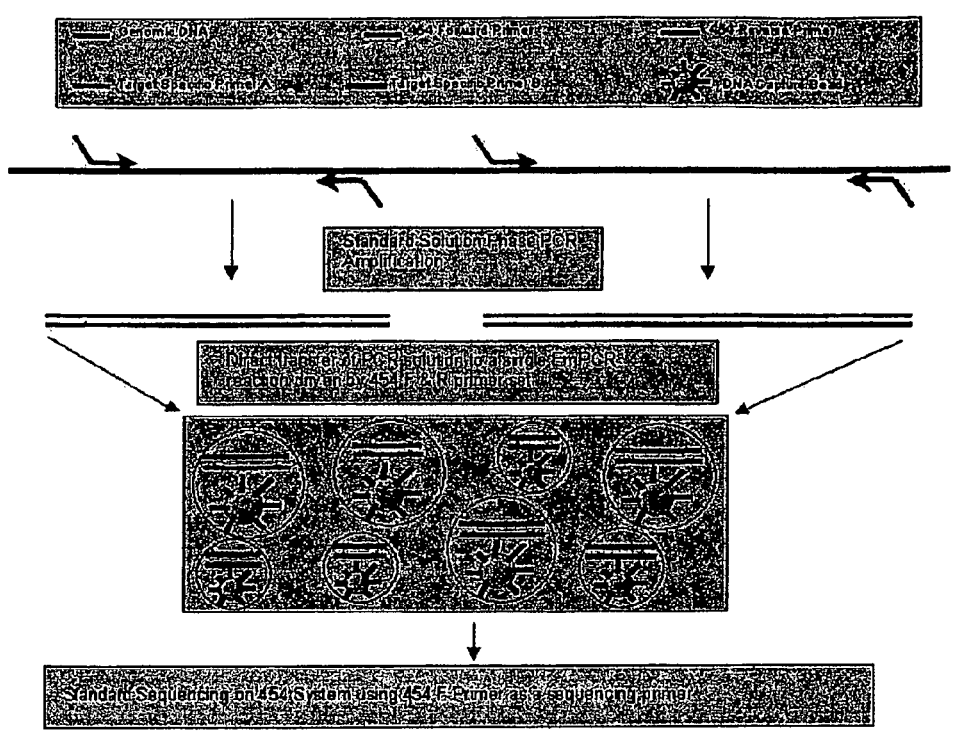
FIG. 2 depicts schematic of ultradeep sequencing method.
Figure 4:
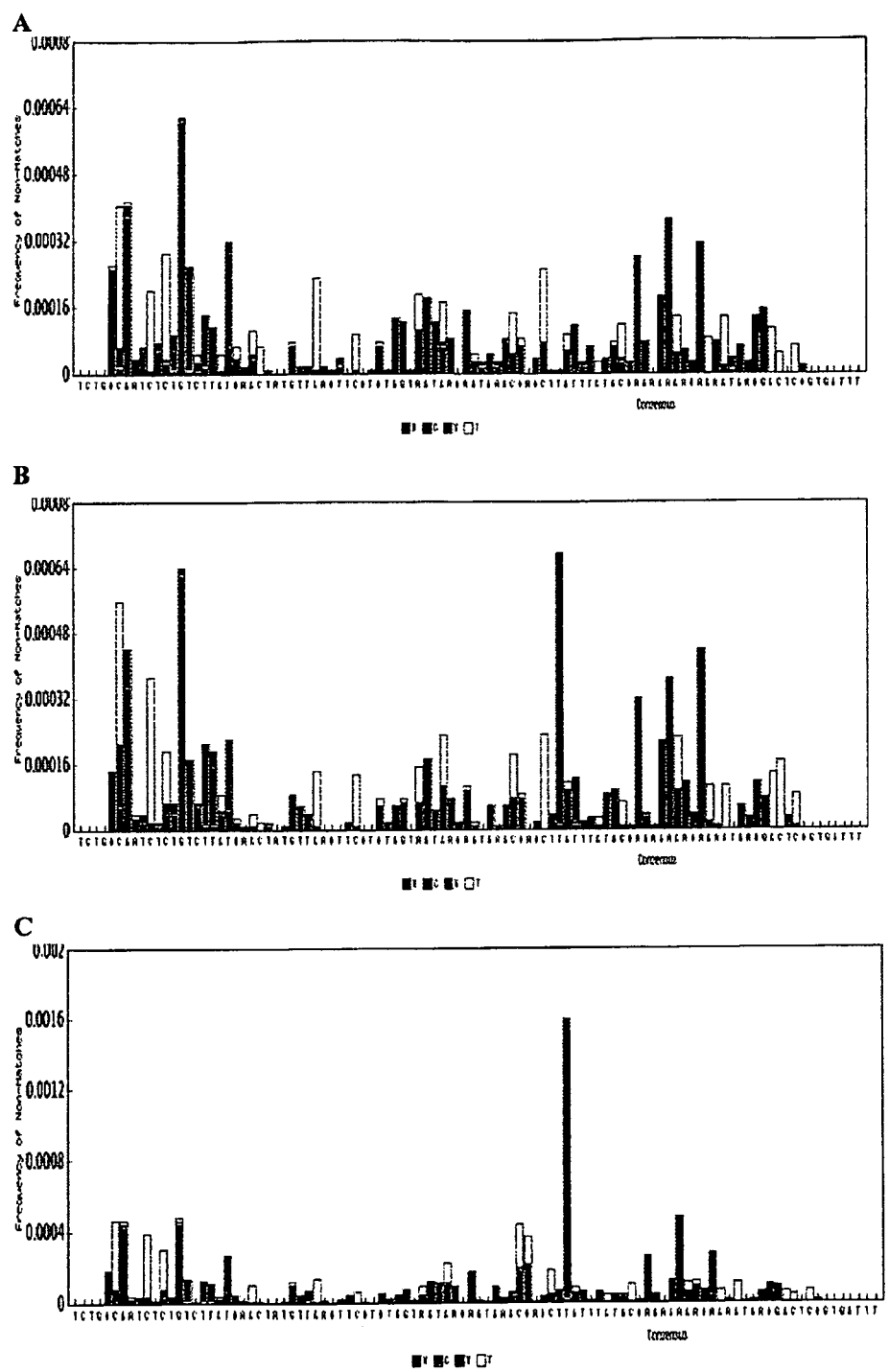
FIG. 4 depicts nucleotide frequencies (frequency of non-matches) in amplicons representing two distinct alleles in the MHC II locus were mixed in approximate ratios (C allele to T allele) of 1:500 (A) and 1:1000 (B), or T allele only (A), clonally amplified and sequenced on 454 Life Sciences' sequencing platform. Each bar represents the frequency of deviation from the consensus sequence and are color-coded according to the resulting base substitution (red=A; green=C; blue=G; yellow=T).
Figure 5:
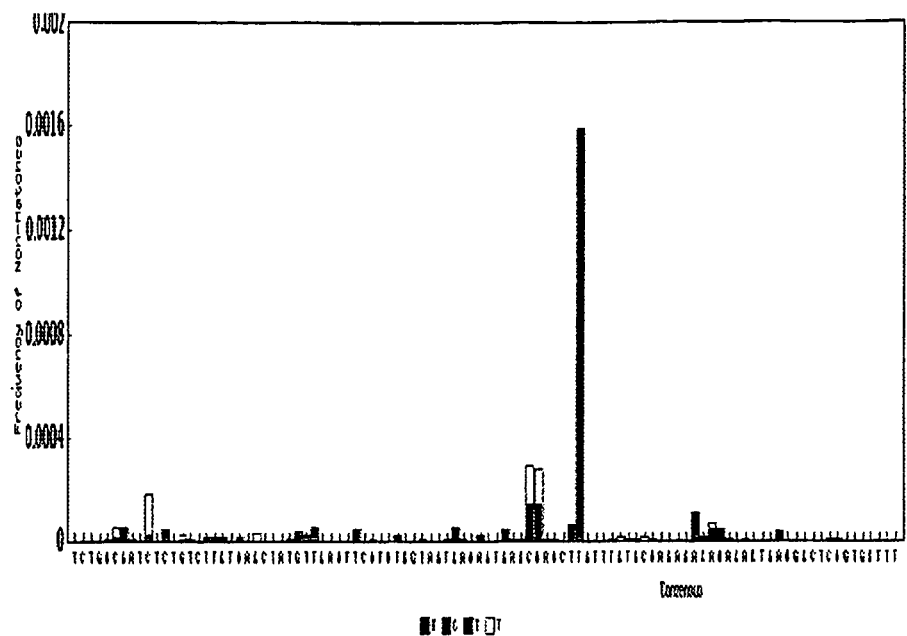
FIG. 5 depicts the same data as presented in FIG. 4B and 4C, however after background subtraction using the T allele-only sample presented in FIG. 4A.
Figure 5:
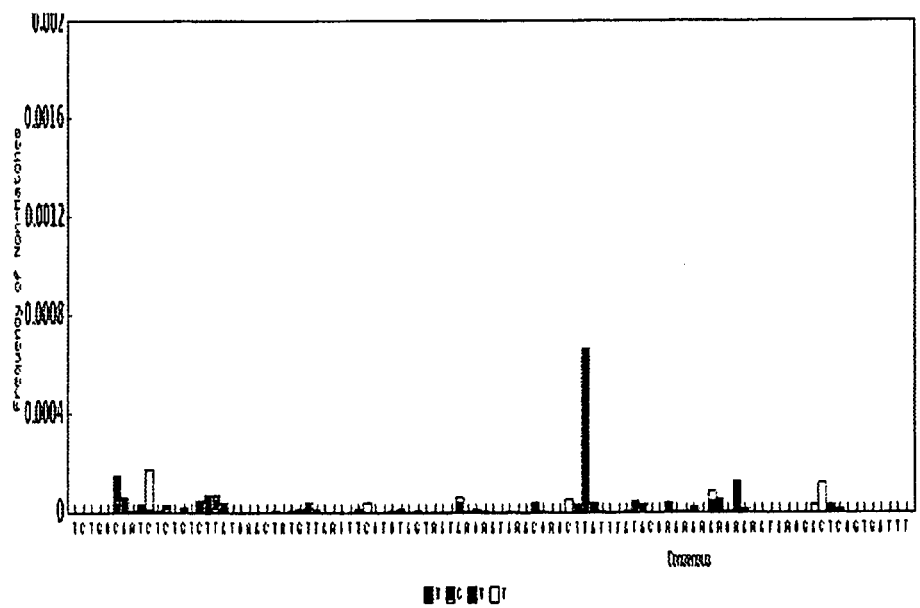

The primary amplicons from each sample were quantitated and mixed at specific ratios ranging from 10:90 down to 1:1000, typically with the T allele in excess. After mixing the samples were diluted to a working concentration of $2 \times 10^6$ copies per microliter and subjected to EBCA and sequenced on the 454 platform. FIG. 2 presents sequencing data obtained from the mixing of the C allele in approximate ratios 1:500 and 1:1000 into the T allele. In both cases roughly 10,000 high-quality sequencing reads were generated and subjected to Blast analysis to identify nucleotide substitutions against a reference sequence (in this case the T allele carrying sequence). For visualization of the results the substitution frequency is plotted in a color-coded fashion relative to the reference sequence. The data demonstrate that in both samples the low frequency single base substitutions were readily identified (FIG. 4A-C). Furthermore the background was found to be relatively consistent between samples allowing background subtraction. This typically produced a signal-to-noise ratio even for the 1:1000 allele that exceeded 10 (FIGS. 5A and B). Additional experimentation using samples of known genotypes has confirmed the ability to detect single nucleotide substitutions down to at least a 0.1% abundance level. Additional confidence in low abundance changes can be obtained from sequencing a template in both directions. Typically the difference between the frequencies from the two independent bidirectional data sets is within 20% down to the 1% abundance level.

Figure 6:
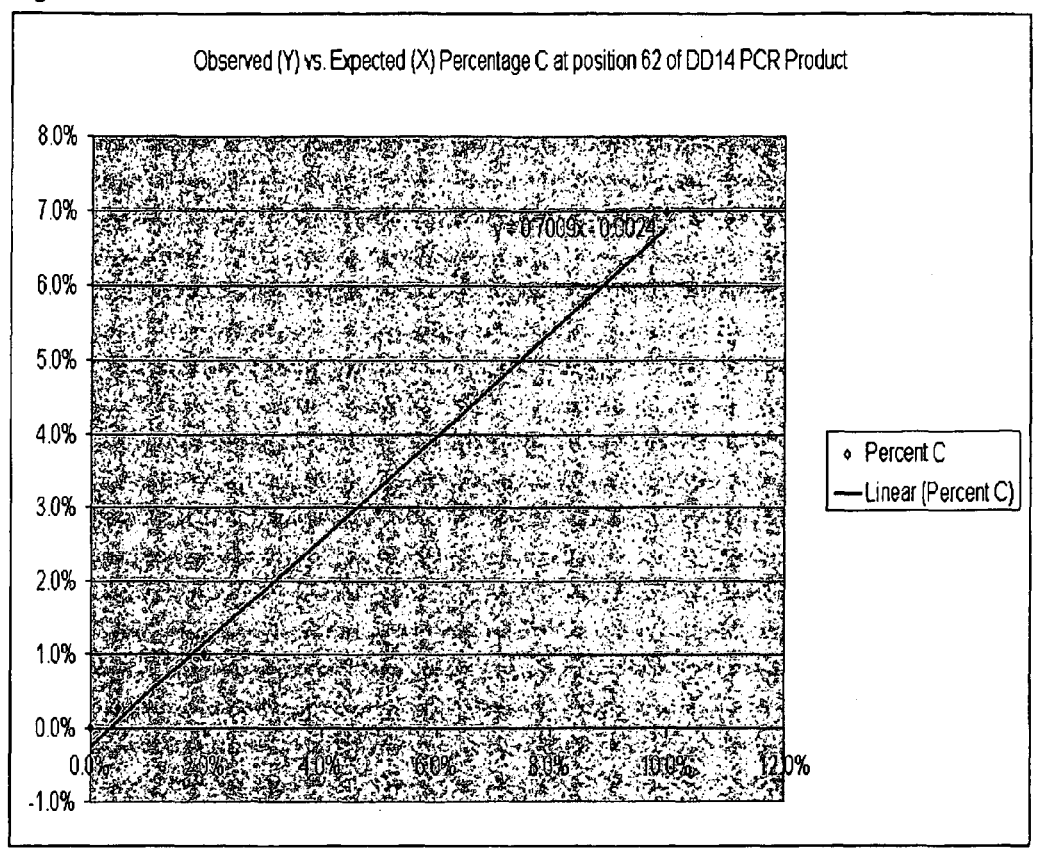
FIG. 6 depicts various ratios of C to T alleles from the DD14 HLA locus were mixed and sequenced on the 454 platform to determine dynamic range. The experimentally observed ratios are plotted against the intended ratios (abscissa). The actual number of sequencing reads for each data point is summarized in Table 1

To demonstrate a linear response over a broader range of allelic ratios, amplicons representing the T and C alleles from the DD14 HLA locus were mixed in ratios 1:10, 1:20, 1:50 and 1:200 (10%, 5%, 2% and 0.5%), EBCA amplified and sequenced. FIG. 6 shows that a linear increase in the relative number of low frequency allele was observed throughout the range ($R^2$=0.9927). The recorded absolute frequencies somewhat deviated from the intended ratios (See Table below) and were attributed to commonly observed difficulties trying to precisely quantitate, aliquot and mix small amounts of DNA.

| Expected Percent C | Total Reads | Expected C | Observed C | Observed T | Observed Percent C |
|---|---|---|---|---|---|
| 0.00% | 101450 | 0 | 1 | 101449 | 0.00% |
| 0.50% | 72406 | 361 | 193 | 72213 | 0.27% |
| 2.00% | 103292 | 2045 | 1049 | 102243 | 1.02% |
| 2.00% | 57115 | 1131 | 578 | 56537 | 1.01% |
| 5.00% | 112378 | 5452 | 3340 | 109038 | 2.97% |
| 10.00% | 104906 | 9760 | 7311 | 97595 | 6.97% |

Summary of sequencing used to generate plot in FIG. 6. Numbers in columns 2-5 indicate total number of sequenced templates, and the expected and observed numbers for each allele respectively.

Example 3

Bacterial 16S Project—A Method to Examine Bacteria Populations

Bacterial population surveys are essential applications for many fields including industrial process control, in addition to medical, environmental and agricultural research. One common method utilizes the 16S ribosomal RNA gene sequence to distinguish bacterial species (Jonasson, Olofsson et al. 2002; Gratin, Olofsson et al. 2003). Another method similarly examines the intervening sequence between the 16S and 23S ribosomal RNA genes (Garcia-Martinez, Bescos et al. 2001). However, the majority of researchers find a complete census of complex bacterial populations is impossible using current sample preparation and sequencing technologies; the labor requirements for such a project are either prohibitively expensive or force dramatic subsampling of the populations.

Currently, high throughput methods are not routinely used to examine bacterial populations. Common practice utilizes universal primer(s) to amplify the 16S ribosomal RNA gene (or regions within the gene), which are subsequently subcloned into vectors and sequenced. Restriction digests are often conducted on the vectors in an effort to reduce the sequencing load by eliminating vectors which exhibit identical restriction patterns. Resultant sequences are compared to a database of known genes from various organisms; estimates of population composition are drawn from the presence of species- or genus-specific gene sequences. The methods of this disclosure has the potential to revolutionize the study of bacterial populations by drastically reducing the labor costs through eliminating cloning and restriction digest steps, increasing informational output by providing complete sequences from the 16S (and possibly intergenic and 23S) RNA regions possibly allowing previously unobtainable sub-strain differentiation, and potentially providing estimates of species density by converting sequence oversampling into relative abundance.

One preferred method of nucleic acid sequencing is the pyrophosphate based sequencing methods developed by 454 Life Sciences. Utilization of the methods of the invention coupled with all aspects of the massively parallel 454 technology (some of which is disclosed in this specification) can greatly increase the throughput and reduce the cost of community identification. The 454 technology eliminates the need to clone large numbers of individual PCR products while the small size of the 16S gene (1.4 kb) allows tens of thousands of samples to be processed simultaneously. The process has been successfully demonstrated in the manner outlined below.

Initially, *Escherichia coli* 16S DNA was obtained from *E. coli* TOP10 competent cells (Invitrogen, Carlsbad, Calif.) transformed with the PCR2.1 vector, plated onto LB/Ampicillin plates (50 µg/ml) and incubated overnight at 37° C. A single colony was picked and inoculated into 3 ml of LB/Ampicillin broth and shaken at 250 RPM for 6 hours at 37° C. One microliter of this solution was used as template for amplifying the V1 and V3 regions of the 16S sequence.

Bipartite PCR primers were designed for two variable regions in the 16S gene, denoted V1 and V3 as described in Monstein et al (Monstein, Nikpour-Badr et al. 2001). Five prime tags comprised of 454 specific, 19 base (15 base amplification primers, followed by a 3', 4 base (TCGA) key) forward or reverse primers were fused to the region specific forward and reverse primers that flank the variable V1 and V3 regions. This may be represented as: 5'-(15 base forward or reverse Amplification primer)-(4 base key)-(forward or reverse V1 or V3 primer)-3'. The primers used to produce 16S amplicons contain the following sequences, with the sequences in capital letter representing the V1 or V3 specific primers, the four bases in bold identify the key, and the lower case bases indicate the 454 amplification primers:

```
SAD-V1 fusion (forward):
                                     (SEQ ID NO: 13)
gcctccctcgcgcca tcag GAAGAGTTTGATCATGGCTCAG
SAD-V1 fusion (reverse):
                                     (SEQ ID NO: 14)
gccttgccagcccgc tcag TTACTCACCCGTCCGCCACT
SAD-V3 fusion (forward):
                                     (SEQ ID NO: 15)
gcctccctcgcgcca tcag GCAACGCGAAGAACCTTACC
SAD-V3 fusion (reverse):
                                     (SEQ ID NO: 16)
gccttgccagcccgc tcag ACGACAGCCATGCAGCACCT
```

The V1 and V3 amplicons were generated separately in PCR reactions that contained the following reagents: 1×HiFi buffer, 2.5 mM MgSO$_4$ (Invitrogen), 1 mM dNTPs (Pierce, Milwaukee Wis.), 1 µM each forward and reverse bipartite primer for either V1 or V3 regions (IDT, Coralville, Iowa), 0.15 U/µl Platinum HiFi Taq (Invitrogen). One microliter of *E. coli*/LB/Ampicillin broth was added to the reaction mixture and 35 cycles of PCR were performed (94° C. for 30 seconds, 55° C. for 30 seconds, and 68° C. for 150 seconds, with the final cycle followed by a 10° C. infinite hold). Subsequently, one microliter of the amplified reaction mix was run on the Agilent 2100 Bioanalyzer (Agilent, Palo Alto, Calif.) to estimate the concentration of the final product, and assure the proper size product 155 by for the V1, 145 by for the V3) was generated.

The V1 and V3 products were then combined, emulsified at template concentrations ranging from 0.5 to 10 template molecules per DNA capture bead and amplified through the EBCA (Emulsion Based Clonal Amplification) process as outlined in the EBCA Protocol section below. The resulting clonally amplified beads were subsequently sequenced on the 454 Genome Sequencer (454 Life Sciences, Branford Conn.).

The sequences obtained from the amplified beads were aligned against the *Escherichia coli* 16S gene sequence (Entrez gi174375). Acceptable (or "mapped") alignments were distinguished from rejected (or "unmapped") alignments by calculating the alignment score for each sequence. The score is the average logarithm of the probability that an observed signal corresponds to the expected homopolymer, or:

$$S = \Sigma \ln [P(s|h)]/N$$

where S is the computed alignment score, P is the probability at a specific flow, s is the signal measured at that flow, h is the length of the reference homopolymer expected at that flow, and N is the total number of flows aligned. The alignment score for each sequence was then compared to a Maximum Alignment Score, or MAS; alignments scoring less than the MAS were considered "real" and were printed to the output file. For this project, a MAS of 1.0 (roughly equivalent to 95% identity) was used.

Figure 7:
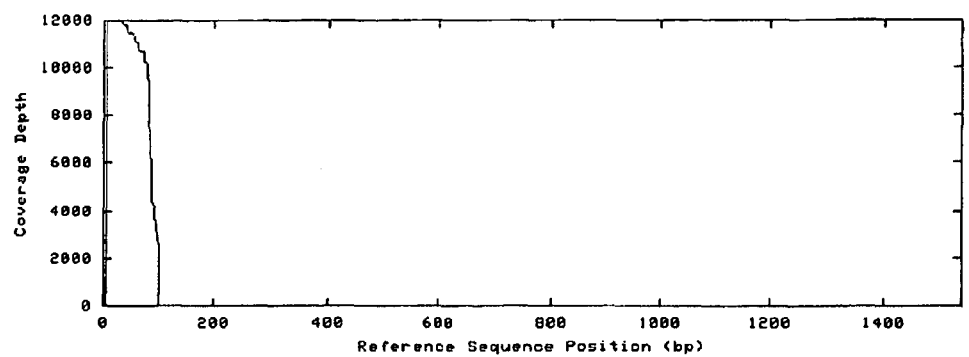
FIG. 7 A: A graphical display showing the location of the reads mapping to the 1.6 Kb 16S gene fragment indicating roughly 12,000 reads mapping to the first 100 bases of the 16S gene. B: shows similar results as 7A except with the V3 primers which maps to a region around base 1000. C: shows locations of the reads where both V1 and V3 primers are used.
Figure 7:
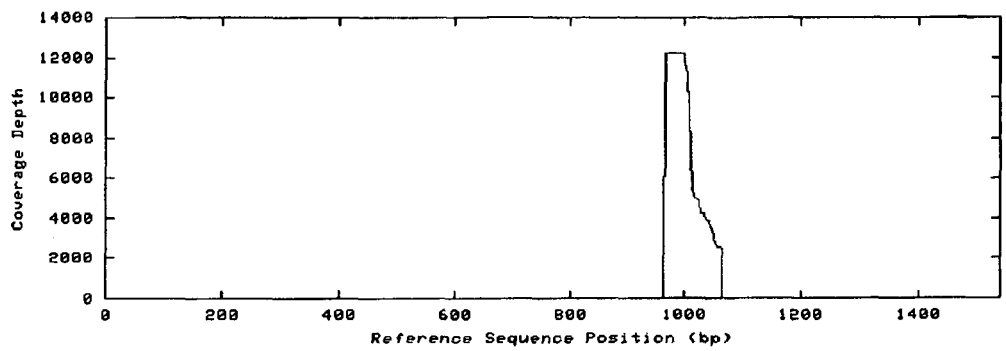
Figure 7:
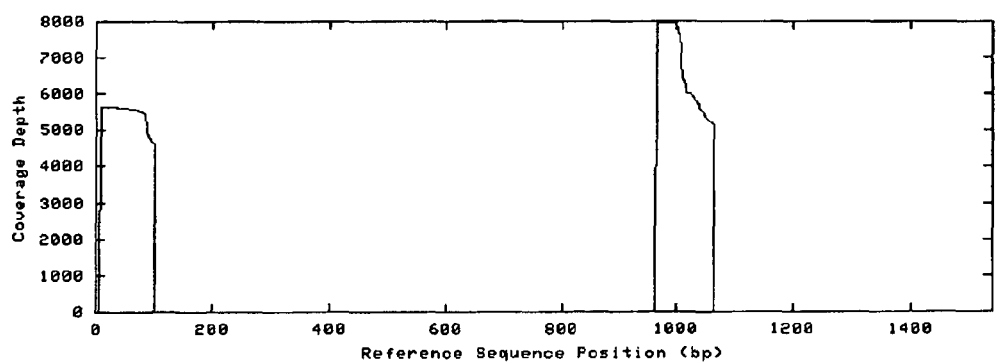

For the sequences generated with the V1 specific primers, of the 13702 sequences generated, 87.75% or 11973 reads mapped to the genome with an alignment score less than 1.0, and a read length greater than 21 bases. A graphical display showing the location of the reads mapping to the 1.6 Kb 16S gene fragment is shown in FIG. 7A, indicating roughly 12,000 reads mapping to the first 100 bases of the 16S gene.

BLASTing the unmodified consensus sequence (AAGAGTTTtGATCATGGCTCAGATTGAACGCTGGCGG CAGGCCTAACACATGCAAG TCGAACGGTAACAGGA (SEQ ID NO:17)) against the 16S database (world wide web at greengenes.llnl.gov) matched *Escherichia coli* as the first known organism

```
>lcl|009704 X80724 Escherichia coli str. Seattle 1946 ATCC 25922.
Length = 1452
Score = 125 bits (63), Expect = 1e-28
Identities = 70/71 (98%), Gaps = 1/71 (1%)
Strand = Plus/Plus Query: 7    tttgatcatggctcagattgaacgctggcggcaggcctaacacatgcaagtcgaacggta 66
            ||||||||||||||||||||||||||||||||||||||||||||||||||||||||||||
Sbjct: 3    tttgatcatggctcagattgaacgctggcggcaggcctaacacatgcaagtcgaacggta 62

Query: 67   acgaggaacga 77 (SEQ ID NO: 18)
            || ||||||||
Sbjct: 63   ac-aggaacga 72 (SEQ ID NO: 19)

>lcl|090202 AY319393 Escherichia coli strain 5.2 16S ribosomal RNA
gene, partial sequence
Length = 1399
Score =   123 bits (62), Expect = 5e-28
Identities = 62/62 (100%)
Strand = Plus/Plus
```

The V1 consensus sequence was edited to AAGAGTTT TGATCATGGCTCAGATTGAACGCTGGCGGCAGGCC TAACACATGCAAGTCGAACGGTAACAGGA (SEQ BD NO:20), as the fourth "T" at position 9 (marked in bold and underline) of a homopolymer stretch was reviewed and removed, based on an exceedingly low confidence score. The BLAST results of the edited V1 sequence demonstrated improved hits against *Escherichia coli* 16S genes.

of V1 reads that mapped, and this may reveal a greater diverge between the V3 sample and reference sequences than between the V1 sample and reference sequences. The consensus sequence: CAACGCGAAGAACCTTACCTGGTCT- TGACATCCACGAAGTTTACTAGAGATGAG AATGT- GCCGTTCGGGAACCGGTGAGACAGGTGCTGCATGG CTGTCGTCTg (SEQ ID NO:23), mapped to regions 966- 1067 of the reference genome as shown in FIG. 7B.

```
>lcl|076948 AE016770 Escherichia coli CFT073 section 16 of 18 of the complete
genome
Length = 1542
Score = 141 bits (71), Expect = 1e-33
Identities = 71/71 (100%)
Strand = Plus/Plus Query: 1    aagagtttgatcatggctcagattgaacgctggcggcaggcctaacacatgcaagtcgaa 60
            ||||||||||||||||||||||||||||||||||||||||||||||||||||||||||||
Sbjct: 6    aagagtttgatcatggctcagattgaacgctggcggcaggcctaacacatgcaagtcgaa 65

Query: 61   cggtaacagga 71 (SEQ ID NO: 21)
            |||||||||||
Sbjct: 66   cggtaacagga 76 (SEQ ID NO: 22)
```

Similar results were obtained with the V3 specific primers. Of the 17329 reads, 71.00% mapped to the 16S reference genome under identical analysis conditions as used with the V1 templates above. This is a lower number than the 87.75%

Unlike the V1 sequence BLAST results from the unmodified consensus sequence did not match *Escherichia coli* as the first known organism, but rather as the second organism.

```
>lcl|088104 AJ567617 Escherichia coli partial 16S rRNA gene, clone
MBAE104
Length = 1497
Score = 147 bits (74), Expect = 3e-35
Identities = 98/102 (96%), Gaps = 3/102 (2%)
Strand = Plus/Plus Query: 1      caacgcgaagaaccttacctggtcttgacatccacgaagtttactagagatgagaatgtg 60
              ||||||||||||||||||||||||||||||||||||||||| | ||||||||||||||||
Sbjct: 956    caacgcgaagaaccttacctggtcttgacatccacgaagttttc-agagatgagaatgtg 1014

Query: 61     ccgttcgggaaccggtgagacaggtgctgcatggctgtcgtc 102 (SEQ ID NO: 24)
              || ||||||||||  ||||||||||||||||||||||||||||
Sbjct: 1015   cc-ttcgggaacc-gtgagacaggtgctgcatggctgtcgtc 1054 (SEQ ID NO: 25)
```

The consensus sequence was reviewed and edited to CAACGCGAAGAACCTTACCTGGTCTTGA-CATCCACGAAGTTTACAGAGATGAGA ATGTGCCGT-TCGGGAACCGTGAGACAGGTGCTGCATG-GCTGTCGTCTg (SEQ ID NO:26) (with the removal of two bases) based on the confidence scores, and reBLASTed. The BLAST resulted in the highest ranked hit occurring against *E. coli*.

```
>lcl|088104 AJ567617 Escherichia coli partial 16S rRNA gene, clone
MBAE104
Length = 1497
Score = 174 bits (88), Expect = 1e-43
Identities = 98/100 (98%), Gaps = 1/100 (1%)
Strand = Plus/Plus
Query: 1     caacgcgaagaaccttacctggtcttgacatccacgaagtttacagagatgagaatgtgc 60
             ||||||||||||||||||||||||||||||||||||||||| ||||||||||||||||||
Sbjct: 956   caacgcgaagaaccttacctggtcttgacatccacgaagttttcagagatgagaatgtgc 1015

Query: 61    cgttcgggaaccgtgagacaggtgctgcatggctgtcgtc 100 (SEQ ID NO: 27)
             | |||||||||||||||||||||||||||||||||||||
Sbjct: 1016  c-ttcgggaaccgtgagacaggtgctgcatggctgtcgtc 1054 (SEQ ID NO: 28)
```

A second experiment was conducted to demonstrate the ability to use mixed PCR primers on unprocessed bacterial cells, where the *E. coli* cells were grown to saturation and 1 µl of a 1:1000 dilution of the bacterial broth was added to the EBCA reaction mix in lieu of template. The primers used in the EBCA reaction consisted of V1- and V3-specific bipartite primers at 0.04 µM each, as well as the forward and reverse 454 amplification primers at 0.625 and 0.04 µM respectively. Otherwise, the EBCA protocol outlined below was followed.

The data showed that V1 and V3 regions could be successfully amplified, sequenced and distinguished simultaneously from an untreated pool of bacterial cells. Of the 15484 reads, 87.66% mapped to the 16S reference genome, with the sequences located at the distinctive V1 and V3 positions shown in FIG. 7C.

Figure 8:
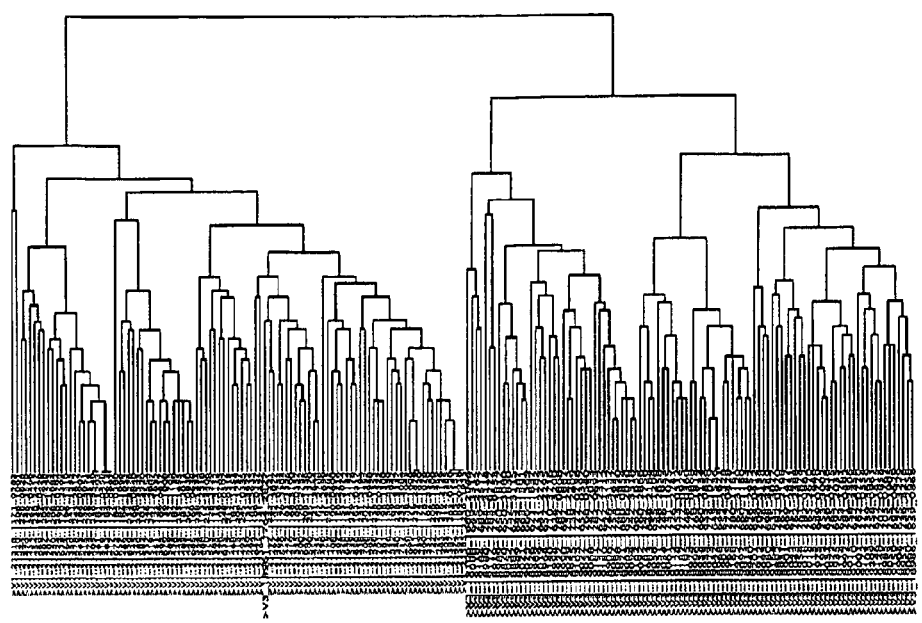
FIG. 8 depicts a phylogentic tree which clearly discriminates between the V1 (shorter length on left half of figure) and the V3 (longer length on right half of figure) sequences in all but 1 of the 200 sequences.

The ability to distinguish between V1 and V3 sequences was assessed by pooling 100 reads of both V1 and V3 sequences, and converting the raw signal data into a binary string, with a "1" indicating that a base was present at a given flow, and a "0" indicating that it was absent. Homopolymer stretches were collapsed into a single positive value, so that "A", "AA", and "AAAAA" (SEQ ID NO:29) all received an identical score of "1". The collapsed binary strings were then clustered via the Hierarchical Ordered Partitioning and Collapsing Hybrid (HOPACH) methodology (Pollard and van der Laan 2005) in the R statistical package (Team 2004). The resulting phylogentic tree, shown in FIG. 8, clearly discriminates between the V1 (shorter length red labels) and the V3 (longer length blue labels) sequences in all but 1 of the 200 sequences.

The ability to discriminate this clearly between two similar regions from the same gene within the same organism suggest that this technology should prove adept at discriminating between variable regions from distinct organisms, providing a valuable diagnostic tool.

Example 4

EBCA Protocol 4.1 Preparation of DNA Capture Beads

Packed beads from a 1 mL N-hydroxysuccinimide ester (NHS)-activated Sepharose HP affinity column (Amersham Biosciences, Piscataway, N.J.) were removed from the column and activated as described in the product literature (Amersham Pharmacia Protocol #71700600AP). Twenty-five microliters of a 1 mM amine-labeled HEG capture primer (5'-Amine-3 sequential 18-atom hexa-ethyleneglycol spacers CCATCTGTTGCGTGCGTGTC-3' (SEQ ID NO:30)) (IDT Technologies, Coralville, Iowa, USA) in 20 mM phosphate buffer, pH 8.0, were bound to the beads, after which 25-36 µm beads were selected by serial passage through 36 and 25 µm pore filter mesh sections (SefarAmerica, Depew, N.Y., USA). DNA capture beads that passed through the first filter, but were retained by the second were collected in bead storage buffer (50 mM Tris, 0.02% Tween, 0.02% sodium azide, pH 8), quantitated with a Multisizer 3 Coulter Counter (Beckman Coulter, Fullerton, Calif., USA) and stored at 4° C. until needed.

4.2 Binding Template Species to DNA Capture Beads

Template molecules were annealed to complementary primers on the DNA Capture beads in a UV-treated laminar flow hood. Six hundred thousand DNA capture beads suspended in bead storage buffer were transferred to a 200 µL PCR tube, centrifuged in a benchtop mini centrifuge for 10 seconds, the tube rotated 180° and spun for an additional 10 seconds to ensure even pellet formation. The supernatant was then removed, and the beads washed with 200 µL of Annealing Buffer (20 mM Tris, pH 7.5 and 5 mM magnesium acetate), vortexed for 5 seconds to resuspend the beads, and pelleted as above. All but approximately 10 µL of the supernatant above the beads were removed, and an additional 200 µL of Annealing Buffer were added. The beads were vortexed again for 5 seconds, allowed to sit for 1 minute, then pelleted as above. All but 10 µL of supernatant were discarded, and 0.48 µL of $2 \times 10^7$ molecules per µL template library were added to the beads. The tube was vortexed for 5 seconds to mix the contents, after which the templates were annealed to the beads in a controlled denaturation/annealing program preformed in an MJ thermocycler (5 minutes at 80° C., followed by a decrease by 0.1° C./sec to 70° C., 1 minute at 70° C., decrease by 0.1° C./sec to 60° C., hold at 60° C. for 1 minute, decrease by 0.1° C./sec to 50° C., hold at 50° C. for 1 minute, decrease by 0.1° C./sec to 20° C., hold at 20° C.). Upon completion of the annealing process the beads were stored on ice until needed.

4.3 PCR Reaction Mix Preparation and Formulation

To reduce the possibility of contamination, the PCR reaction mix was prepared in a in a UV-treated laminar flow hood located in a PCR clean room. For each 600,000 bead emulsion PCR reaction, 225 µL of reaction mix (1× Platinum HiFi Buffer (Invitrogen), dNTPs (Pierce), 2.5 mM MgSO$_4$ (Invitrogen), 0.1% Acetylated, molecular biology grade BSA (Sigma), 0.01% Tween-80 (Acros Organics), 0.003 U/µL thermostable pyrophosphatase (NEB), 0.625 µM forward (5'-CGTTTCCCCTGTGTGCCTTG-3' (SEQ ID NO:31)) and 0.039 μM reverse primers (5'-CCATCTGTTGCGTGCGT-GTC-3' (SEQ ID NO:32)) (IDT Technologies, Coralville, Iowa, USA) and 0.15 U/μL Platinum Hi-Fi Taq Polymerase (Invitrogen)) were prepared in a 1.5 mL tube. Twenty-five microliters of the reaction mix were removed and stored in an individual 200 μL PCR tube for use as a negative control. Both the reaction mix and negative controls were stored on ice until needed. Additionally, 240 μL of mock amplification mix (1× Platinum HiFi Buffer (Invitrogen), 2.5 mM $MgSO_4$ (Invitrogen), 0.1% BSA, 0.01% Tween) for every emulsion were prepared in a 1.5 mL tube, and similarly stored at room temperature until needed.

4.4 Emulsification and Amplification

The emulsification process creates a heat-stable water-in-oil emulsion with approximately 10,000 discrete PCR microreactors per microliter which serve as a matrix for single molecule, clonal amplification of the individual molecules of the target library. The reaction mixture and DNA capture beads for a single reaction were emulsified in the following manner: in a UV-treated laminar flow hood, 200 μL of PCR solution were added to the tube containing the 600,000 DNA capture beads. The beads were resuspended through repeated pipette action, after which the PCR-bead mixture was permitted to sit at room temperature for at least 2 minutes, allowing the beads to equilibrate with the PCR solution. Meanwhile, 400 μL of Emulsion Oil (60% (w/w) DC 5225C Formulation Aid (Dow Chemical CO, Midland, Mich.), 30% (w/w) DC 749 Fluid (Dow Chemical CO, Midland, Mich.), and 30% (w/w) Ar20 Silicone Oil (Sigma)) were aliquotted into a flat-topped 2 mL centrifuge tube (Dot Scientific). The 240 μL of mock amplification mix were then added to 400 μL of emulsion oil, the tube capped securely and placed in a 24 well TissueLyser Adaptor (Qiagen) of a TissueLyser MM300 (Retsch GmbH & Co. KG, Haan, Germany). The emulsion was homogenized for 5 minutes at 25 oscillations/sec to generate the extremely small emulsions, or "microfines" that confer additional stability to the reaction.

During the microfine formation, one hundred and sixty microliters of the PCR amplification mix were added to the mixture of annealed templates and DNA capture beads. The combined beads and PCR reaction mix were briefly vortexed and allowed to equilibrate for 2 minutes. After the microfines had been formed, the amplification mix, templates and DNA capture beads were added to the emulsified material. The TissueLyser speed was reduced to 15 oscillations per second and the reaction mix homogenized for 5 minutes. The lower homogenization speed created water droplets in the oil mix with an average diameter of 100 to 150 μm, sufficiently large to contain DNA capture beads and amplification mix.

The emulsion was aliquotted into 7 to 8 separate PCR tubes each containing roughly 80 μL. The tubes were sealed and placed in a MJ thermocycler along with the 25 μl negative control made previously. The following cycle times were used: 1×(4 minutes at 94° C.)–Hotstart Initiation, 40×(30 seconds at 94° C., 60 seconds at 58° C., 90 seconds at 68° C.)–Amplification, 13×(30 seconds at 94° C., 360 seconds at 58° C.)—Hybridization Extension. After completion of the PCR program, the reactions were removed and the emulsions either broken immediately (as described below) or the reactions stored at 10° C. for up to 16 hours prior to initiating the breaking process.

4.5 Breaking the Emulsion and Recovery of Beads

Fifty microliters of isopropyl alcohol (Fisher) were added to each PCR tube containing the emulsion of amplified material, and vortexed for 10 seconds to lower the viscosity of the emulsion. The tubes were centrifuged for several seconds in a microcentrifuge to remove any emulsified material trapped in the tube cap. The emulsion-isopropyl alcohol mix was withdrawn from each tube into a 10 mL BD-Disposable Syringe (Fisher Scientific) fitted with a blunt 16 gauge blunt needle (Brico Medical Supplies). An additional 50 μL of isopropyl alcohol were added to each PCR tube, vortexed, centrifuged as before, and added to the contents of the syringe. The volume inside the syringe was increased to 9 mL with isopropyl alcohol, after which the syringe was inverted and 1 mL of air was drawn into the syringe to facilitate mixing the isopropanol and emulsion. The blunt needle was removed, a 25 mm Swinlock filter holder (Whatman) containing 15 μm pore Nitex Sieving Fabric (Sefar America, Depew, N.Y., USA) attached to the syringe luer, and the blunt needle affixed to the opposite side of the Swinlock unit.

The contents of the syringe were gently but completely expelled through the Swinlock filter unit and needle into a waste container with bleach. Six milliliters of fresh isopropyl alcohol were drawn back into the syringe through the blunt needle and Swinlock filter unit, and the syringe inverted 10 times to mix the isopropyl alcohol, beads and remaining emulsion components. The contents of the syringe were again expelled into a waste container, and the wash process repeated twice with 6 mL of additional isopropyl alcohol in each wash. The wash step was repeated with 6 mL of 80% Ethanol/1× Annealing Buffer (80% Ethanol, 20 mM Tris-HCl, pH 7.6, 5 mM Magnesium Acetate). The heads were then washed with 6 mL of 1× Annealing Buffer with 6.1% Tween (0.1% Tween-20, 20 mM Tris-HCl, pH 7.6, 5 mM. Magnesium Acetate), followed by a 6 mL wash with picopure water.

After expelling the final wash into the waste container, 1.5 mL of 1 mM EDTA were drawn into the syringe, and the Swinlock filter unit removed and set aside. The contents of the syringe were serially transferred into a 1.5 mL centrifuge tube. The tube was periodically centrifuged for 20 seconds in a minifuge to pellet the beads and the supernatant removed, after which the remaining contents of the syringe were added to the centrifuge tube. The Swinlock unit was reattached to the filter and 1.5 mL of EDTA drawn into the syringe. The Swinlock filter was removed for the final time, and the beads and EDTA added to the centrifuge tube, pelletting the beads and removing the supernatant as necessary.

4.6 Second-Strand Removal

Amplified DNA, immobilized on the capture beads, was rendered single stranded by removal of the secondary strand through incubation in a basic melt solution. One mL of freshly prepared Melting Solution (0.125 M NaOH, 0.2 M NaCl) was added to the beads, the pellet resuspended by vortexing at a medium setting for 2 seconds, and the tube placed in a Thermolyne LabQuake tube roller for 3 minutes. The beads were then pelleted as above, and the supernatant carefully removed and discarded. The residual melt solution was then diluted by the addition of 1 mL Annealing Buffer (20 mM Tris-Acetate, pH 7.6, 5 mM Magnesium Acetate), after which the beads were vortexed at medium speed for 2 seconds, and the beads pelleted, and supernatant removed as before. The Annealing Buffer wash was repeated, except that only 800 μL of the Annealing Buffer were removed after centrifugation. The beads and remaining Annealing Buffer were transferred to a 0.2 mL PCR tube, and either used immediately or stored at 4° C. for up to 48 hours before continuing with the subsequent enrichment process.

4.7 Enrichment of Beads

Up to this point the bead mass was comprised of both beads with amplified, immobilized DNA strands, and null beads with no amplified product. The enrichment process was utilized to selectively capture beads with sequenceable amounts of template DNA while rejecting the null beads.

The single stranded beads from the previous step were pelleted by 10 second centrifugation in a benchtop mini centrifuge, after which the tube was rotated 180° and spun for an additional 10 seconds to ensure even pellet formation. As much supernatant as possible was then removed without disturbing the beads. Fifteen microliters of Annealing Buffer were added to the beads, followed by 2 µL of 100 µM biotinylated, 40 base HEG enrichment primer (5' Biotin-18-atom hexa-ethyleneglycol spacer-CGTTTCCCCTGTGTGCCT-TGCCATCTGTTCCCTCCCTGTC-3' (SEQ ID NO:33), IDT Technologies, complementary to the combined amplification and sequencing sites (each 20 bases in length) on the 3'-end of the bead-immobilized template. The solution was mixed by vortexing at a medium setting for 2 seconds, and the enrichment primers annealed to the immobilized DNA strands using a controlled denaturation/annealing program in an MJ thermocycler (30 seconds at 65° C., decrease by 0.1° C./sec to 58° C., 90 seconds at 58° C., and a 10° C. hold).

While the primers were annealing, a stock solution of SeraMag-30 magnetic streptavidin beads (Seradyn, Indianapolis, Ind., USA) was resuspended by gentle swirling, and 20 µL of SeraMag beads were added to a 1.5 mL microcentrifuge tube containing 1 mL of Enhancing Fluid (2 M NaCl, 10 mM Tris-HCl, 1 mM EDTA, pH 7.5). The SeraMag bead mix was vortexed for 5 seconds, and the tube placed in a Dynal MPC-S magnet, pelletting the paramagnetic beads against the side of the microcentrifuge tube. The supernatant was carefully removed and discarded without disturbing the SeraMag beads, the tube removed from the magnet, and 100 µL of enhancing fluid were added. The tube was vortexed for 3 seconds to resuspend the beads, and the tube stored on ice until needed.

Upon completion of the annealing program, 100 µL of Annealing Buffer were added to the PCR tube containing the DNA Capture beads and enrichment primer, the tube vortexed for 5 seconds, and the contents transferred to a fresh 1.5 mL microcentrifuge tube. The PCR tube in which the enrichment primer was annealed to the capture beads was washed once with 200 µL of annealing buffer, and the wash solution added to the 1.5 mL tube. The beads were washed three times with 1 mL of annealing buffer, vortexed for 2 seconds, pelleted as before, and the supernatant carefully removed. After the third wash, the beads were washed twice with 1 mL of ice cold enhancing fluid, vortexed, pelleted, and the supernatant removed as before. The beads were then resuspended in 150 µL ice cold enhancing fluid and the bead solution added to the washed SeraMag beads.

The bead mixture was vortexed for 3 seconds and incubated at room temperature for 3 minutes on a LabQuake tube roller, while the streptavidin-coated SeraMag beads bound to the biotinylated enrichment primers annealed to immobilized templates on the DNA capture beads. The beads were then centrifuged at 2,000 RPM for 3 minutes, after which the beads were gently "flicked" until the beads were resuspended. The resuspended beads were then placed on ice for 5 minutes. Following the incubation on ice, cold Enhancing Fluid was added to the beads to a final volume of 1.5 mL. The tube inserted into a Dynal MPC-S magnet, and the beads were left undisturbed for 120 seconds to allow the beads to pellet against the magnet, after which the supernatant (containing excess SeraMag and null DNA capture beads) was carefully removed and discarded.

The tube was removed from the MPC-S magnet, 1 mL of cold enhancing fluid added to the beads, and the beads resuspended with gentle flicking. It was essential not to vortex the beads, as vortexing may break the link between the SeraMag and DNA capture beads. The beads were returned to the magnet, and the supernatant removed. This wash was repeated three additional times to ensure removal of all null capture beads. To remove the annealed enrichment primers and SeraMag beads from the DNA capture beads, the beads were resuspended in 1 mL of melting solution, vortexed for 5 seconds, and pelleted with the magnet. The supernatant, containing the enriched beads, was transferred to a separate 1.5 mL microcentrifuge tube, the beads pelleted and the supernatant discarded. The enriched beads were then resuspended in 1× Annealing Buffer with 0.1% Tween-20. The beads were pelleted on the MPC again, and the supernatant transferred to a fresh 1.5 mL tube, ensuring maximal removal of remaining SeraMag beads. The beads were centrifuged, after which the supernatant was removed, and the beads washed 3 times with 1 mL of 1× Annealing Buffer. After the third wash, 800 µL of the supernatant were removed, and the remaining beads and solution transferred to a 0.2 mL PCR tube.

The average yield for the enrichment process was 33% of the original beads added to the emulsion, or 198,000 enriched beads per emulsified reaction. As the 60×60 mm PTP format required 900,000 enriched beads, five 600,000 bead emulsions were processed per 60×60 mm PTP sequenced.

4.8 Sequencing Primer Annealing

The enriched beads were centrifuged at 2,000 RPM for 3 minutes and the supernatant decanted, after which 15 µL of annealing buffer and 3 µL of sequencing primer (100 mM SAD1F (5'-GCC TCC CTC GCG CCA-3' (SEQ ID NO:34), IDT Technologies), were added. The tube was then vortexed for 5 seconds, and placed in an MJ thermocycler for the following 4 stage annealing program: 5 minutes at 65° C., decrease by 0.1° C./sec to 50° C., 1 minute at 50° C., decrease by 0.1° C./sec to 40° C., hold at 40° C. for 1 minute, decrease by 0.1° C./sec to 15° C., hold at 15° C.

Upon completion of the annealing program, the beads were removed from thermocycler and pelleted by centrifugation for 10 seconds, rotating the tube 180°, and spun for an additional 10 seconds. The supernatant was discarded, and 200 µL of annealing buffer were added. The beads were resuspended with a 5 second vortex, and the beads pelleted as before. The supernatant was removed, and the beads resuspended in 100 µL annealing buffer, at which point the beads were quantitated with a Multisizer 3 Coulter Counter. Beads were stored at 4° C. and were stable for at least one week.

4.9 Incubation of DNA Beads with Bst DNA Polymerase, Large Fragment and SSB Protein Bead wash buffer (100 ml) was prepared by the addition of apyrase (Biotage) (final activity 8.5 units/liter) to 1× assay buffer containing 0.1% BSA. The fiber optic slide was removed from picopure water and incubated in bead wash buffer. Nine hundred thousand of the previously prepared DNA beads were centrifuged and the supernatant was carefully removed. The beads were then incubated in 1290 µl of bead wash buffer containing 0.4 mg/mL polyvinyl pyrrolidone (MW 360,000), 1 mM DTT, 175 µg of *E. coli* single strand binding protein (SSB) (United States Biochemicals) and 7000 units of Bst DNA polymerase, Large Fragment (New England Biolabs). The beads were incubated at room temperature on a rotator for 30 minutes.

4.10 Preparation of Enzyme Beads and Micro-Particle Fillers

UltraGlow Luciferase (Promega) and Bst ATP sulfurylase were prepared in house as biotin carboxyl carrier protein (BCCP) fusions. The 87-aminoacid BCCP region contains a lysine residue to which a biotin is covalently linked during the in vivo expression of the fusion proteins in *E. coli*. The biotinylated luciferase (1.2 mg) and sulfurylase (0.4 mg) were premixed and bound at 4° C. to 2.0 mL of Dynal M280 paramagnetic beads (10 mg/mL, Dynal SA, Norway) according to manufacturer's instructions. The enzyme bound beads were washed 3 times in 2000 µL of bead wash buffer and resuspended in 2000 µL of bead wash buffer.

Seradyn microparticles (Powerbind SA, 0.8 µm, 10 mg/mL, Seradyn Inc) were prepared as follows: 1050 µL of the stock were washed with 1000 µL of 1× assay buffer containing 0.1% BSA. The microparticles were centrifuged at 9300 g for 10 minutes and the supernatant removed. The wash was repeated 2 more times and the microparticles were resuspended in 1050 µL of 1× assay buffer containing 0.1% BSA. The beads and microparticles are stored on ice until use.

4.11 Bead Deposition

The Dynal enzyme beads and Seradyn microparticles were vortexed for one minute and 1000 µL of each were mixed in a fresh microcentrifuge tube, vortexed briefly and stored on ice. The enzyme/Seradyn beads (1920 µl) were mixed with the DNA beads (1300 µl) and the final volume was adjusted to 3460 µL with bead wash buffer. Beads were deposited in ordered layers. The fiber optic slide was removed from the bead wash buffer and Layer 1, a mix of DNA and enzyme/Seradyn beads, was deposited. After centrifuging, Layer 1 supernatant was aspirated off the fiber optic slide and Layer 2, Dynal enzyme beads, was deposited. This section describes in detail how the different layers were centrifuged.

Layer 1. A gasket that creates two 30×60 mm active areas over the surface of a 60×60 mm fiber optic slide was carefully fitted to the assigned stainless steel dowels on the jig top. The fiber optic slide was placed in the jig with the smooth unetched side of the slide down and the jig top/gasket was fitted onto the etched side of the slide. The jig top was then properly secured with the screws provided, by tightening opposite ends such that they are finger tight. The DNA-enzyme bead mixture was loaded on the fiber optic slide through two inlet ports provided on the jig top. Extreme care was taken to minimize bubbles during loading of the bead mixture. Each deposition was completed with one gentle continuous thrust of the pipette plunger. The entire assembly was centrifuged at 2800 rpm in a Beckman Coulter Allegra 6 centrifuge with GH 3.8-A rotor for 10 minutes. After centrifugation the supernatant was removed with a pipette.

Layer 2. Dynal enzyme beads (920 µL) were mixed with 2760 µL of bead wash buffer and 3400 µL of enzyme-bead suspension was loaded on the fiber optic slide as described previously. The slide assembly was centrifuged at 2800 rpm for 10 min and the supernatant decanted. The fiber optic slide is removed from the jig and stored in bead wash buffer until it is ready to be loaded on the instrument.

4.12 Sequencing on the 454 Instrument

All flow reagents were prepared in 1× assay buffer with 0.4 mg/mL polyvinyl pyrrolidone (MW 360,000), 1 mM DTT and 0.1% Tween 20. Substrate (300 µM D-luciferin (Regis) and 2.5 µM adenosine phophosulfate (Sigma)) was prepared in 1× assay buffer with 0.4 mg/mL polyvinyl pyrrolidone (MW 360,000), 1 mM DTT and 0.1% Tween 20. Apyrase wash is prepared by the addition of apyrase to a final activity of 8.5 units per liter in 1× assay buffer with 0.4 mg/mL polyvinyl pyrrolidone (MW 360,000), 1 mM DTT and 0.1% Tween 20. Deoxynucleotides dCTP, dGTP and dTTP (GE Biosciences) were prepared to a final concentration of 6.5 µM, α-thio deoxyadenosine triphosphate (dATPαS, Biolog) and sodium pyrophosphate (Sigma) were prepared to a final concentration of 50 µM and 0.1 µM, respectively, in the substrate buffer.

The 454 sequencing instrument consists of three major assemblies: a fluidics subsystem, a fiber optic slide cartridge/flow chamber, and an imaging subsystem. Reagents inlet lines, a multi-valve manifold, and a peristaltic pump form part of the fluidics subsystem. The individual reagents are connected to the appropriate reagent inlet lines, which allows for reagent delivery into the flow chamber, one reagent at a time, at a pre-programmed flow rate and duration. The fiber optic slide cartridge/flow chamber has a 250 µm space between the slide's etched side and the flow chamber ceiling. The flow chamber also included means for temperature control of the reagents and fiber optic slide, as well as a light-tight housing. The polished (unetched) side of the slide was placed directly in contact with the imaging system.

The cyclical delivery of sequencing reagents into the fiber optic slide wells and washing of the sequencing reaction byproducts from the wells was achieved by a pre-programmed operation of the fluidics system. The program was written in a form of an Interface Control Language (ICL) script, specifying the reagent name (Wash, dATPαS, dCTP, dGTP, dTTP, and PPi standard), flow rate and duration of each script step. Flow rate was set at 4 mL/min for all reagents and the linear velocity within the flow chamber was approximately ~1 cm/s. The flow order of the sequencing reagents were organized into kernels where the first kernel consisted of a PPi flow (21 seconds), followed by 14 seconds of substrate flow, 28 seconds of apyrase wash and 21 seconds of substrate flow. The first PPi flow was followed by 21 cycles of dNTP flows (dC-substrate-apyrase wash-substrate dA-substrate-apyrase wash-substrate-dG-substrate-apyrase wash-substrate-dT-substrate-apyrase wash-substrate), where each dNTP flow was composed of 4 individual kernels. Each kernel is 84 seconds long (dNTP-21 seconds, substrate flow-14 seconds, apyrase wash-28 seconds, substrate flow-21 seconds); an image is captured after 21 seconds and after 63 seconds. After 21 cycles of dNTP flow, a PPi kernel is introduced, and then followed by another 21 cycles of dNTP flow. The end of the sequencing run is followed by a third PPi kernel. The total run time was 244 minutes. Reagent volumes required to complete this run are as follows: 500 mL of each wash solution, 100 mL of each nucleotide solution. During the run, all reagents were kept at room temperature. The temperature of the flow chamber and flow chamber inlet tubing is controlled at 30° C. and all reagents entering the flow chamber are pre-heated to 30° C.

Example 5

Analysis of Soil Samples

Nucleic acid was extracted from organisms in the soil for analysis using the methods of the invention. Extraction was performed using a DNA extraction kit from Epicentre (Madison, Wis., USA) following manufacturer's directions.

Briefly, five hundred and fifty microliters of Inhibitor Removal Resin was added to each empty Spin Column from Epicentre. The columns were centrifuged for one minute at 2000×g to pack the column. The flow-through was removed and another 550 ul of Inhibitor Removal Resin was added to each column followed by centrifugation for 2 minutes at 2000×g.

One hundred milligrams of soil was collected into a 1.5 ml tube and 250 ul of Soil DNA extraction buffer was added with 2 ul of Proteinase K. The solution was vortexed and 50 ul of Soil Lysis buffer was added and vortexed again. The tube was incubated at 65 C for 10 minutes and then centrifuged for 2 minutes at 1000×g. One hundred and eighty microliters of the supernatant was transferred to a new tube, and 60 ul of Protein Precipitation Reagent was added with thorough mixing by inverting the tube. The tube was incubated on ice for 8 minutes and centrifuged for 8 minutes at maximum speed. One hundred to one hundred and fifty microliters of the supernatant was transferred directly onto the prepared Spin Column and the column was centrifuged for 2 minutes at 2000×g into the 1.5 ml tube. The column was discarded and the eluate was collected. 6 ul of DNA Precipitation Solution was added to the eluate and the tube was mixed by a brief vortex. Following a 5 minute room temperature incubation, the tube was centrifuged for 5 minutes at maximum speed. Supernatant was removed and the pellet was washed with 500 ul of Pellet Wash Solution. The tube was inverted to mix the solution and then centrifuged for 3 minutes at maximum speed. Supernatant was removed and the wash step was repeated. Supernatant was removed again and the final pellet was resuspended in 300 ul of TE Buffer.

The DNA sample produced may be used for the methods of the invention including, at least, the methods for detecting nucleotide frequency at a locus.

Example 6

Desgin of HIV Glade B Primers

Due to the high level of variability in the HIV genome, an alignment of a large number of sequences was compiled. The HIV sequence database maintained at Los Alamos National Laboratory was searched for HIV-1 Glade B sequences with data in the POL region (which contains the protease, reverse transcriptase, and integrase coding regions). More than 6000 sequences of high quality were aligned, and a consensus sequence generated. The sequences were then uploaded onto an application server and a mutation plot generated with the consensus sequence as the target sequence. From this plot, conserved regions were identified and primers designed to these regions.

The primers were tested initially for the ability to generate amplicons of the expected size from a panel of four reference sequences (1A, 4A, 8A, and 4B). The final primer set was chosen to give multiple coverage of all regions of interest in the protease and the reverse transcriptase. In addition, four of the primers were designed to each be a mix of two sequences, differing in one nucleotide position deemed to be crucial for primer binding and polymorphic in a large proportion (>10-30%) of sequences. This strategy allows for complete coverage in most cases even if one or two primers should fail on a given sequence. Positions of primers and amplicons are shown in these schematic in FIG. 12.

Example 7

Testing of Amplicon Strategy

The amplicon strategy of Example 6 was tested by sequencing of a total of 8 reference samples (designated 1A, 4A, 8A, 4B, 14, 15, 17, and 25). These reference samples were in the form of 1.4 Kb amplicons from nested PCR methods. Amplicons were generated from the reference samples by 15 cycles of PCR, and emulsions were set up using Amplicon A and B kits. In some instances, single amplicons were sequenced, sometimes several were mixed together at the emulsion step. Amplicon sequencing was then compared to sequencing of the exact same 1.4 Kb amplicons that had been nebulized and sequenced as random libraries. The nebulized samples were assumed to have minimal bias in terms of detecting the actual nucleotide composition at each position. In all cases, excellent correspondence was achieved between the amplicon and library sequencing mutational plots. The only problems occurred in primer binding regions due to introduction of mutations from degenerate positions and apparent suppression of sample mutations relative to the primers. Both of these problems are solved using the amplicon data analysis software, that automatically removes primer site sequences from each amplicon before analysis.

Making one long cDNA fragment and then amplifying a 1.4 Kb amplicon (uses a total of 75 cycles of nested PCR) to generate our template was sub-optimal. It involves a large number of PCR cycles, and it is not clear that the single-cDNA strategy adequately reflects the entire pool of RNA quasispecies present in a patient specimen. Thus, a strategy of making multiple cDNA fragments, currently three as illustrated in FIG. 12 (one for the protease and two for the RT—dividing the sequence in three approximately equal parts) is employed. The reactions have to be carried out separately since Superscript II (MMLV RT-derived) does not displace cDNA from RNA during synthesis and therefore introduces a bias towards the 3'-most sequence in a mixed reaction.

Consistent amplicon amplification is achieved by 40 cycles of PCR with an average yield of approximately 150 ng per amplicon. It is possible to use fewer cycles of amplification on samples with high viral load.

Example 8

HIV Variation in the Protease and RT Regions of a Subject

Figure 14:
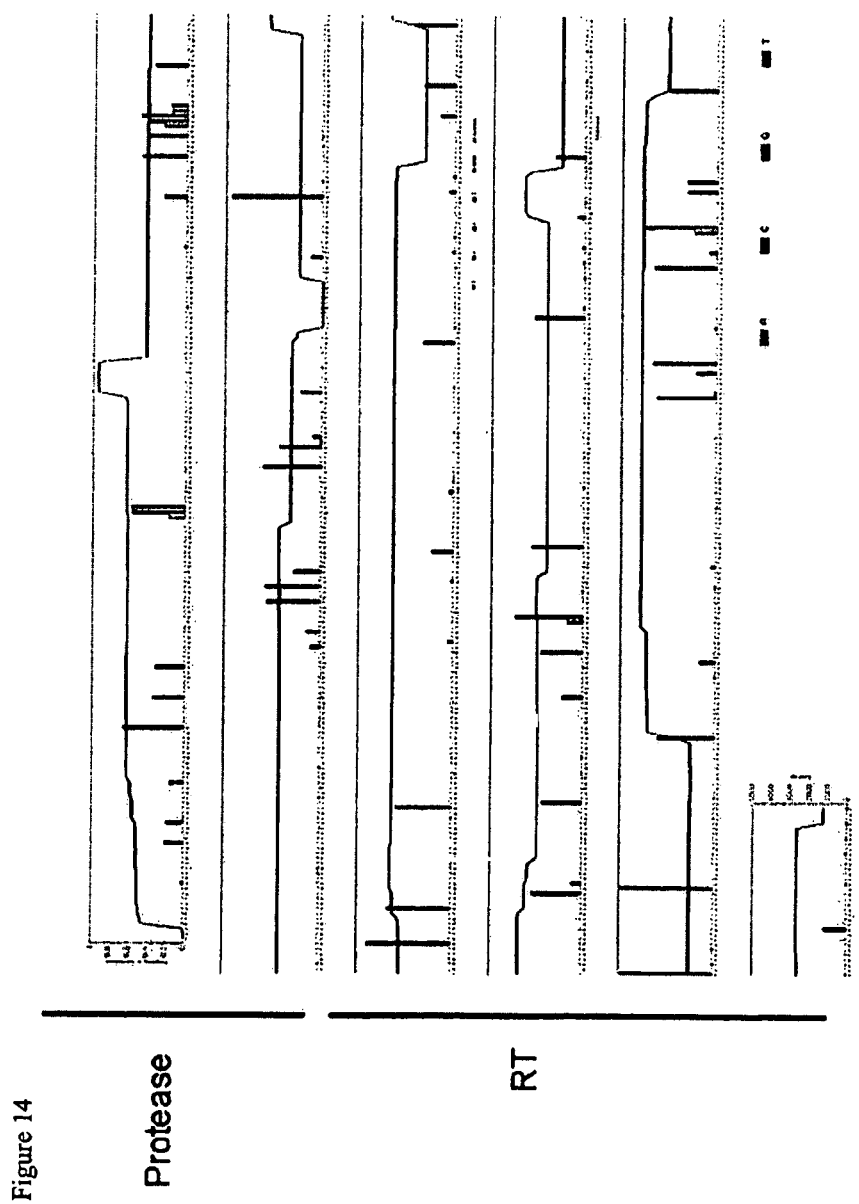
FIG. 14 depicts one embodiment of a mix of HIV quasispecies variants measured from an HIV subject.

The amplicon strategy of the described invention was tested on an HIV positive subject who possessed a number of sequence variants relative to the consensus sequence. A representation of each sequence variant including degree of variation is illustrated in FIG. 14. In FIG. 14, the "Frequency of Variation" is represented by the height of a bar at the corresponding sequence position and relative to a scale ranging from 0 (i.e. 0% frequency in the HIV subject) to 1 (i.e. 100% frequency in the HIV subject). Also, the identity of the variant nucleotide species at a corresponding sequence position in the subject is represented by a color. As is evident in FIG. 14, the particular subject has numerous variants in the protease and reverse transcriptase regions some occurring at a high frequency and a small group occurring at low frequency. It will be appreciated that not all variants are associated with deleterious effects such as the described drug resistance.

Example 9

Identification of Variant Associated with PI Drug Resistance

Figure 15:
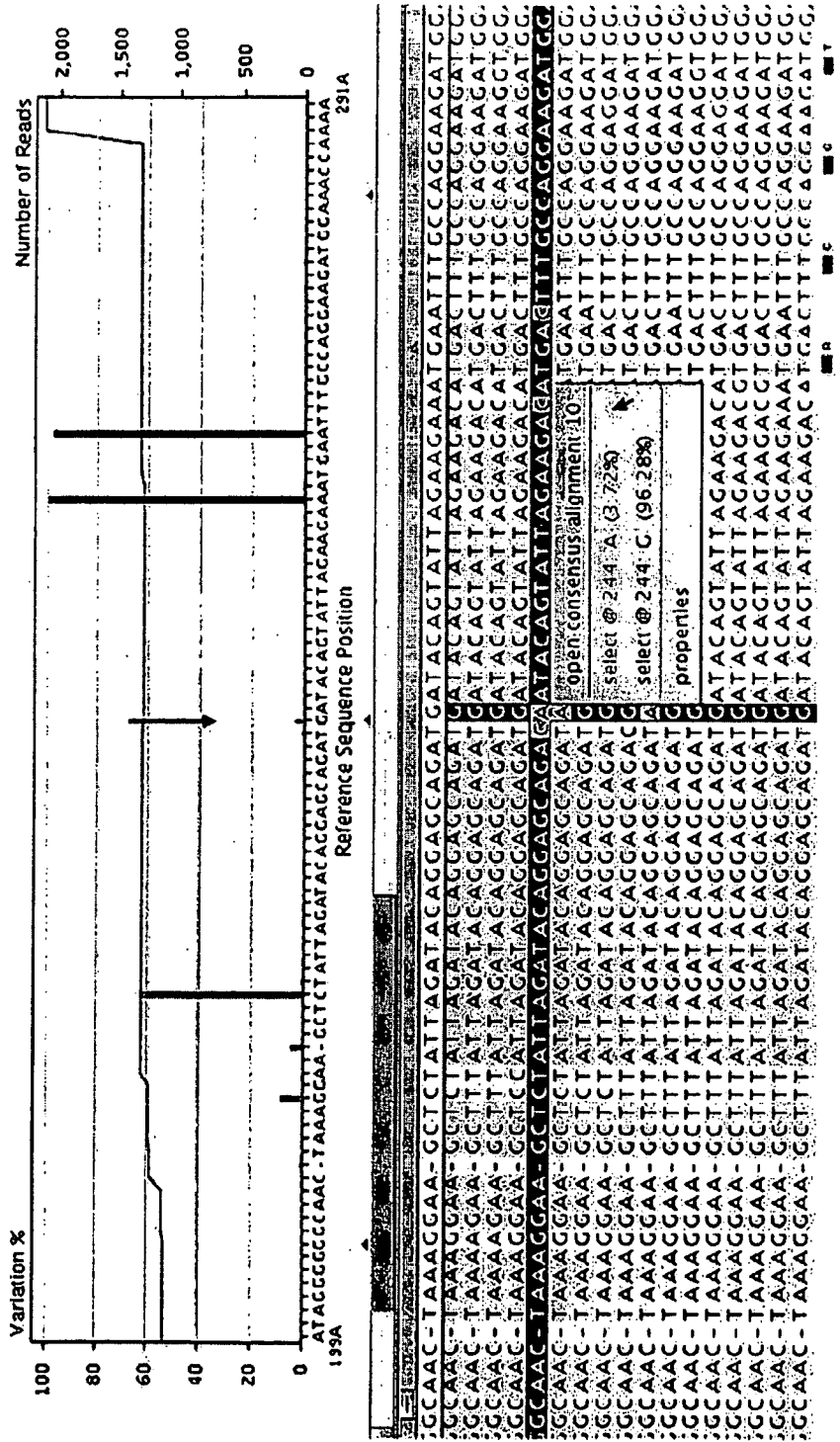
FIG. 15 depicts one embodiment of an HIV quasispecies variant (SEQ ID No: 132) associated with protease inhibitor resistance identified at a 3.7% frequency in an HIV subject sample.

The amplicon strategy of the described invention was tested on an HIV positive subject who possessed a specific sequence variant associated with resistance to a drug called Nalfinavir (marketed as Viracept® by Pfizer Inc.), which is a selective, nonpeptidic inhibitor of HIV protease. The frequency of the specific variation in the particular subject was identified to occur at 3.7% from the viral RNA molecules in a sample taken from the subject as illustrated in FIG. 15. FIG. 15 also provides an illustrative example of the alignment of amplicon sequences produced from the subject sample to the consensus sequence that shows a change from a G nucleotide species to an A' nucleotide species in 3.7% of the RNA molecules sequenced. FIG. 15 also provides an illustrative graph of the degree of variation in percentage of the number of RNA molecules sequenced in the subject sample (illustrated as number of "Reads"). The term "read" as used herein generally refers to the entire sequence data derived from a single nucleic acid template molecule that includes a clonal population of substantially identical copies of the template nucleic acid molecule. In the present example, the variant is a single nucleotide change at sequence position 244 that was found to occur in 3.7% of over 2000 sequence reads that passed quality control standards.

Example 10

Identification of Variant Associated with NNRTI Drug Resistance

Figure 16:
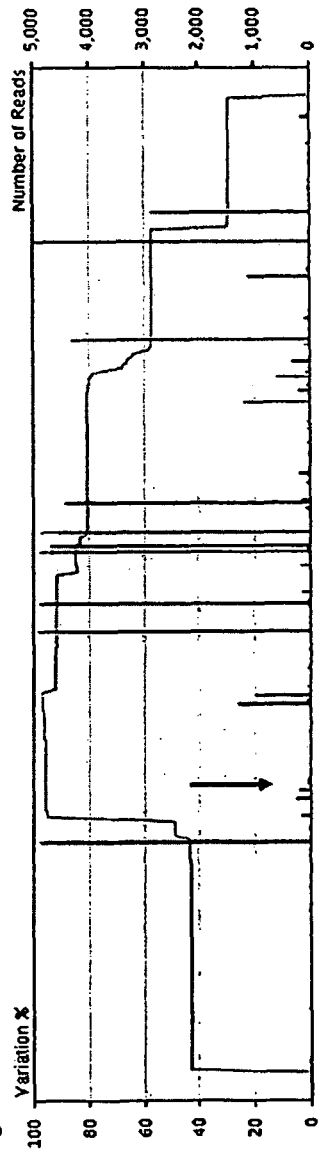
FIG. 16 depicts one embodiment of an HIV quasispecies variant associated with non-nucleoside reverse transcriptase inhibitor resistance identified at a 1.0% frequency in an HIV subject sample.

The amplicon strategy of the described invention was tested on an HIV positive subject who possessed a specific sequence variant associated with resistance to the drugs Delavirdine (marketed as Rescriptor® by Pfizer Inc.), Nevirapine (marketed as Viramune® by Boehringer Ingelheim Pharmaceuticals Inc.), Efavirenz (marketed as Sustiva® by Bristol Myers Squibb), and Etravirine® (marketed as Intelence by Tibotec Therapeutics), all of which are non-nucleoside reverse transcriptase inhibitors (NNRTI). The frequency of the specific variation in the particular subject was identified to occur at 1.0% from the viral RNA molecules in a sample taken from the subject as illustrated in FIG. 16. FIG. 16 also provides an illustrative example of the alignment of amplicon sequences from the subject sample to the consensus sequence that shows a change from a A nucleotide species to a G nucleotide species in 1.0% of the RNA molecules sequenced. FIG. 16 also provides an illustrative graph of the degree of variation in percentage of the number of RNA molecules sequenced in the subject sample (illustrated as number of "Reads"). In the present example, the variant is a single nucleotide change at sequence position 995 that was found to occur in 1.0% of about 5000 sequence reads that passed quality control standards.

Example 11

Identification of Variant Associated with NRTI Drug Resistance

Figure 17:
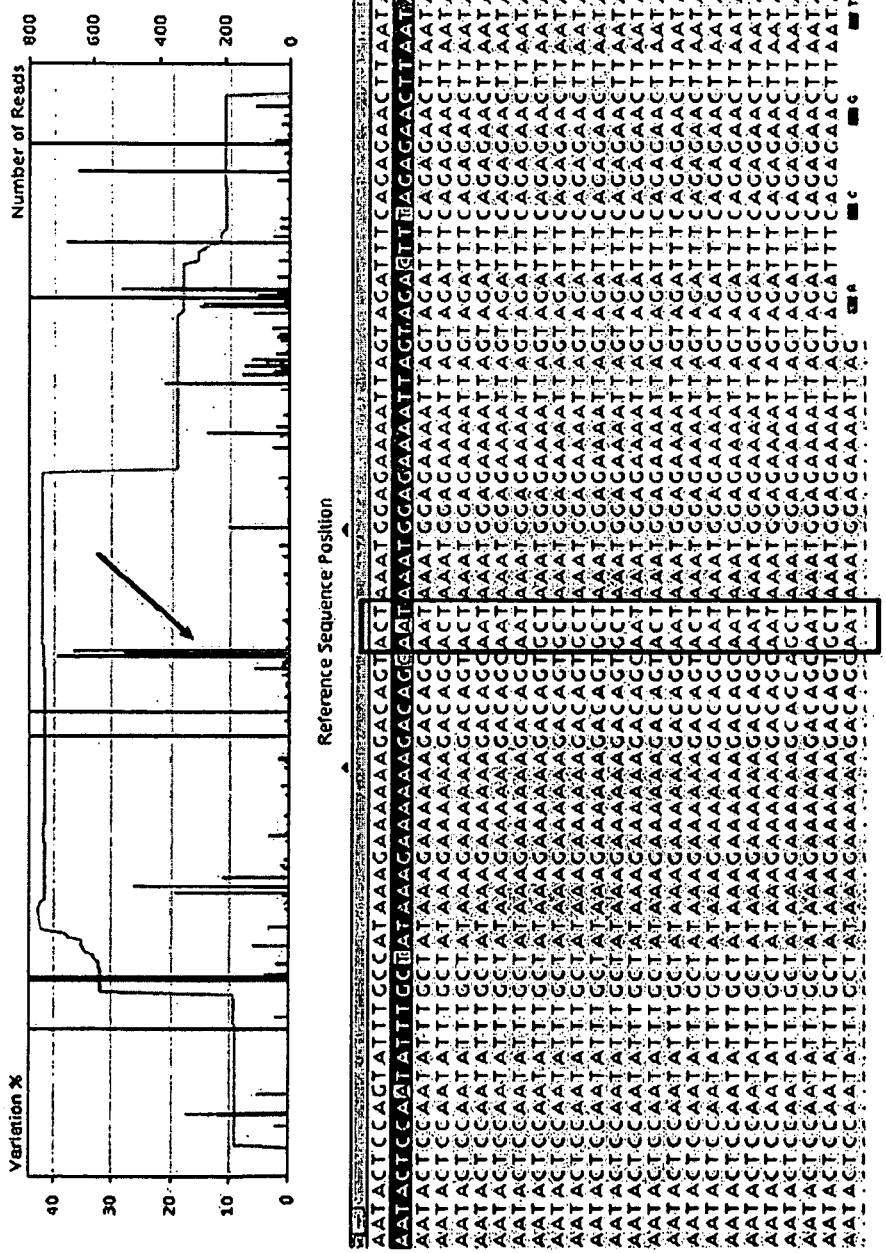
FIG. 17 depicts one embodiment of an HIV quasispecies variant associated with nucleotide/nucleoside reverse transcriptase inhibitor resistance.

The amplicon strategy of the described invention was tested on an HIV positive subject who, within a specific codon, possessed sequence variants associated with previous resistance to nucleotide/nucleoside reverse transcriptase inhibitors (NRTI). The identified variations occurred in the first two positions of the codon, the first variant is a change from a A nucleotide species to a G nucleotide species and the second is a change from a C nucleotide species to a A nucleotide species as illustrated in FIG. 17. It will be apparent that in the example of FIG. 17 the changes in the first and second positions do not occur in the same RNA sequence, rather each occur in independent RNA molecules.

REFERENCES

BioAnalyzer User Manual (Agilent): hypertext transfer protocol://world wide web.chem.agilent.com/temp/rad31B29/00033620.pdf BioAnalyzer DNA and RNA LabChip Usage (Agilent): hypertext transfer protocol://world wide web.agilent.com/chem/labonachip BioAnalyzer RNA 6000 Ladder (Ambion): hypertext transfer protocol://world wide web.ambion.com/techlib/spec/sp_7152.pdf Biomagnetic Techniques in Molecular Biology, Technical Handbook, 3rd edition (Dynal, 1998): hypertext transfer protocol://world wide web.dynal.no/kunder/dynal/DynalPub36.nsVcb927fbab127a0ad4125683b004b011c/4908f5b 1a665858a41256adfD05779f2/$FILE/Dynabeads M-280 Streptavidin.pdf.

Dinauer et al., 2000 Sequence-based typing of HLA class II DQB1. *Tissue Antigens* 55:364.

Garcia-Martinez, J., I. Bescos, et al. (2001). "RISSC: a novel database for ribosomal 16S-23S RNA genes spacer regions." Nucleic Acids Res 29(1): 178-80.

Grahn, N., M. Olofsson, et al. (2003). "Identification of mixed bacterial DNA contamination in broad-range PCR amplification of 16S rDNA V1 and V3 variable regions by pyrosequencing of cloned amplicons." FEMS Microbiol Lett 219(1): 87-91.

Hamilton, S. C., J. W. Farchaus and M. C. Davis. 2001. DNA polymerases as engines for biotechnology. *BioTechniques* 31:370.

Jonasson, J., M. Olofsson, et al. (2002). "Classification, identification and subtyping of bacteria based on pyrosequencing and signature matching of 16S rDNA fragments." Apmis 110(3): 263-72.

MinElute kit (QIAGEN): hypertext transfer protocol://world wide web.qiagen.com/literature/handbooks/minelute/1016839_HBMinElute_Prot_Gel.pdf.

Monstein, H., S, Nikpour-Badr, et al. (2001). "Rapid molecular identification and subtyping of *Helicobacter pylori* by pyrosequencing of the 16S rDNA variable V1 and V3 regions." FEMS Microbiol Lett 199(1): 103-7.

Norgaard et al., 1997 Sequencing-based typing of HLA-A locus using mRNA and a single locus-specific PCR followed by cycle-sequencing with AmpliTaq DNA polymerse. *Tissue Antigens*. 49:455-65.

Pollard, K. S, and M. J. van der Laan (2005). "Clsuter Analysis of Genomic Data with Applications in R." U.C. Berkeley Division of Biostatistics Working Paper Series # 167.

QiaQuick Spin Handbook (QIAGEN, 2001): hypertext transfer protocol://world wide web.qiagen.com/literature/handbooks/qqspin/1016893HBQQSpin_PCR_mc_prot.pdf Quick Ligation Kit (NEB): hypertext transfer protocol://world wide web.neb.condneb/products/mod_enzymes/M2200.html.

Shimizu et al., 2002 Universal fluorescent labeling (UFL) method for automated microsatellite analysis. *DNA Res.* 9:173-78.

Steffens et al., 1997 Infrared fluorescent detection of PCR amplified gender identifying alleles. *J. Forensic Sci.* 42:452-60.

Team, R. D. C. (2004). R: A language and environment for statistical computing. Vienna, Austria, R Foundation for Statistical Computing.

Tsang et al., 2004 Development of multiplex DNA electronic microarray using a universal adaptor system for detection of single nucleotide polymorphisms. Biotechniques 36:682-88.

We claim:

1. A method for detecting low frequency occurrence of one or more HIV sequence variants associated with drug resistance comprising the steps of:
   (a) generating a plurality of cDNA species from a plurality of RNA molecules in an HIV sample;
   (b) amplifying a plurality of first amplicons from the cDNA species, wherein each first amplicon comprises a plurality of amplified copies and is amplified with a pair of nucleic acid primers specific to Clade B that define a locus of the first amplicon population wherein the pair of nucleic acid primers are selected from the group consisting of B-ACF-1 (SeqID No: 39) and B-AR (SeqID No: 36); B-ACF-2 (SeqID No: 40) and B-AR (SeqID No: 36); B-BF (SeqID No: 35) and B-BR (SeqID No: 38); B-ACF-1 (SeqID No: 39) and B-CR (SeqID No: 37); B-ACF-2 (SeqID No: 40) and B-CR (SeqID No: 37); B-1F (SeqID No: 42) and B-1R-1 (SeqID No: 44); B-1F (SeqID No: 42) and B-1R-2 (SeqID No: 45); B-2F (SeqID No: 43) and B-2R (SeqID No: 49); B-3F (SeqID No: 50) and B-3R (SeqID No: 51); B-4F (SeqID No: 41) and B-4R-1 (SeqID No: 46); B-4F (SeqID No: 41) and B-4R-2 (SeqID No: 47); B-5F (SeqID No: 48) and B-5R-1 (SeqID No: 52); and B-5F (SeqID No: 48) and B-5R-2 (SeqID No: 53);
   (c) clonally amplifying the amplified copies of the first amplicons to produce a plurality of second amplicons wherein a plurality of the second amplicons comprise an immobilized population of substantially identical copies from one of the amplified copies of first amplicons;
   (d) determining a nucleic acid sequence composition of the substantially identical copies from at least 100 of the immobilized populations in parallel on a single instrument; and
   (e) detecting one or more sequence variants that occur at a frequency of 5% or less in the nucleic acid sequence composition of the at least 100 immobilized populations; and
   (f) correlating the detected sequence variants with variation associated with HIV drug resistance.

2. The method of claim 1, wherein:
the variation associated with HIV drug resistance is known to be associated with a particular drug class or drug.

3. The method of claim 2, wherein:
the HIV drug class is selected from the group consisting of protease inhibitors, nucleotide/nucleoside reverse transcriptase inhibitors, and non-nucleoside reverse transcriptase inhibitors.

4. The method of claim 1, wherein:
the plurality of cDNA species includes 3 cDNA species.

5. The method of claim 1, wherein:
each of the 3 cDNA species have overlapping sequence composition with at least one neighboring cDNA species.

6. The method of claim 1, wherein:
the HIV sample population is derived from a single patient.

7. The method of claim 6, wherein:
the single patient is drug naïve.

8. The method of claim 6, wherein:
the single patient was previously exposed to HIV antiretorviral drug therapy.

9. The method of claim 1, wherein:
the plurality of first amplicons comprises 8 amplicons.

10. The method of claim 1, wherein:
the pair of primers for the first amplicons target regions of low mutation frequency.

11. The method of claim 1, wherein:
the locus of the first amplicon includes a region of HIV associated with protease.

12. The method of claim 1, wherein:
the locus of the first amplicon includes a region of HIV associated with reverse transcriptase.

13. The method of claim 1, wherein:
the second amplicons are amplified using a pair of general primers.

14. The method of claim 1, wherein:
each sequence variant is detected at a 99% confidence level.

15. The method of claim 1 wherein:
the nucleic acid composition of the substantially identical copies from at least 400 immobilized populations is determined and each of the detected sequence variants occur at a frequency of 1.25% or less.

16. The method of claim 1 wherein:
the nucleic acid composition of the substantially identical copies from at least 10000 immobilized populations is determined and each of the detected sequence variants occur at a frequency of 0.050% or less.

17. The method of claim 1 wherein:
the nucleic acid composition of the substantially identical copies from at least 200000 immobilized populations is determined and each of the detected sequence variants occur at a frequency of 0.003% or less.

18. The method of claim 1 wherein:
the single instrument comprises a single substrate comprising a plurality of reaction sites.

19. The method of claim 1 wherein:
the single instrument comprises a single detection device capable of detecting signals generated from a plurality of sequencing reactions.

* * * * *

SEQUENCE LISTING

<160> NUMBER OF SEQ ID NOS: 202

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcctccctcg cgccatcaga cctccctctg tgtccttaca a                    41

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gccttgccag cccgctcagg gagggaatca tactagcacc a                    41

<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcctccctcg cgccatcagt ctgacgatct ctgtcttcta acc                  43

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gccttgccag cccgctcagg ccttgaacta cacgtggct                       39

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcctccctcg cgccatcaga tttctctacc accctggc                        39

<210> SEQ ID NO 6
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
gccttgccag cccgctcaga gctcatgtct cccgaagaa                     39
```

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
gcctccctcg cgccatcaga aagccagaag aggaaaggc                     39
```

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
gccttgccag cccgctcagc ttgcagattg gtcataagg                     39
```

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
gcctccctcg cgccatcaga cagtgcaaac accaccaaa                     39
```

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
gccttgccag cccgctcagc cagtattcat ggcagggtt                     39
```

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
gcctccctcg cgcca                                               15
```

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
gccttgccag cccgc                                               15
```

```
<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcctccctcg cgccatcagg aagagtttga tcatggctca g                   41

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gccttgccag cccgctcagt tactcacccg tccgccact                      39

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcctccctcg cgccatcagg caacgcgaag aaccttacc                      39

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gccttgccag cccgctcaga cgacagccat gcagcacct                      39

<210> SEQ ID NO 17
<211> LENGTH: 72
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 17
aagagttttg atcatggctc agattgaacg ctggcggcag gcctaacaca tgcaagtcga   60
acggtaacag ga                                                      72

<210> SEQ ID NO 18
<211> LENGTH: 71
<212> TYPE: DNA
<213> ORGANISM: Escherichia coli

<400> SEQUENCE: 18
tttgatcatg gctcagattg aacgctggcg gcaggcctaa cacatgcaag tcgaacggta   60
acgaggaacg a                                                       71
```

```
<210> SEQ ID NO 19
<211> LENGTH: 70
<212> TYPE: DNA
<213> ORGANISM: Escherichia coli

<400> SEQUENCE: 19
tttgatcatg gctcagattg aacgctggcg gcaggcctaa cacatgcaag tcgaacggta      60
acaggaacga                                                             70

<210> SEQ ID NO 20
<211> LENGTH: 72
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 20
aagagttttg atcatggctc agattgaacg ctggcggcag gcctaacaca tgcaagtcga      60
acggtaacag ga                                                          72

<210> SEQ ID NO 21
<211> LENGTH: 71
<212> TYPE: DNA
<213> ORGANISM: Escherichia coli

<400> SEQUENCE: 21
aagagtttga tcatggctca gattgaacgc tggcggcagg cctaacacat gcaagtcgaa      60
cggtaacagg a                                                           71

<210> SEQ ID NO 22
<211> LENGTH: 71
<212> TYPE: DNA
<213> ORGANISM: Escherichia coli

<400> SEQUENCE: 22
aagagtttga tcatggctca gattgaacgc tggcggcagg cctaacacat gcaagtcgaa      60
cggtaacagg a                                                           71

<210> SEQ ID NO 23
<211> LENGTH: 104
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 23
caacgcgaag aaccttacct ggtcttgaca tccacgaagt ttactagaga tgagaatgtg      60
ccgttcggga accggtgaga caggtgctgc atggctgtcg tctg                      104

<210> SEQ ID NO 24
<211> LENGTH: 102
<212> TYPE: DNA
<213> ORGANISM: Escherichia coli

<400> SEQUENCE: 24
caacgcgaag aaccttacct ggtcttgaca tccacgaagt ttactagaga tgagaatgtg      60
ccgttcggga accggtgaga caggtgctgc atggctgtcg tc                        102

<210> SEQ ID NO 25
<211> LENGTH: 99
```

```
<212> TYPE: DNA
<213> ORGANISM: Escherichia coli

<400> SEQUENCE: 25
caacgcgaag aaccttacct ggtcttgaca tccacgaagt tttcagagat gagaatgtgc      60
cttcgggaac cgtgagacag gtgctgcatg gctgtcgtc                             99

<210> SEQ ID NO 26
<211> LENGTH: 102
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 26
caacgcgaag aaccttacct ggtcttgaca tccacgaagt ttacagagat gagaatgtgc      60
cgttcgggaa ccgtgagaca ggtgctgcat ggctgtcgtc tg                        102

<210> SEQ ID NO 27
<211> LENGTH: 100
<212> TYPE: DNA
<213> ORGANISM: Escherichia coli

<400> SEQUENCE: 27
caacgcgaag aaccttacct ggtcttgaca tccacgaagt ttacagagat gagaatgtgc      60
cgttcgggaa ccgtgagaca ggtgctgcat ggctgtcgtc                           100

<210> SEQ ID NO 28
<211> LENGTH: 99
<212> TYPE: DNA
<213> ORGANISM: Escherichia coli

<400> SEQUENCE: 28
caacgcgaag aaccttacct ggtcttgaca tccacgaagt tttcagagat gagaatgtgc      60
cttcgggaac cgtgagacag gtgctgcatg gctgtcgtc                             99

<210> SEQ ID NO 29
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29 aaaaa                                                                   5

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ccatctgttg cgtgcgtgtc                                                  20

<210> SEQ ID NO 31
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 31
cgtttcccct gtgtgccttg                                            20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccatctgttg cgtgcgtgtc                                            20

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgtttcccct gtgtgccttg ccatctgttc cctccctgtc                      40

<210> SEQ ID NO 34
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gcctccctcg cgcca                                                 15

<210> SEQ ID NO 35
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gcctccctcg cgccatcagt gccaggaaga tggaaacca                       39

<210> SEQ ID NO 36
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gccttgccag cccgctcagt gataaaacct ccaattcccc cta                  43

<210> SEQ ID NO 37
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gccttgccag cccgctcagg tacagtttca ataggactaa tggg        44

<210> SEQ ID NO 38
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gccttgccag cccgctcagt tgggccatcc attcctgg        38

<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcctccctcg cgccatcaga tcactctttg gcaacgacc        39

<210> SEQ ID NO 40
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gcctccctcg cgccatcaga tcactctttg gcagcgacc        39

<210> SEQ ID NO 41
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gcctccctcg cgccatcagg taccagtaaa attaaagcca ggaatgg        47

<210> SEQ ID NO 42
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gcctccctcg cgccatcagg gccattgaca gaagaaaaaa taaaagc        47

<210> SEQ ID NO 43
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcctccctcg cgccatcagg gaagttcaat taggaatacc acatcc          46

<210> SEQ ID NO 44
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gccttgccag cccgctcagg gatgtggtat tcctaattga acttcc          46

<210> SEQ ID NO 45
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gccttgccag cccgctcagg gatgtggtat tcctaattgg acttcc          46

<210> SEQ ID NO 46
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gccttgccag cccgctcagc taggtatggt aaatgcagta tacttcct        48

<210> SEQ ID NO 47
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gccttgccag cccgctcagc taggtatggt aaatgcagta tactttct        48

<210> SEQ ID NO 48
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcctccctcg cgccatcagc accagggatt agatatcagt acaatgt         47

<210> SEQ ID NO 49
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gccttgccag cccgctcaga aggctctaag atttttgtca t               41

```
<210> SEQ ID NO 50
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gcctccctcg cgccatcaga gagcctttta gaaaacaaaa tccaga              46

<210> SEQ ID NO 51
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gccttgccag cccgctcagc actataggct gtactgtcca tttatc              46

<210> SEQ ID NO 52
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gccttgccag cccgctcaga acttctgtat gtcattgaca gtcca               45

<210> SEQ ID NO 53
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gccttgccag cccgctcaga acttctgtat atcattgaca gtcca               45

<210> SEQ ID NO 54
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gcctccctcg cgccatcaga tcactctttg gcaacgacc                      39

<210> SEQ ID NO 55
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gcctccctcg cgccatcaga tcactctttg gcagcgacc                      39
```

```
<210> SEQ ID NO 56
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gcctccctcg cgccatcagt gccaggaaaa tggaaacca                              39

<210> SEQ ID NO 57
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gcctccctcg cgccatcagt gccaggaaat tggaaacca                              39

<210> SEQ ID NO 58
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gccttgccag cccgctcagt gataaaacct ccaattcccc cta                         43

<210> SEQ ID NO 59
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gccttgccag cccgctcagt gataaaacct ccaattcctc cta                         43

<210> SEQ ID NO 60
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gccttgccag cccgctcagg ctttaatttt actggtacag tttcaat                     47

<210> SEQ ID NO 61
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gccttgccag cccgctcagt tgggccatcc attcctgg                               38

<210> SEQ ID NO 62
<211> LENGTH: 47
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gcctccctcg cgccatcagg taccagtaaa attaaagcca ggaatgg            47

<210> SEQ ID NO 63
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gcctccctcg cgccatcagg gccattgaca gaagagaaaa taaaagc            47

<210> SEQ ID NO 64
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gcctccctcg cgccatcagg gccattgaca gaagaaaaaa taaaagc            47

<210> SEQ ID NO 65
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gccttgccag cccgctcagg ggtgtggtat tcctaattga acctcc             46

<210> SEQ ID NO 66
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gccttgccag cccgctcagg ggtgtggtat tcctaattga acttcc             46

<210> SEQ ID NO 67
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gcctccctcg cgccatcagg gaagttcaat taggaatacc acaccc             46

<210> SEQ ID NO 68
<211> LENGTH: 46
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 68
gcctccctcg cgccatcagg gaagttcaat tagggatacc acaccc          46

<210> SEQ ID NO 69
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gccttgccag cccgctcaga tactaggtat ggtgaatgca gtatattt        48

<210> SEQ ID NO 70
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gccttgccag cccgctcaga tactaggtat ggtgaatgca gtatactt        48

<210> SEQ ID NO 71
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gcctccctcg cgccatcagc accagggatt agatatcaat ataatgt         47

<210> SEQ ID NO 72
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gcctccctcg cgccatcagc accagggatt agatatcagt acaatgt         47

<210> SEQ ID NO 73
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gccttgccag cccgctcaga gggctctaag atttttgtca t               41

<210> SEQ ID NO 74
<211> LENGTH: 46
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 74
gcctccctcg cgccatcaga gagcccttta gagcaaaaaa tccaga    46

<210> SEQ ID NO 75
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gcctccctcg cgccatcaga gagcccttta gagcacaaaa tccaga    46

<210> SEQ ID NO 76
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gcctccctcg cgccatcaga gagcccttta gagcaaaaaa cccaga    46

<210> SEQ ID NO 77
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gcctccctcg cgccatcaga gagcccttta gagcacaaaa cccaga    46

<210> SEQ ID NO 78
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gccttgccag cccgctcagc tgtataggct gtactgtcca tttgtc    46

<210> SEQ ID NO 79
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gccttgccag cccgctcaga acttctgtat atcattgaca gtcca    45

<210> SEQ ID NO 80
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 80
gcctccctcg cgccatcaga tcactctttg gcaacgacc                              39

<210> SEQ ID NO 81
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gcctccctcg cgccatcaga tcactctttg gcagcgacc                              39

<210> SEQ ID NO 82
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gcctccctcg cgccatcagt gccaggaaaa tggaaacca                              39

<210> SEQ ID NO 83
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gcctccctcg cgccatcagt gccaggaaat tggaaacca                              39

<210> SEQ ID NO 84
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gccttgccag cccgctcagt gataaaacct ccaattcccc cta                         43

<210> SEQ ID NO 85
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gccttgccag cccgctcagt gataaaacct ccaattcctc cta                         43

<210> SEQ ID NO 86
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
```

```
gccttgccag cccgctcagg ctttaatttt actggtacag tttcaat         47
```

<210> SEQ ID NO 87
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 87

```
gccttgccag cccgctcagt tgggccatcc attcctgg                   38
```

<210> SEQ ID NO 88
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 88

```
gcctccctcg cgccatcagg taccagtaaa attaaagcca ggaatgg         47
```

<210> SEQ ID NO 89
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 89

```
gcctccctcg cgccatcagg gccattgaca gaagagaaaa taaaagc         47
```

<210> SEQ ID NO 90
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 90

```
gcctccctcg cgccatcagg gccattgaca gaagaaaaaa taaaagc         47
```

<210> SEQ ID NO 91
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 91

```
gccttgccag cccgctcagg ggtgtggtat tcctaattga acctcc          46
```

<210> SEQ ID NO 92
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 92

```
gccttgccag cccgctcagg ggtgtggtat tcctaattga acttcc          46
```

```
<210> SEQ ID NO 93
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gcctccctcg cgccatcagg gaagttcaat taggaatacc acaccc          46

<210> SEQ ID NO 94
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gcctccctcg cgccatcagg gaagttcaat tagggatacc acaccc          46

<210> SEQ ID NO 95
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
gccttgccag cccgctcaga tactaggtat ggtgaatgca gtatattt         48

<210> SEQ ID NO 96
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gccttgccag cccgctcaga tactaggtat ggtgaatgca gtatactt         48

<210> SEQ ID NO 97
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gcctccctcg cgccatcagc accagggatt agatatcaat ataatgt          47

<210> SEQ ID NO 98
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gcctccctcg cgccatcagc accagggatt agatatcagt acaatgt          47

<210> SEQ ID NO 99
```

-continued

<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 99
gccttgccag cccgctcaga gggctctaag atttttgtca t    41

<210> SEQ ID NO 100
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 100
gcctccctcg cgccatcaga gagcccttta gagcaaaaaa tccaga    46

<210> SEQ ID NO 101
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 101
gcctccctcg cgccatcaga gagcccttta gagcacaaaa tccaga    46

<210> SEQ ID NO 102
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 102
gcctccctcg cgccatcaga gagcccttta gagcaaaaaa cccaga    46

<210> SEQ ID NO 103
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
gcctccctcg cgccatcaga gagcccttta gagcacaaaa cccaga    46

<210> SEQ ID NO 104
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
gccttgccag cccgctcagc tgtataggct gtactgtcca tttgtc    46

<210> SEQ ID NO 105
<211> LENGTH: 45
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 105
gccttgccag cccgctcaga acttctgtat atcattgaca gtcca                         45

<210> SEQ ID NO 106
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
gcctccctcg cgccatcaga tcactctttg gcaacgacc                                39

<210> SEQ ID NO 107
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gcctccctcg cgccatcaga tcactctttg gcagcgacc                                39

<210> SEQ ID NO 108
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gcctccctcg cgccatcagt gccaggaaaa tggaaacca                                39

<210> SEQ ID NO 109
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gcctccctcg cgccatcagt gccaggaaat tggaaacca                                39

<210> SEQ ID NO 110
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gccttgccag cccgctcagt gataaaacct ccaattcccc cta                           43

<210> SEQ ID NO 111
<211> LENGTH: 43
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 111
gccttgccag cccgctcagt gataaaacct ccaattcctc cta                    43

<210> SEQ ID NO 112
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gccttgccag cccgctcagg ctttaattttt actggtacag tttcaat              47

<210> SEQ ID NO 113
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gccttgccag cccgctcagt tgggccatcc attcctgg                          38

<210> SEQ ID NO 114
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gcctccctcg cgccatcagg taccagtaaa attaaagcca ggaatgg               47

<210> SEQ ID NO 115
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gcctccctcg cgccatcagg gccattgaca gaagagaaaa taaaagc               47

<210> SEQ ID NO 116
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gcctccctcg cgccatcagg gccattgaca gaagaaaaaa taaaagc               47

<210> SEQ ID NO 117
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 117
gccttgccag cccgctcagg ggtgtggtat tcctaattga acctcc                    46

<210> SEQ ID NO 118
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gccttgccag cccgctcagg ggtgtggtat tcctaattga acttcc                    46

<210> SEQ ID NO 119
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
gcctccctcg cgccatcagg gaagttcaat taggaatacc acaccc                    46

<210> SEQ ID NO 120
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gcctccctcg cgccatcagg gaagttcaat tagggatacc acaccc                    46

<210> SEQ ID NO 121
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gccttgccag cccgctcaga tactaggtat ggtgaatgca gtatattt                  48

<210> SEQ ID NO 122
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gccttgccag cccgctcaga tactaggtat ggtgaatgca gtatactt                  48

<210> SEQ ID NO 123
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123

```
gcctccctcg cgccatcagc accagggatt agatatcaat ataatgt        47
```

<210> SEQ ID NO 124
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124

```
gcctccctcg cgccatcagc accagggatt agatatcagt acaatgt        47
```

<210> SEQ ID NO 125
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125

```
gccttgccag cccgctcaga gggctctaag atttttgtca t              41
```

<210> SEQ ID NO 126
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126

```
gcctccctcg cgccatcaga gagcccttta gagcaaaaaa tccaga         46
```

<210> SEQ ID NO 127
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127

```
gcctccctcg cgccatcaga gagcccttta gagcacaaaa tccaga         46
```

<210> SEQ ID NO 128
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128

```
gcctccctcg cgccatcaga gagcccttta gagcaaaaaa cccaga         46
```

<210> SEQ ID NO 129
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129

```
gcctccctcg cgccatcaga gagcccttta gagcacaaaa cccaga         46
```

<210> SEQ ID NO 130
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
gccttgccag cccgctcagc tgtataggct gtactgtcca tttgtc        46

<210> SEQ ID NO 131
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gccttgccag cccgctcaga acttctgtat atcattgaca gtcca         45

<210> SEQ ID NO 132
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132 atagggggc aactaaagga agctctatta gatacaggag cagatgatac agtattagaa    60
gaaatgaatt tgccaggaag atggaaacca aaa                               93

<210> SEQ ID NO 133
<211> LENGTH: 1260
<212> TYPE: DNA
<213> ORGANISM: Human immunodeficiency virus

<400> SEQUENCE: 133
cctcagatca ctctttggca acgacccctc gtcaaagtaa agatagggggg gcaactaaag    60 gaagctctat tagatacagg agcagatgat acagtattag aagaaatgaa tttgccagga   120
agatggaaac caaaaatgat aggggggaatt ggaggtttta tcaaagtaag acagtatgat   180
cagataccca tagaaatctg tggacataaa gctataggta cagtattagt aggacctaca   240
cctgtcaaca taattggaag aaatctgttg actcagattg gttgcacttt aaattttccc   300
attagtccta ttgaaactgt accagtaaaa ttaaagccag gaatggatgg cccaaaagtt   360
aaacaatggc cattgacaga agaaaaaata aaagcattag tagaaatttg tacagaaatg   420
gaaaaggaag ggaaaatttc aaaaattggg cctgaaaatc catacaatac tccagtattt   480
gccataaaga aaaagacag tactaaatgg agaaaattag tagatttcag agaacttaat   540
aagagaactc aagacttctg ggaagttcaa ttaggaatac cacatcccgc agggttaaaa   600
aagaaaaaat cagtaacagt actggatgtg ggtgatgcat atttttcagt tcccttagat   660
aaagacttca ggaagtatac tgcatttacc atacctagta taaacaatga gacaccaggg   720
attagatatc agtacaatgt gcttccacag ggatggaaag gatcaccagc aatattccaa   780
agtagcatga caaaaatctt agagcctttt agaaaacaaa atccagacat agttatctat   840
caatacatgg atgatttgta tgtaggatct gacttagaaa tagggcagca tagaacaaaa   900

| | |
|---|---:|
| atagaggaac tgagacaaca tctgttgagg tggggattta ccacaccaga caaaaaacat | 960 |
| cagaaagaac ctccattcct ttggatgggt tatgaactcc atcctgataa atggacagta | 1020 |
| cagcctatag tgctgccaga aaaagacagc tggactgtca atgacataca gaagttagtg | 1080 |
| ggaaaattga attgggcaag tcagatttac gcaggbatta aagtaaagca attatgtaaa | 1140 |
| ctccttaggg gaaccaaagc actaacagaa gtaataccac taacagaaga agcagagcta | 1200 |
| gaactggcag aaaacaggga aattctaaaa gaaccagtac atggagtgta ttatgaccca | 1260 |

<210> SEQ ID NO 134
<211> LENGTH: 1260
<212> TYPE: DNA
<213> ORGANISM: Human immunodeficiency virus

<400> SEQUENCE: 134

| | |
|---|---:|
| cctcactcaa atctttggca gcgaccccctt gtctcaataa aagtagggggg ccagataaag | 60 |
| gaggctctct tagacacagg agcagatgat acagtattag aagaaataaa tttgccagga | 120 |
| aaatggaaac caaaaatgat aggaggaatt ggaggtttta tcaaagtaag acagtatgat | 180 |
| caaatactta tagaaatttg tggaaaaaag gctataggta cagtattagt aggacctaca | 240 |
| cctgtcaaca taattggaag aaatatgttg actcagcttg gatgcacact aaattttcca | 300 |
| attagtccca ttgaaactgt accagtaaaa ttaaagccag gaatggatgg cccaaaggtt | 360 |
| aaacaatggc cattgacaga agagaaaata aaagcattaa cagcaatttg tgaagaaatg | 420 |
| gagaaggaag gaaaaattac aaaaattggg cctgaaaatc catataacac tccagtattt | 480 |
| gccataaaaa agaaggacag tactaagtgg agaaaattag tagatttcag ggaactcaat | 540 |
| aaaagaactc aagacttttg ggaagttcaa ttaggaatac cacacccagc agggttaaaa | 600 |
| aagaaaaaat cagtgacagt actggatgtg ggggatgcat atttttcagt tcctttagat | 660 |
| gaaggcttca ggaaatatac tgcattcacc atacctagta taaacaatga acaccaggg | 720 |
| attagatatc aatataatgt gcttccacag ggatggaaag gatcaccagc aatattccag | 780 |
| agtagcatga caaaaatctt agagcccttt agggcacaaa atccagaaat agtcatctat | 840 |
| caatatatgg atgacttgta tgtaggatct gacttagaaa tagggcaaca tagagcaaaa | 900 |
| atagaggagt taagagaaca tctattaaag tggggattta ccacaccaga caagaaacat | 960 |
| cagaaagaac ccccatttct ttggatgggg tatgaactcc atcctgacaa atggacagta | 1020 |
| cagcctatac agctgccaga aaaggatagc tggactgtca atgatataca gaagttagtg | 1080 |
| ggaaaattaa actgggcaag tcagatttac ccagggatta agtaaggca actttgtaaa | 1140 |
| ctccttaggg ggccaaagc actaacagac atagtaccac taactgaaga agcagaatta | 1200 |
| gaattggcag agaacaggga aattctaaaa gaaccagtac atggagtata ttatgaccca | 1260 |

<210> SEQ ID NO 135
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135

| | |
|---|---:|
| tctgacaatc tctctcttat gaactatgtt aagttcgtgt agtaataaga atacacgagc | 60 |
| ttatttatcg cacgaaagaa aatgaacact cactgattt | 99 |

<210> SEQ ID NO 136
<211> LENGTH: 100

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
tctgacaatc tctgtcttat gaactatgtt aagttcgtgt ggtagtaaga gtgaacgagc      60
ttgtttatac gagagaaaga aaataaagac tcagtgattt                           100

<210> SEQ ID NO 137
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
tctgacaatc tctgtcttgt aactatgtta agttcatatg gtagtgaaag tgaacaaact      60
tgtttatacg agagagagaa aatgaagact cagtgattt                             99

<210> SEQ ID NO 138
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
tctgacaatc tctgtcttgt aagctatgtt aagttcatat ggtagtgaaa gtgaacaaac      60
ttgtttatac gagagagaga aaatgaagac tcagtgattt                           100

<210> SEQ ID NO 139
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ggcaactaaa ggaagctcta ttagatacag gagcagatga tacagtatta aagaaatga      60 atttgccagg aagatgg                                                    77

<210> SEQ ID NO 140
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ggcaactaaa ggaagctcta ttagatacag gagcagatga tacagtatta aagacatga      60 ctttgccagg aagatgg                                                    77

<210> SEQ ID NO 141
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 141
ggcaactaaa agaagcttta ttagatacag gagcagatga tacagtatta gaagacatga      60
ctttgccagg aagatgg                                                    77

<210> SEQ ID NO 142
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
ggcaactaaa agaagcttta ttagatacag gagcagatga tacagtatta gaagacatga      60
ctttgccagg aaggtgg                                                    77

<210> SEQ ID NO 143
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
ggcaactaaa ggaagctcca ttagatacag gagcagatga tacagtatta gaagacatga      60
ctttgccagg aagatgg                                                    77

<210> SEQ ID NO 144
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ggcaactaaa ggaagctcta ttagatacag gagcagacaa tacagtatta gaagacatga      60
ctttgccagg aagatgg                                                    77

<210> SEQ ID NO 145
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(57)
<223> OTHER INFORMATION: a, c, t, g, unknown or other

<400> SEQUENCE: 145
ggcaactaaa ggaagctcta ttagatacag gagcagatan nnnnnnnnn nnnnnntga       60 atttgccagg aagatgg                                                    77

<210> SEQ ID NO 146
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (40)..(57)
<223> OTHER INFORMATION: a, c, t, g, unknown or other

<400> SEQUENCE: 146
ggcaactaaa ggaagctcta ttagatacag gagcagatgn nnnnnnnnn nnnnnnntga      60 atttgccagg aagatgg                                                   77

<210> SEQ ID NO 147
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(57)
<223> OTHER INFORMATION: a, c, t, g, unknown or other

<400> SEQUENCE: 147
ggcaactaaa ggaagctcta ttagatacag gagcagatgn nnnnnnnnn nnnnnnntga      60 ctttgccagg aggatgg                                                   77

<210> SEQ ID NO 148
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(57)
<223> OTHER INFORMATION: a, c, t, g, unknown or other

<400> SEQUENCE: 148
ggcaactaaa ggaagcttta ttagatacag gagcagacgn nnnnnnnnn nnnnnnntga      60 ctttgccagg aagatgg                                                   77

<210> SEQ ID NO 149
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(57)
<223> OTHER INFORMATION: a, c, t, g, unknown or other

<400> SEQUENCE: 149
ggcaactaaa ggaagcttta ttagatacag gagcagatan nnnnnnnnn nnnnnnntga      60 ctttgccagg aagatgg                                                   77

<210> SEQ ID NO 150
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(57)
<223> OTHER INFORMATION: a, c, t, g, unknown or other
```

<400> SEQUENCE: 150
ggcaactaaa ggaagcttta ttagatacag gagcagatgn nnnnnnnnnn nnnnnnntga    60
atttgccagg aagatgg                                                 77

<210> SEQ ID NO 151
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(57)
<223> OTHER INFORMATION: a, c, t, g, unknown or other

<400> SEQUENCE: 151
ggcaactaaa ggaagcttta ttagatacag gagcagatgn nnnnnnnnnn nnnnnnntga    60
ctttgccagg aaggtgg                                                 77

<210> SEQ ID NO 152
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
ggcaactaaa ggaagcttta ttagatacag gagcagatga tacagtatta aagacatga    60 ctttgccagg aggatgg                                                 77

<210> SEQ ID NO 153
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
ggcaactaaa ggaagcttta ttagatacag gagcagatga tacagtatta aagacgtga    60 ctttgccagg aagatgg                                                 77

<210> SEQ ID NO 154
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ggcaactaaa ggaagcttta ttagatacag gagcagatga tacagtatta aagacgtga    60 ctttgccagg aagatgg                                                 77

<210> SEQ ID NO 155
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155

```
ggcaactaaa ggaagcttta ttagatacag gagcagatga tacagtatta gaagaaatga    60
atttgccagg aagatgg                                                    77

<210> SEQ ID NO 156
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
ggcaactaaa ggaagcttta ttagatacag gagcagatga tacagtatta gaagacatga    60
ctttgccagg aagatgg                                                    77

<210> SEQ ID NO 157
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
cttttagaaa acaaaatcca gacatagtta tctatcaata catggatgat ttgtatgtag    60
gatctgactt agaaat                                                     76

<210> SEQ ID NO 158
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
cttttagaaa acagaatcca gacatagtta tctatcaata catggatgat ttgtatgtag    60
gatctgactt agaaat                                                     76

<210> SEQ ID NO 159
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
cttttagaaa acagaatcca gacatagtta tctgtcaata catggatgat ttgtatgtag    60
gatctgactt agaaat                                                     76

<210> SEQ ID NO 160
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
cttttagaaa acagaatcca gacatagtta tctatcaata catggatgat ttgtatgtag    60
gatctgactt agaaat                                                     76
```

<210> SEQ ID NO 161
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
cttttagaaa acagaatcca gacatagtta tctatcaata catggatgat ttgtatgtag     60
gatctgactt agaaat                                                     76

<210> SEQ ID NO 162
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
cttttagaaa gcagaatcca gacatagtga tctatcaata catggatgat ttgtatgtag     60
gatctgactt agaaat                                                     76

<210> SEQ ID NO 163
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
cttttagaaa gcagaatcca gacatagtta tctatcaata catggatgat ttgtatgtag     60
gatctgactt agaaat                                                     76

<210> SEQ ID NO 164
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
cttttagaga acagaatcca gaaatagtta tctatcaata catggatgat ttgtatgtag     60
gatctgactt agaaat                                                     76

<210> SEQ ID NO 165
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
cttttagaga acagaatcca gacatagtga tctatcaata catggatgat ttgtatgtag     60
gatctgactt agaaat                                                     76

<210> SEQ ID NO 166
<211> LENGTH: 76
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 166
cttttagaga acagaatcca gacatagtta tctatcaata catggatgat ttgtatgtag      60
gatctgactt agaaat                                                      76

<210> SEQ ID NO 167
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
cttttagaga acagaatcca gacatagtta tctatcaata catggatgat ttgtatgtag      60
gatctgactt agaaat                                                      76

<210> SEQ ID NO 168
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
cttttagaga acagaatcca gacatagtta tctgtcaata catggatgat ttgtatgtag      60
gatctgactt agaaat                                                      76

<210> SEQ ID NO 169
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(53)
<223> OTHER INFORMATION: a, c, t, g, unknown or other

<400> SEQUENCE: 169
tttttagaaa acagaatcca gacatagtta tctannnnnn nnnnnnnnnn nnntatgtag      60
gatctgactt agaaat                                                      76

<210> SEQ ID NO 170
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(53)
<223> OTHER INFORMATION: a, c, t, g, unknown or other

<400> SEQUENCE: 170
cttttagaaa acagaatcca gacatagtga tctannnnnn nnnnnnnnnn nnntatgtag      60
gatctgactt agaaat                                                      76

<210> SEQ ID NO 171
```

```
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(53)
<223> OTHER INFORMATION: a, c, t, g, unknown or other

<400> SEQUENCE: 171
cttttagaaa acagaatcca gacatagtta tctannnnnn nnnnnnnnnn nnntatgtag    60
gatctgactt agaaat                                                   76

<210> SEQ ID NO 172
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(53)
<223> OTHER INFORMATION: a, c, t, g, unknown or other

<400> SEQUENCE: 172
cttttagaaa acagaatcca gacatagtta tctannnnnn nnnnnnnnnn nnntatgtag    60
gatctgactt agaaat                                                   76

<210> SEQ ID NO 173
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(53)
<223> OTHER INFORMATION: a, c, t, g, unknown or other

<400> SEQUENCE: 173
cttttagaaa acagaatcca gacatagtta tctannnnnn nnnnnnnnnn nnntatgtag    60
g                                                                   61

<210> SEQ ID NO 174
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(53)
<223> OTHER INFORMATION: a, c, t, g, unknown or other

<400> SEQUENCE: 174
cttttagaaa acagaatcca gacatagtta tctannnnnn nnnnnnnnnn nnntatgtag    60
gatctgactt agaaat                                                   76

<210> SEQ ID NO 175
<211> LENGTH: 76
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 175
cttttagaaa acagaatcca gacatagtga tctatcaata catggatgat ttgtatgtag      60
gatctgactt agaaat                                                      76

<210> SEQ ID NO 176
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
cttttagaaa acagaatcca gacatagtta tctatcaata catggatgat ttgtatgtag      60
gatctgactt agaaat                                                      76

<210> SEQ ID NO 177
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
cttttagaaa acagaatcca gacatagtta tctatcaata catggatgat ttgtatgtag      60
gatctgactt agaaat                                                      76

<210> SEQ ID NO 178
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
aatactccag tatttgccat aaagaaaaaa gacagtacta aatggagaaa attagtagat      60
ttcagagaac ttaata                                                      76

<210> SEQ ID NO 179
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
aatactccaa tatttgctat aaagaaaaaa gacagcaata aatggagaaa attagtagac      60
tttagagaac ttaata                                                      76

<210> SEQ ID NO 180
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
```

```
aatactccaa tatttgctat aaagaaaaaa gacagcacta aatggagaaa attagtagat    60
ttcagagaac ttaata                                                    76

<210> SEQ ID NO 181
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
aatactccaa tatttgctat aaagaaaaaa gacagcaata aatggagaaa attagtagat    60
ttcagagaac ttaata                                                    76

<210> SEQ ID NO 182
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
aatactccaa tatttgctat aaagaaaaaa gacagtacta aatggagaaa attagtagat    60
ttcagagaac ttaata                                                    76

<210> SEQ ID NO 183
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
aatactccaa tatttgctat aaagaaaaaa gacagcaata aatggagaaa attagtagat    60
ttcagagaac ttaata                                                    76

<210> SEQ ID NO 184
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
aatactccaa tatttgctat aaagaaaaaa gacagcaata aatggagaaa attagtagat    60
ttcagagaac ttaata                                                    76

<210> SEQ ID NO 185
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
aatactccaa tatttgctat aaagaaaaaa gacagcaata aatggagaaa attagtagat    60
ttcagagaac ttaata                                                    76
```

```
<210> SEQ ID NO 186
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
aatactccaa tatttgctat aagaaaaaa gacagtgcta aatggagaaa attagtagat      60
ttcagagaac ttaata                                                     76

<210> SEQ ID NO 187
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
aatactccaa tatttgctat aagaaaaaa gacagtgcta aatggagaaa attagtagat      60
ttcagagaac ttaata                                                     76

<210> SEQ ID NO 188
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
aatactccaa tatttgctat aagaaaaaa gacagtgcta aatggagaaa attagtagat      60
ttcagagaac ttaata                                                     76

<210> SEQ ID NO 189
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
aatactccaa tatttgctat aagaaaaaa gacagtgcta aatggagaaa attagtagat      60
ttcagagaac ttaata                                                     76

<210> SEQ ID NO 190
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
aatactccaa tatttgctat aagaaaaaa gacagtgcta aatggagaaa attagtagat      60
ttcagagaac ttaata                                                     76

<210> SEQ ID NO 191
<211> LENGTH: 76
<212> TYPE: DNA
<213> ORGANISM: Artificial Sequence
<220> FEATURE:
```

<223> OTHER INFORMATION: Description of Artificial Sequence: Synthetic
       oligonucleotide

<400> SEQUENCE: 191
aatactccaa tatttgctat aaagaaaaaa gacagcaata aatggagaaa attagtagat    60
ttcagagaac ttaata                                                   76

<210> SEQ ID NO 192
<211> LENGTH: 76
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 192
aatactccaa tatttgctat aaagaaaaaa gacagtacta aatggagaaa attagtagat    60
ttcagagaac ttaata                                                   76

<210> SEQ ID NO 193
<211> LENGTH: 76
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 193
aatactccaa tatttgctat aaagaaaaaa gacagcaata aatggagaaa attagtagat    60
ttcagagaac ttaata                                                   76

<210> SEQ ID NO 194
<211> LENGTH: 76
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 194
aatactccaa tatttgctat aaagaaaaaa gacagtacta aatggagaaa attagtagat    60
ttcagagaac ttaata                                                   76

<210> SEQ ID NO 195
<211> LENGTH: 76
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 195
aatactccaa tatttgctat aaagaaaaaa gacagcaata aatggagaaa attagtagat    60
ttcagagaac ttaata                                                   76

<210> SEQ ID NO 196
<211> LENGTH: 76
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 196
aatactccaa tatttgctat aaagaaaaaa gacagcaata aatggagaaa attagtagat    60
ttcagagaac ttaata    76

<210> SEQ ID NO 197
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
aatactccaa tatttgctat aaagaaaaaa gacagcaata aatggagaaa attagtagat    60
ttcagagaac ttaata    76

<210> SEQ ID NO 198
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
aatactccaa tatttgctat aaagaaaaaa gacagcaata aatggagaaa attagtagat    60
ttcagagaac ttaata    76

<210> SEQ ID NO 199
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
aatactccaa tatttgctat aaagaaaaaa gcagcagcta aatggagaaa attagtagat    60
ttcagagaac ttaata    76

<210> SEQ ID NO 200
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
aatactccaa tatttgctat aaagaaaaaa gacagtacta aatggagaaa attagtagat    60
ttcagagaac ttaata    76

<210> SEQ ID NO 201
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
aatactccaa tatttgctat aaagaaaaaa gacagcaata aatggagaaa attag    55

<210> SEQ ID NO 202
<211> LENGTH: 55

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
aatactccaa tatttgctat aaagaaaaaa gacagcaata aatggagaaa attag       55
```